US008846331B2

(12) United States Patent
McNaughton et al.

(10) Patent No.: US 8,846,331 B2
(45) Date of Patent: Sep. 30, 2014

(54) ASYNCHRONOUS MAGNETIC BEAD ROTATION SENSING SYSTEMS AND METHODS

(75) Inventors: Brandon H. McNaughton, Ann Arbor, MI (US); Paivo Kinnunen, Ann Arbor, MI (US); Raoul Kopelman, Ann Arbor, MI (US); Alan Hunt, Plymouth, MI (US); Roy Clarke, Ann Arbor, MI (US); Irene Sinn, Ann Arbor, MI (US); Remy Elbez, Ann Arbor, MI (US); Theodore Albertson, Bloomfield, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/220,381

(22) Filed: Aug. 29, 2011

(65) Prior Publication Data

US 2012/0164680 A1   Jun. 28, 2012

Related U.S. Application Data

(60) Provisional application No. 61/402,310, filed on Aug. 27, 2010, provisional application No. 61/474,123, filed on Apr. 11, 2011.

(51) Int. Cl.
*C12Q 1/02*   (2006.01)

(52) U.S. Cl.
USPC ......................................... 435/29; 435/173.1

(58) Field of Classification Search
None
See application file for complete search history.

(56) References Cited

U.S. PATENT DOCUMENTS

| | | |
|---|---|---|
| 3,676,679 A | 7/1972 | Waters |
| 4,778,758 A | 10/1988 | Ericsson et al. |
| 5,171,534 A | 12/1992 | Smith et al. |
| 5,232,839 A | 8/1993 | Eden et al. |
| 5,252,493 A | 10/1993 | Fujiwara et al. |
| 5,293,210 A | 3/1994 | Berndt |
| 5,336,600 A | 8/1994 | Monget |
| 5,374,527 A | 12/1994 | Grossman |
| 5,434,056 A | 7/1995 | Monget et al. |
| 5,516,670 A | 5/1996 | Kuehnle et al. |
| 5,534,527 A | 7/1996 | Black et al. |
| 5,593,854 A | 1/1997 | Berndt |
| 5,716,798 A | 2/1998 | Monthony et al. |
| 5,770,388 A | 6/1998 | Vorpahl |
| 5,770,440 A | 6/1998 | Berndt |
| 5,814,474 A | 9/1998 | Berndt |
| 5,888,760 A | 3/1999 | Godsey et al. |
| 5,910,300 A | 6/1999 | Tournier et al. |
| 5,998,224 A | 12/1999 | Rohr et al. |
| 5,998,517 A | 12/1999 | Gentle, Jr. et al. |
| 6,002,817 A | 12/1999 | Kopelman et al. |
| 6,027,946 A | 2/2000 | Weitschies et al. |
| 6,096,272 A | 8/2000 | Clark et al. |
| 6,107,102 A | 8/2000 | Ferrari |
| 6,143,558 A | 11/2000 | Kopelman et al. |
| 6,159,686 A | 12/2000 | Kardos et al. |
| 6,275,031 B1 | 8/2001 | Simmonds |
| 6,372,485 B1 | 4/2002 | Clark et al. |
| 6,395,506 B1 | 5/2002 | Pitner et al. |
| 6,437,563 B1 | 8/2002 | Simmonds et al. |
| 6,518,747 B2 | 2/2003 | Sager et al. |
| 6,586,259 B1 | 7/2003 | Mahan et al. |
| 6,596,532 B1 | 7/2003 | Hyman et al. |
| 6,597,176 B2 | 7/2003 | Simmonds et al. |
| 6,632,655 B1 | 10/2003 | Mehta et al. |
| 6,660,381 B2 | 12/2003 | Halas et al. |
| 6,777,226 B2 | 8/2004 | Jeffrey et al. |
| 6,780,581 B2 | 8/2004 | Vesey et al. |
| 6,825,655 B2 | 11/2004 | Minchole et al. |
| 6,900,030 B2 | 5/2005 | Pitner et al. |
| 6,927,570 B2 | 8/2005 | Simmonds et al. |
| 7,115,384 B2 | 10/2006 | Clark et al. |
| 7,183,073 B2 | 2/2007 | Hyman et al. |
| 7,323,139 B2 | 1/2008 | LaBorde et al. |
| 7,341,841 B2 | 3/2008 | Metzger et al. |
| 7,547,554 B2 | 6/2009 | Odefey |
| 7,564,245 B2 | 7/2009 | Lee |
| 7,575,934 B2 | 8/2009 | Atwood |
| 7,691,600 B2 | 4/2010 | Mercader Badia et al. |
| 2002/0150914 A1 | 10/2002 | Andersen et al. |
| 2003/0012693 A1 | 1/2003 | Otillar et al. |
| 2003/0076087 A1 | 4/2003 | Minchole et al. |
| 2003/0124516 A1 | 7/2003 | Chung et al. |

(Continued)

FOREIGN PATENT DOCUMENTS

| | | |
|---|---|---|
| WO | WO-00/67037 A2 | 11/2000 |
| WO | WO-01/14591 A1 | 3/2001 |
| WO | WO-03/019188 A1 | 3/2003 |
| WO | WO-2006/104700 A1 | 10/2006 |
| WO | WO-2007/120095 A1 | 10/2007 |

(Continued)

OTHER PUBLICATIONS

Agayan et al., Optical Manipulation of Metal-Silica Hybrid Nanoparticles, Proceedings of SPIE, 5514:502-513 (2004).
Anker et al., Magnetically Modulated Optical Nanoprobes, Appl. Phys. Letts., 82:1102-1104 (2003).

(Continued)

*Primary Examiner* — Allison Ford
*Assistant Examiner* — Susan E Fernandez
(74) *Attorney, Agent, or Firm* — Marshall, Gerstein & Borun LLP

(57) ABSTRACT

Described herein are various methods, devices and systems for performing asynchronous magnetic bead rotation (AMBR) to detect and monitor cellular growth and/or behavior. Cluster rotation of magnetic particles for AMBR is descried. In particular, described herein are systems for the parallel analysis of multiple wells of a sample plate. Also described herein are methods for controlling the illumination and imaging of rotating magnetic particles.

16 Claims, 55 Drawing Sheets

(56) References Cited

U.S. PATENT DOCUMENTS

| | | | |
|---|---|---|---|
| 2003/0169032 | A1 | 9/2003 | Minchole et al. |
| 2004/0033627 | A1 | 2/2004 | Aytur et al. |
| 2004/0058458 | A1 | 3/2004 | Anker et al. |
| 2005/0048672 | A1 | 3/2005 | Luxton et al. |
| 2005/0286342 | A1* | 12/2005 | Garcia et al. ............... 366/273 |
| 2006/0008924 | A1 | 1/2006 | Anker et al. |
| 2006/0057578 | A1 | 3/2006 | Willner et al. |
| 2006/0160171 | A1 | 7/2006 | Bachur et al. |
| 2006/0210987 | A1 | 9/2006 | Gleich |
| 2007/0020720 | A1 | 1/2007 | Colin et al. |
| 2007/0037225 | A1 | 2/2007 | Metzger et al. |
| 2007/0205767 | A1 | 9/2007 | Xu et al. |
| 2008/0038769 | A1* | 2/2008 | Bernardi et al. ............. 435/29 |
| 2008/0220411 | A1* | 9/2008 | McNaughton et al. ......... 435/5 |
| 2009/0085557 | A1 | 4/2009 | Krozer et al. |
| 2009/0136953 | A1 | 5/2009 | Gold et al. |
| 2009/0269854 | A1 | 10/2009 | Kageyama |
| 2010/0033158 | A1 | 2/2010 | Dittmer et al. |
| 2010/0068755 | A1 | 3/2010 | Walsh et al. |
| 2010/0072994 | A1 | 3/2010 | Lee et al. |
| 2010/0129857 | A1 | 5/2010 | Walsh et al. |

FOREIGN PATENT DOCUMENTS

| | | |
|---|---|---|
| WO | WO-2008/075285 A1 | 6/2008 |
| WO | WO-2009/037636 A1 | 3/2009 |
| WO | WO-2010/026551 A1 | 3/2010 |
| WO | WO-2010/041178 A1 | 4/2010 |
| WO | WO-2010/048511 A1 | 4/2010 |
| WO | WO-2011/021142 A1 | 2/2011 |
| WO | WO-2012/027747 A2 | 3/2012 |

OTHER PUBLICATIONS

Astalan et al., Biomolecular Reactions Studied Using Changes in Brownian Rotation Dynamics of Magnetic Particles, Biosensors and Bioelectronics, 19:945-951 (2004).

Bao et al., Cell and Molecular Mechanics of Biological Materials, Nat. Mat., 2:715-725 (2003).

Behrend et al., Brownian Modulated Optical Nanoprobes, Appl. Phys. Letts., 84:154-156 (2004).

Behrend et al., Microheology with Modulated Optical Nanoprobes (MOONs), J. Magnetism and Magnetic Mats., 293:663-670 (2005).

Bhiladvala et al., Effect of Fluids on the Q Factor and Resonance Frequency of Oscillating Micrometer and Nanometer Scale Beams, Phys. Rev. E, 69:36307-1-36307-5 (2004).

Biswal et al., Micromixing with Linked Chains of Paramagnetic Particles, Anal. Chem., 76:6448-6455 (2004).

Bornhop et al., Advance in contrast agents, reporters, and detection, Journal of Biomedical Optics, 6(2):106-115 (2001).

Boucher et al., Bad bugs, no drugs: no Eskape! an update from the Infectious Diseases Society of America, Clin. Infect. Dis., 48(1):1-12 (2009).

Cebers, Dynamics of an Active Magentic Particle in a Rotating Magentic Field, Phys. Rev. E., 73:021505-1-021505-5 (2006).

Chu et al., *Staphylococcus aureus* bacteremia in patients with prosthetic devices: costs and outcomes, Am. J. Med., 118(12):1416 (2005).

Connolly et al., Experimental Evaluation of the Magnetic Properties of Commerically Available Magnetic Microspheres, Bio-Medical Materials and Engineering, 15:421-431 (2005).

Crick, The Physical Properties of Cytoplasm. A Study by Means of the Magnetic Particle Method. Part II. Theoretical Treatment, Strangeways Research Laboratory, Cambridge, 505-532 (1950).

Crick, et al., The Physical Properties of Cytoplasm A Study by Means of the Magnetic Particle Method—Part I Experimental, Strangeways Research Laboratory, 37-80 (1949).

Deresinski, Counterpoint: Vancomycin and *Staphylococcus aureus*—an antibiotic enters obsolescence, Clin. Infest. Dis., 44(12):1543-8 (2007).

Ekinci et al., Nanoelectromechnical Systems, Review of Scientific Instruments, 76:061101-1-061101-12 (2005).

Elbez et al., Nanoparticle induced cell magneto-rotation: monitoring morphology, stress and drug sensitivity of a suspended single cancer cell, PLOS One, 6(12):e28475 (2011).

Elfwing et al., Observing Growth and Division of Large Numbers of Individual Bacteria by Image Analysis, Applied and Environmental Microbiology, 70(2):675-678 (2004).

Fennimore et al., Rotational Actuators based on Carbon Nanotubes, Nature, 424:408-410 (2003).

Fratamico et al., Detection of *Escherichia coli* 0157:H7 using a surface plasmon resonance biosensor, Biotechnology Techniques, 12(7):571-6 (1998).

Fujinami et al., Sensitive detection of bacteria and spores using a portable bioluminescence ATP measurement assay system distinguishing from white powder materials, J. Health Sci., 50:126-32 (2004).

Gfeller et al., Micromechanical oscillators as rapid biosensor for the detection of active growth of *Escherichia coli*, Biosens. Biolectron., 21(3):528-33 (2005).

Gitterman et al., Order and Choas: Are They Contradictory or Complementary? Eur. J. Phys., 23:119-122 (2002).

Godin et al., Using buoyant mass to measure the growth of single cells, Nat. Methods, 7(5):387-90 (2010).

Gu et al., Using Biofunicational Magnetic Nanoparticles to Capture Gram-Negative Bacteria at an Ultra-Low Concentration, Chemical Communications, 15:1966-1967 (2003).

Hafeli et al., Characterization of Magnetic Particles and Microspheres and Their Magnetophoretic Mobility Using a Digital Microscopy Method, European Cells and Materials, 3:24-27 (2002).

Haukanes et al., Application of Magnetic Beads in Bioassays, Bio-Technology, 11:60-63 (1993).

Horvath et al., Magnetic Dimer Motion Effects in a Rotating Magnetic Field (a Qualitative Model of Magnetoviscosity and Permittivity in Magnetorheological Suspensions), Czech J. Phys., 43:671-681 (1993).

Hulteen et al., Nanosphere Lithography: A Materials General Fabrication Process for Periodic Particle Array Surfaces, J. Vac. Sci. Technol. A., 13:1553-1558 (1995).

Ilic et al., Single Cell Detection with Micromechanical Oscillators, J. Vacuum Sci. & Tech. B: Microelectronics and Nanometer Structures, 19:2825-2828 (2001).

Ilic et al., Virus Detection Using Nanoelectromechanical Devices, Appl. Phys. Lett., 85:2604-2606 (2004).

Ilic et al., Mechanical resonant immunospecific biological detector, Appl. Phys. Lett., 77:450-2 (2000).

Ishiyama et al., Swimming of Magnetic Micro-Machines under a Very Wide-Range of Reynolds Number Conditions, IEEE Trans. Magn., 37(4):2868-2870 (2001).

Jain, Understanding barriers to drug delivery: high resolution in vivo imaging is key, Clinical Cancer Research, 5(7):1605-1606 (1999).

Janssen et al., Controlled torque on superparamagnetic beads for functional biosensors, Biosens. Bioelectron., 24(7):1937-41 (2009).

Jiang et al., A lost-wax approach to monodisperse colloids and their crystals, Science, 291:453-457 (2001).

Kashevsky, Nonlinear Flow-Particle Interaction in Suspensions of Fine Quasi-Rigid Ferroparticles: A Giant Magnetic Effect of Fluid Rotation, J. Phys. D: Appl. Phys., 34:518-524 (2001).

Kinnunen et al., Monitoring the growth and drug susceptibility of individual bacteria using asynchronous magnetic bea rotation sensors, Biosensors and Bioelectronics, 26(5):2751-5 (2010).

Klevens et al., Changes in the epidemiology of methicillin-resistant *Staphylococcus aureus* in intensive care units in US hospitals, 1992-2003, Clin. Infest. Dis., 42(3):389-91 (2006).

Kneipp et al., Surface-Enhanced Raman Spectroscopy in Single Living Cells Using Gold Nanoparticles , Applied Spectroscopy, 56(2):150-154 (2002).

Korneva et al., Carbon Nanotubes Loaded with Magnetic Particles, Nano Lett., 5:879-884 (2005).

Koskinen et al., Development of a rapid assay methodology for antimicrobial susceptibility testing of *Staphylococcus aureus*, Diagn. Microbiol. Infect. Dis., 62(3):306-16 (2008).

(56) References Cited

OTHER PUBLICATIONS

Kumar et al., Duration of hypotension before initiation of effective antimicrobial therapy is the critical determinant of survival in human septic shock, Crit. Care Med., 34(6):1589-96 (2006).
Kurlyandskaya et al., Magnetic Dynabeads Detection by Sensitive Element Based on Giant Magnetoimpedance, Biosensors and Bioelectronics, 20:1611-1616 (2005).
Lapointe et al., Statis and Dynamic Properties of Magnetic Nanowires in Nematic Fluids, J. Appl. Phys., 97:10 (2005).
Lu et al., Nanophotonic Crescent Moon Structures with Sharp Edge for Ultrasensitive Biomolecular Detection by Local Electromagnetic Field Enhancement Effect, Nano Lett., 5:119-124 (2005).
MacDougall et al., Antimicrobial stewardship programs in health care systems, Clin. Microbiol. Rev., 18(4):638-56 (2005).
Mayer et al., Measurement of the Fluorescence Lifetime in Scattering Media by Frequency-Domain Photon Migration , Applied Optics, 38:4930-4938 (1999).
McNaughton et al. Sudden Breakdown in Linear Response of a Rotationally Driven Magnetic Microparticle and Application to Physical and Chemical Microsensing (J. Phys. Chem. B, 110(38), pp. 18958-18964 (2006).
McNaughton et al., Fabrication of Uniform Half-Shell Magnetic Nanoparticles and Microspheres with Applications as Magnetically Modulated Optical Nanoprobes, arXiv:cond-mat/0506418v1, pp. 1-6 (2005).
McNaughton et al., Physiochemical Microparticle Sensors Based on Nonlinear Magnetic Oscillations, Sensors and Actuators B., 121:330-340 (2007).
McNaughton et al., Compact sensor for measuring nonlinear rotational dynamics of driven magnetic microspheres with biomedical applications, JMMM, 321:1648-52 (2009).
McNaughton et al., Single bacterial cell detection with nonlinear rotation rate shifts of driven magnetic microspheres, Appl. Phys. Lett., 91:224105 (2007).
Melle et al., Structure and dynamics of magnetorheological fluids in rotating magnetic fields, Phys. Rev. E, 61(4):4111-7 (2000).
Merkt et al., Capped Colloids as Light-Mills in Optical Traps, arXiv:cond-mat/0605463v1, pp. 1-10 (2006).
Metzger, Amorphous Whiskers of a Cobalt-Gold Alloy, Nature, 212:176-177 (1966).
Moller et al., Ultrafine particles cause cytoskeletal dysfunctions in macrophages, Toxicology and Applied Pharmacology, 182(3):197-207 (2002).
National Nosocomial Infections Surveillance System, National Nosocomial Infections Surveillance (NNIS) System Report, data summary from Jan. 1992 through Jun. 2004, issued Oct. 2004, Am. J. Infect. Control., 32(8):470-85 (2004).
Newman et al., Motions of a Magnetic Particle in a Viscous Medium, J. Appl. Phys., 39:5566-5569 (1968).
Nie et al., Probing Single Molecules and Single Nanoparticles by Surface-Enhanced Raman Scattering, Science, 275(5303):1102-1106 (1997).
Noskin et al., National trends in *Staphylococcus aureus* infection rates: impact on economic burden and mortality over a 6-year period (1998-2003), Clin. Infect. Dis., 45(9):1132-40 (2007).
Nozawa et al., Smart Control of Monodisperse Stöber Silica Particles: Effect of Reactant Addition Rate on Growth Process, Langmuir, 21:1516-1523 (2005).
Olsvik et al., Magnetic Separation Techniques in Diagnostic Microbiology, Clinical Microbiology Reviews, 7:43-54 (1994).
Paul et al., Stochastic Dynamics of Nanoscale Mechanical Oscillators Immersed in a Viscous Fluid, Phys. Rev. Lett., 92:235501-1-235501-4 (2004).
Petkus et al., Detection of FITC-Cortisol via Modulated Supraparticle Lighthouses, Anal. Chem., 78:1405-1411 (2006).
Puig-de-Morales et al., Measurement of Cell Microrheology by Magnetic Twisting Cytometry with Frequency Domain Demodulation, J. Appl. Physiol., 91:1152-1159 (2001).
Purcell et al., Life at Low Reynolds Number, Am. J. Phys., 45:3-11 (1977).
Richards-Kortum et al., Quantitative Optical Spectroscopy for Tissue Diagnosis, Annual Review of Physical Chemistry, 47:555-606 (1996).
Rife et al., Design and Performance of GMR Sensors for the Detection of Magnetic Microbeads in Biosensors, Sensors and Actuators A., 107:209-218 (2003).
Sakoulas et al., Relationship of MIC and bactericidal activity to efficacy of vancomycin for treatment of methicillin-resistant *Staphylococcus aureus* bacteremia, J. Clin. Microbiol., 42(6):2398-402 (2004).
Shankar et al., Experimental Determination of the Kinematic Viscosity of Glycerol-Water Mixtures, Proc. R. Soc. Lond. A., 444:573-581 (1994).
Shelton et al., Nonlinear Motion of Optically Torqued Nanorods, Phys. Rev. E., 71:036204-1-036204-8 (2005).
Shen et al., In situ Detection of Single Micron-Sized Magnetic Beads using Magnetic Tunnel Junction Sensors, Appl. Phys. Letts., 86:253901-1-253901-3 (2005).
Shine et al., The Rotation of a Suspended Axisymmetric Ellipsoid in a Magnetic Field, Rheol. Acta, 26:152-161 (1987).
Spellberg et al., Trends in antimicrobial drug development: implications for the future, Clin. Infect. Dis., 38(9):1279-86 (2004).
Stober et al., Controlled Growth of Monodisperse Silica Spheres in the Micron Size Range, J. Coll. Interface Sci., 26:62-69 (1968).
Su et al., A self-assembled monolayer-based piezoelectric immunosensor for rapid detection of *Escherichia coli* O157:H7, Biosens. Bioelectron., 19(6):563-74 (2004).
Talbot et al., Bad bugs need drugs: an update on the development pipeline from the Antimicrobial Availability Task Force of the Infectious Diseases Society of America, Clin. Infect. Dis., 42(5):657-68 (2006).
Taylor et al., Real-time molecular and cellular analysis: the new frontier of drug discovery, Current Opinion in Biotechnology, 12(1):75-81 (2001).
Tenover et al., The challenges of emerging infectious diseases. Development and spread of multiply-resistant bacterial pathogens, JAMA, 275(4):300-4 (1996).
Tiemersma et al., Methicillin-resistant *Staphylococcus aureus* in Europe, 1999-2002, Emerg. Infect. dis., 10(9):1627-34 (2004).
Valberg et al., Magnetic particle motions within living cells. Physical theory and techniques, Biophysical Journal, 52(4):537-550 (1987).
Varshney, Interdigitated array microelectrodes based impedance biosensors for detection of bacterial cells, Biosens. Bioelectron., 24(10):2951-60 (2009).
Verbridge et al., High Quality Factor Resonance at Room Temperature with Nanostrings Under High Tensile Stress, J. Appl. Phys., 99:124304-1-124304-8 (2006).
Vignola et al., Effect of Viscous Loss on Mechanical Resonators Designed for Mass Detection, Appl. Phys. Lett., 88:041921-1-041921-3 (2006).
Wagnieres et al., In vivo fluorescence spectroscopy and imaging for oncological applications, Photochemistry and Photobiology, 68(5):603-632 (1998).
Waigh, Microrheology of Complex Fluids, Rep. Prog. Phys., 68:685-742 (2005).
Witte et al., Changing pattern of antibiotic resistance in methicillin-resistant *Staphylococcus aureus* from German hospitals, Infect. Control Hosp. Epidemiol., 22(11):683-6 (2001).
Witte, Antibiotic resistance in gram-positive bacteria: epidemiological aspects, J. Antimicrob. Chemother., 44 Suppl A:1-9 (1999).
Yamazaki et al., Three-Dimensional Analysis of Swimming Properties of a Spiral-Type Magnetic Micro-Machine, Sensors and Actuators A., 105:103-108 (2003).
Yang et al., Interdigitated Array microelectrode-based electrochemical impedance immunosensor for detection of *Escherichia coli* O157:H7, Anal. Chem., 76(4):1107-13 (2004).
Zhao et al., A Rapid Bioassay for Single Bacterial Cell Quantitation Using Bioconjugated Nanoparticles, PNAS, 101:15027-15032 (2004).

* cited by examiner

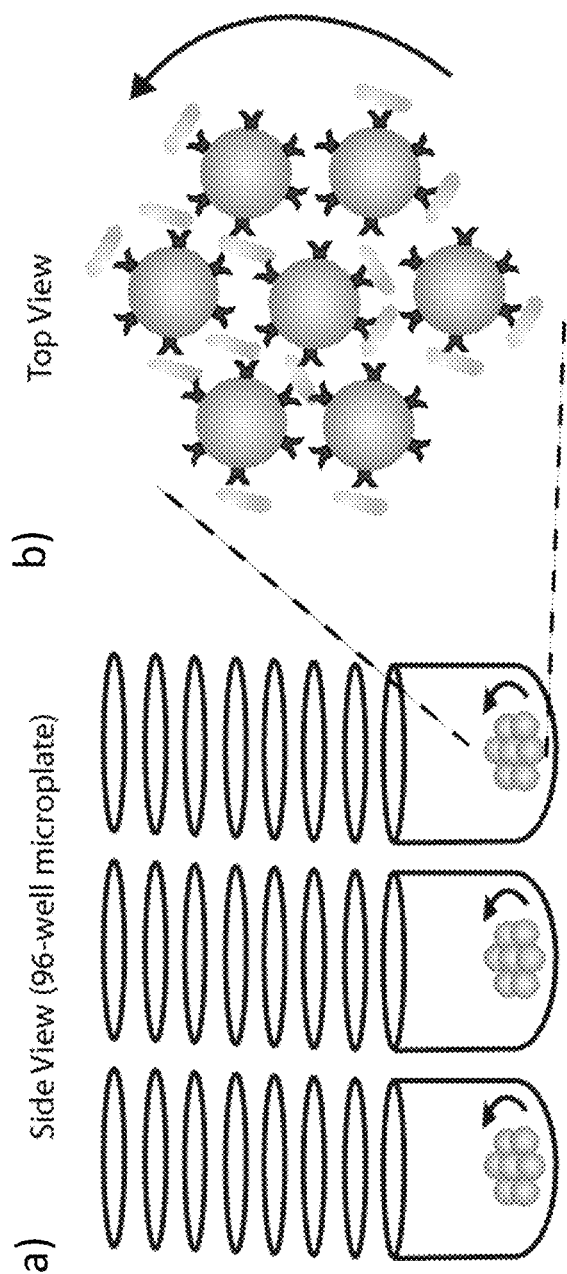
FIGS. 11a-b

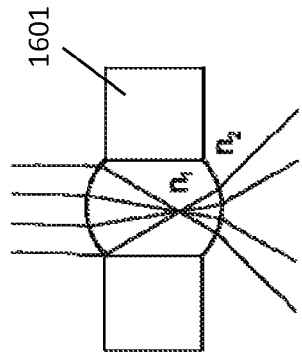
FIG. 16 E
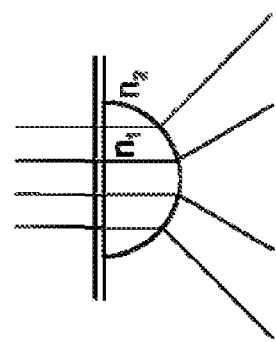
FIG. 16 B
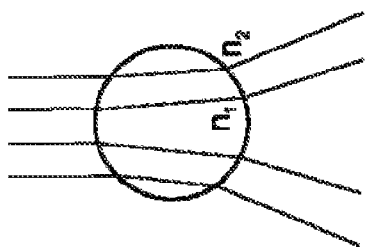
FIG. 16 D
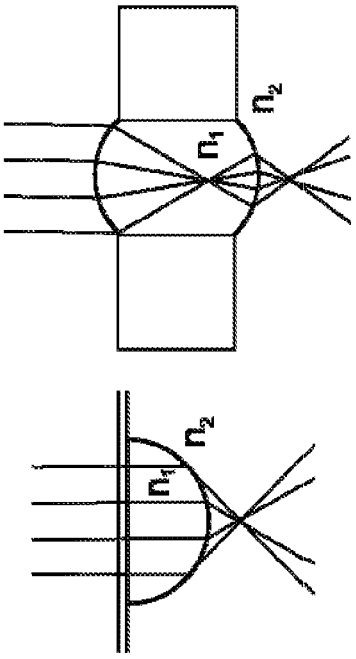
FIG. 16 A
FIG. 16 F
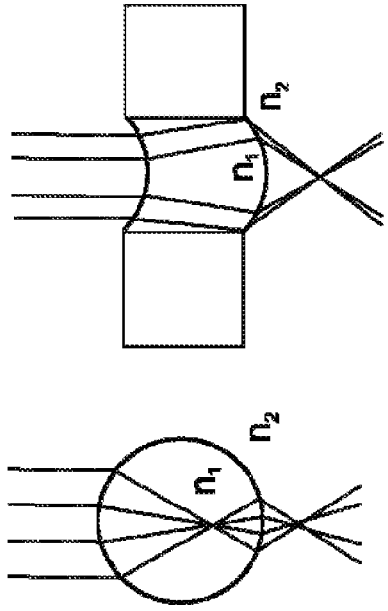
FIG. 16 C
FIG. 16 G

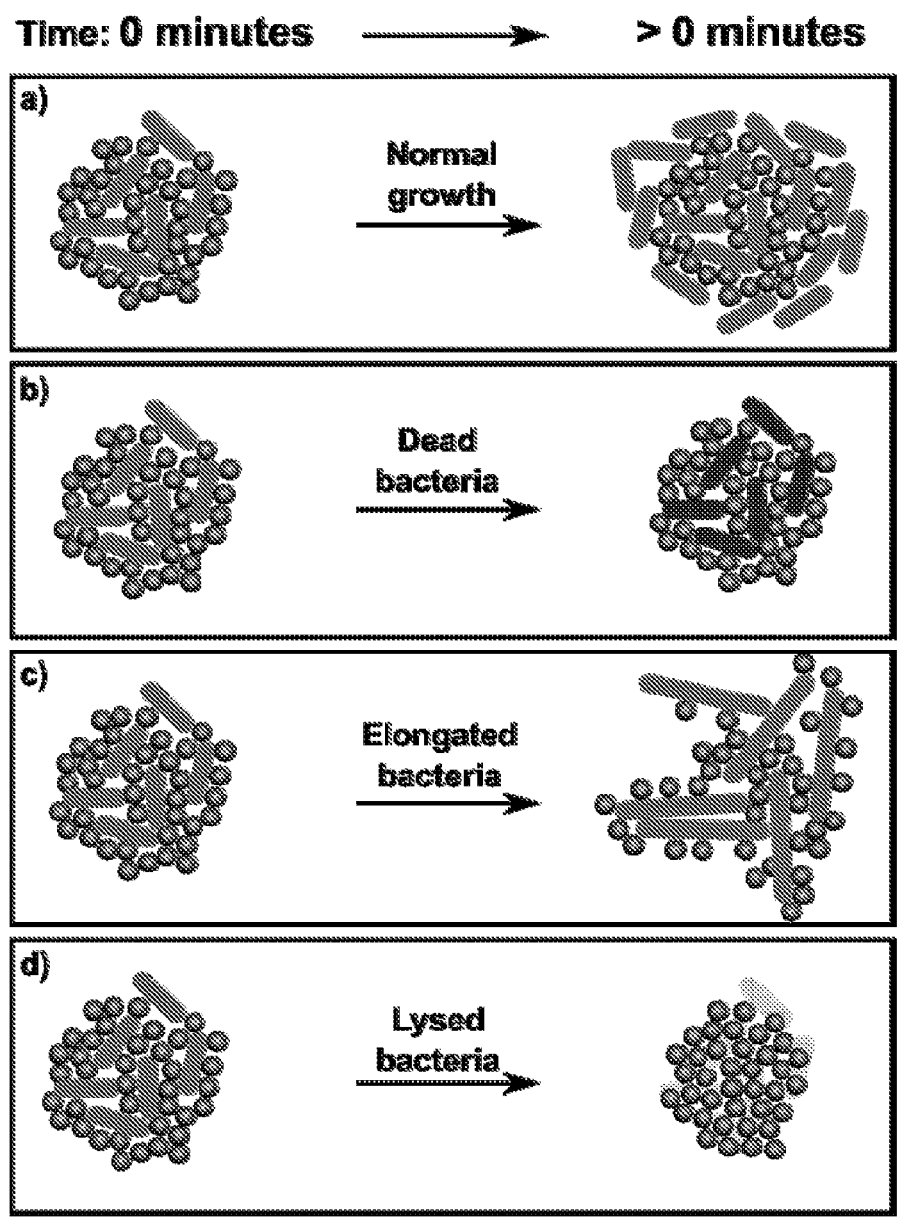
FIG. 18 a-d

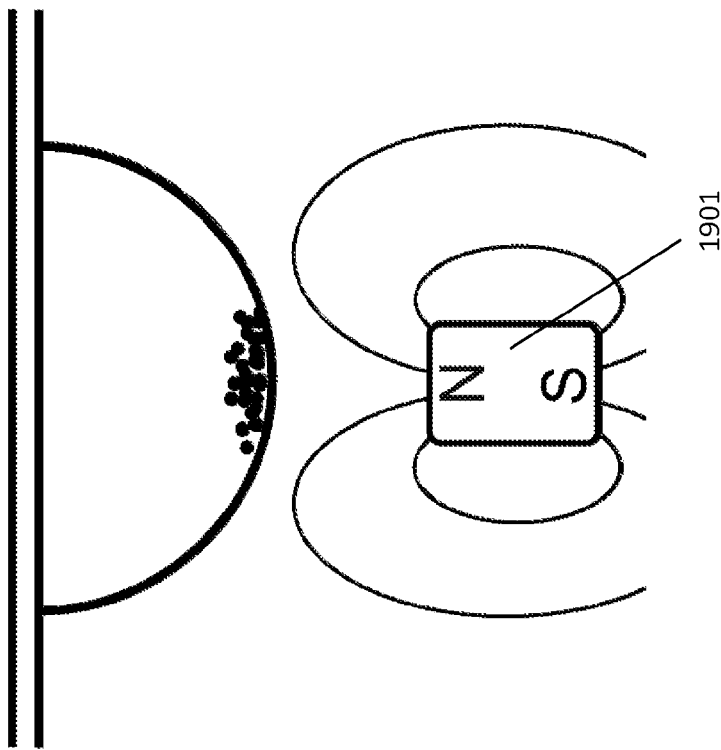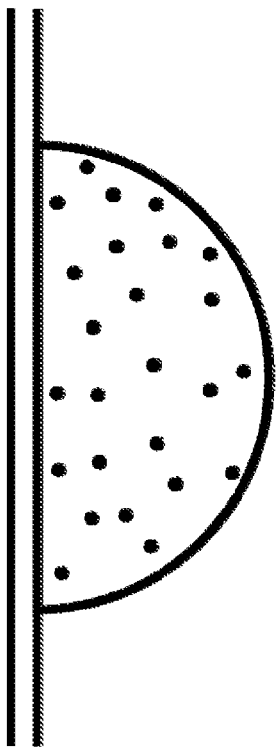

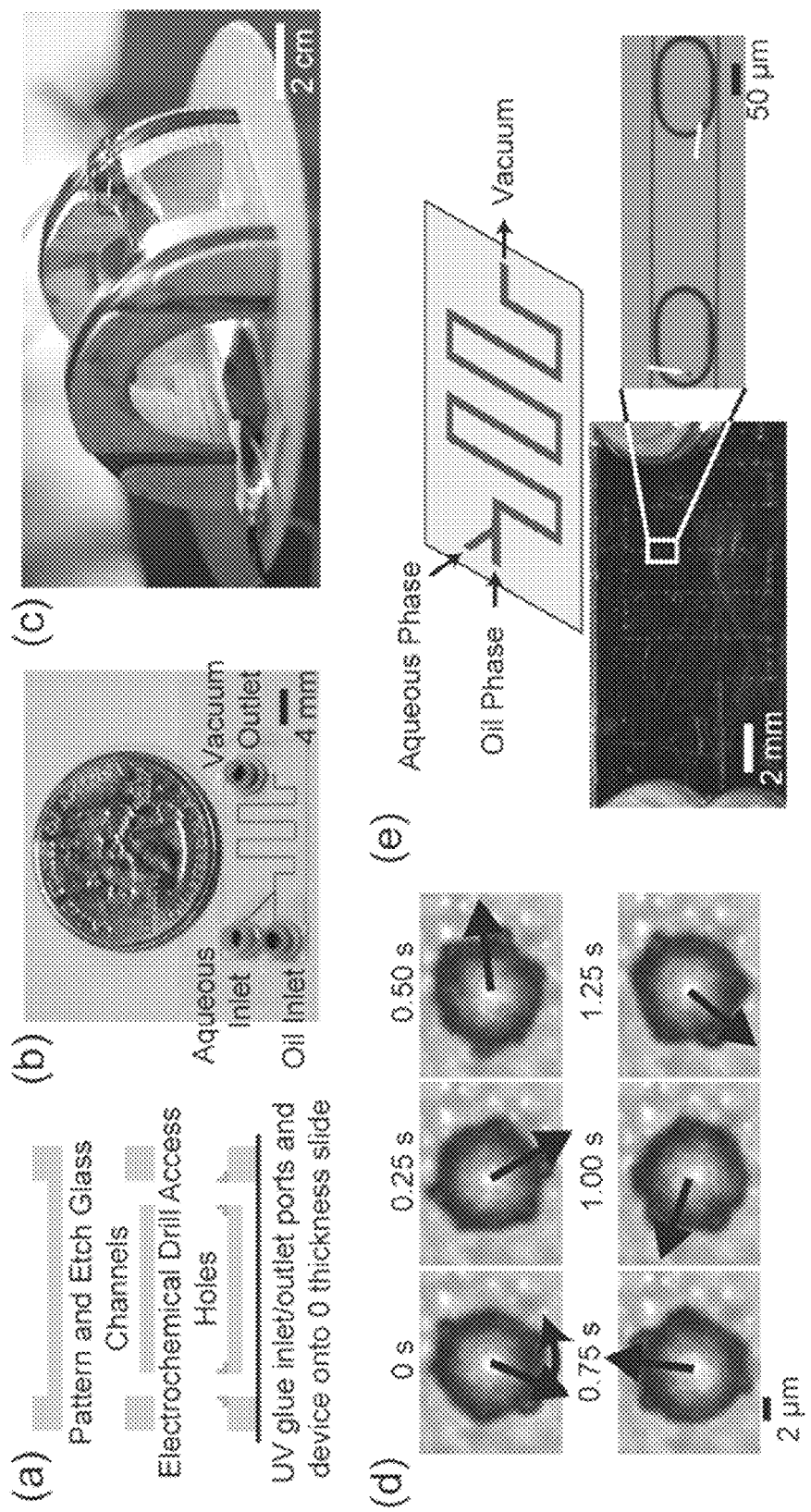
FIGS. 23a-e

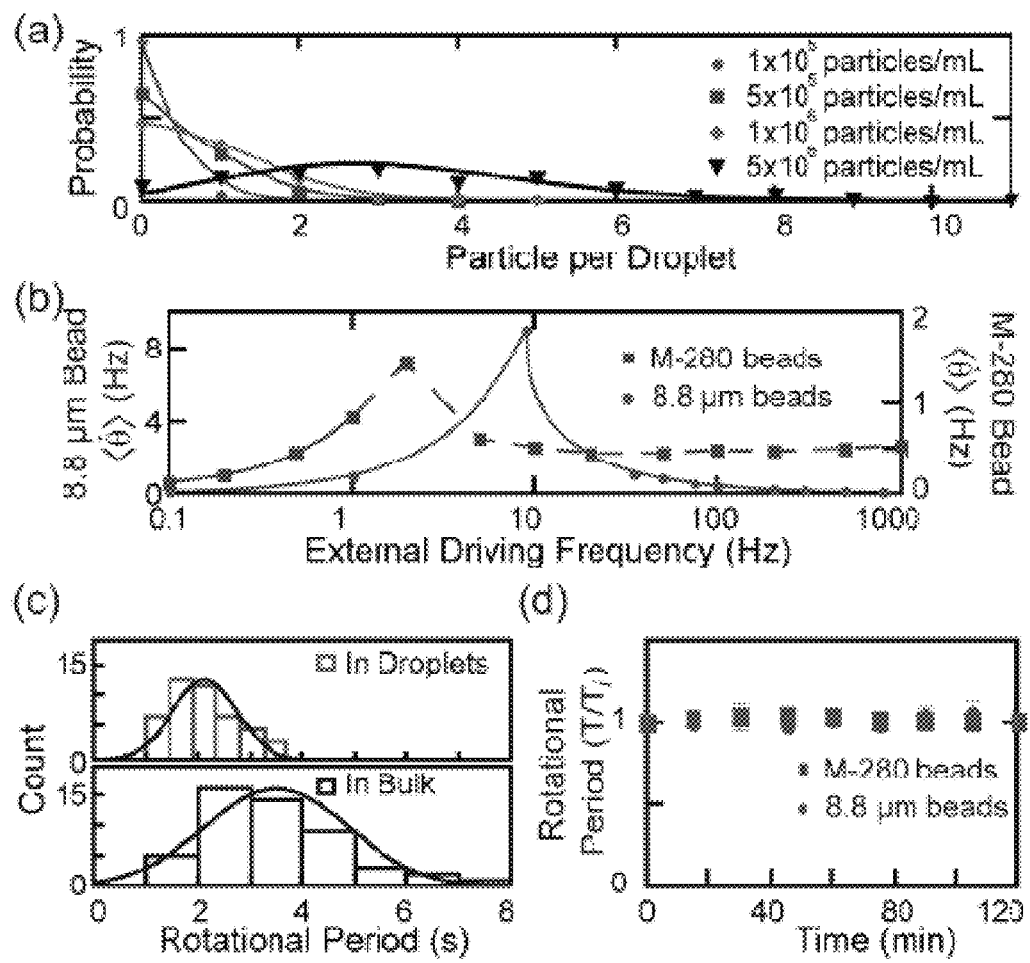
FIGS. 24a-d

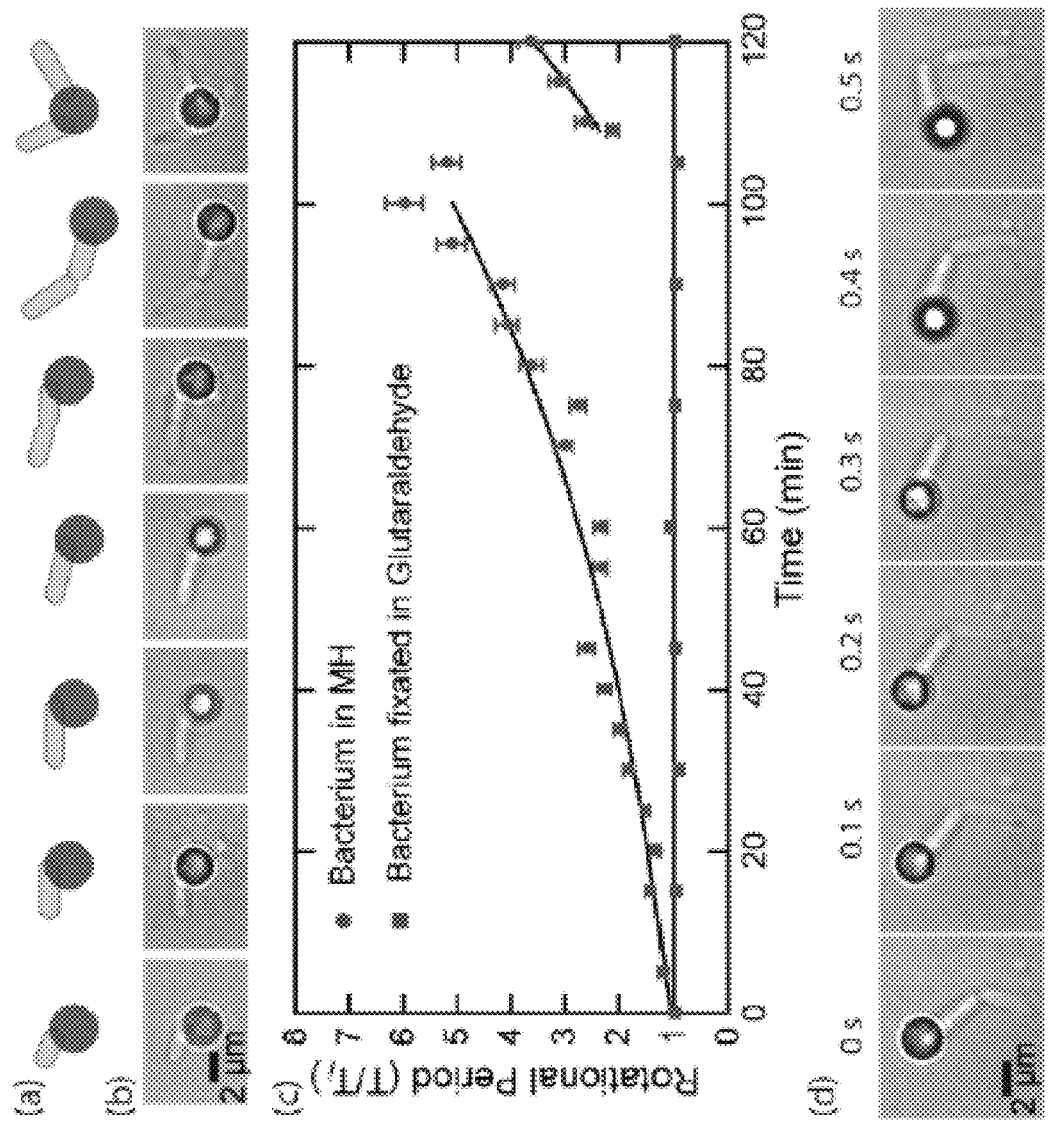
FIGS. 25A-d

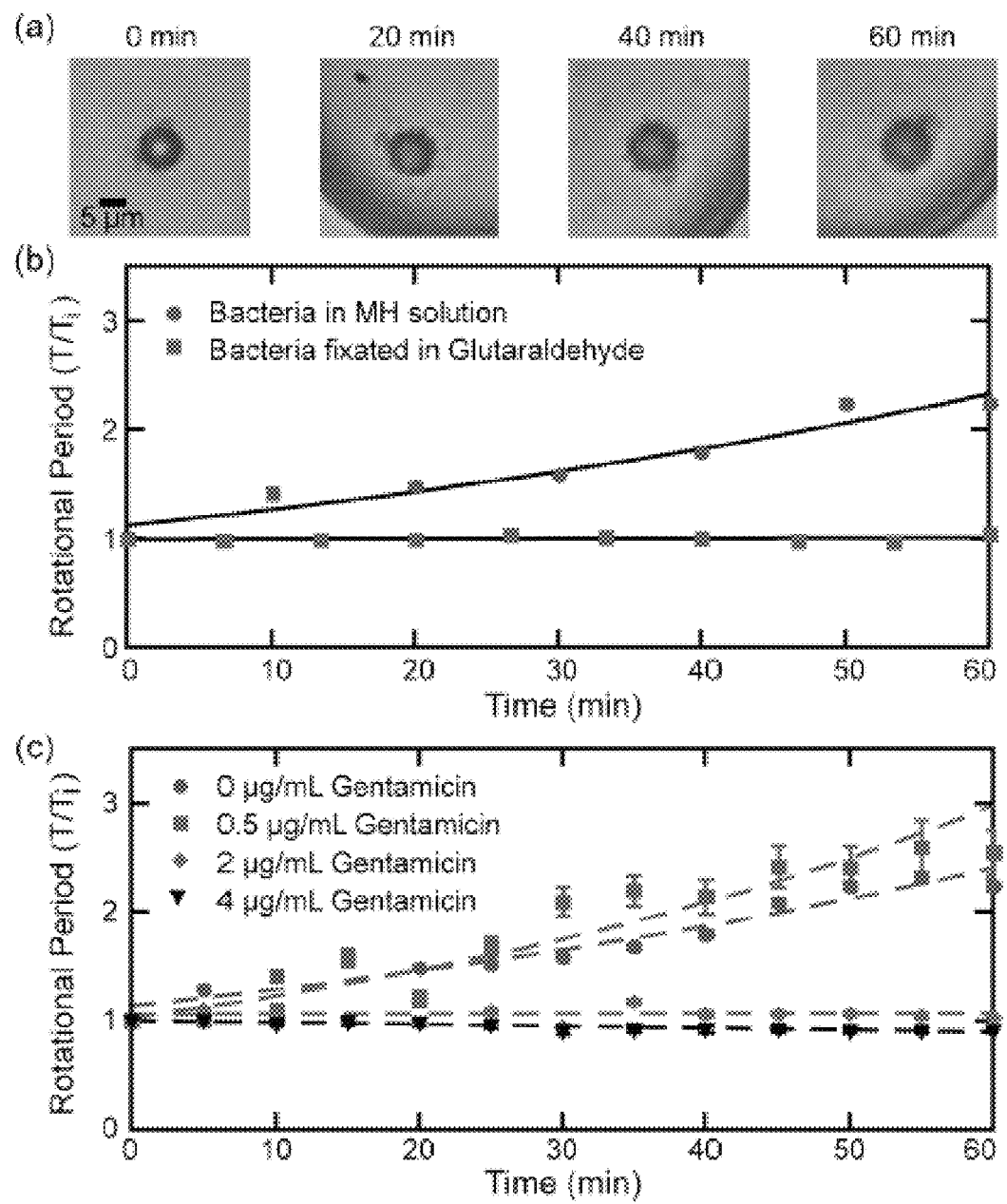
FIGS. 26a-c

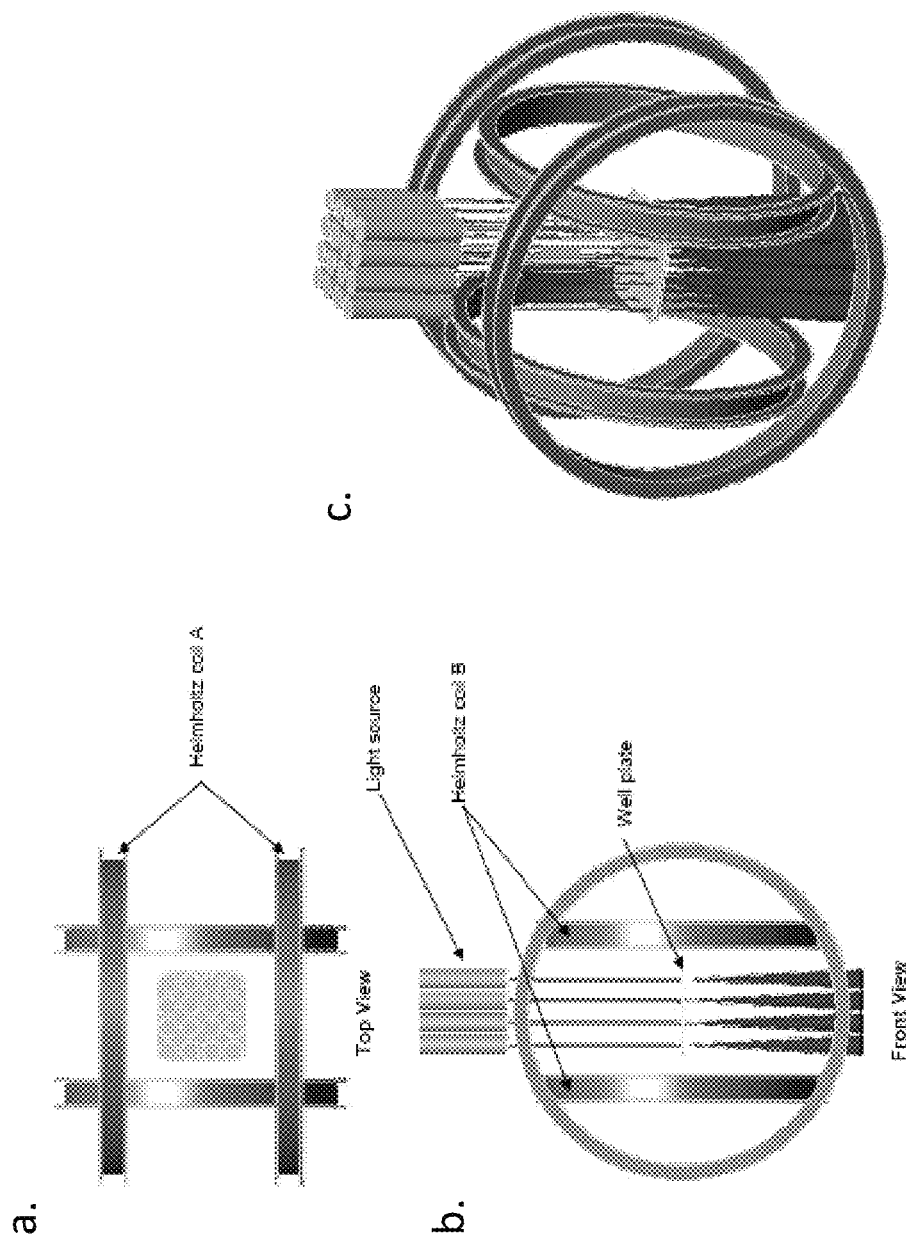
FIG. 32a-c

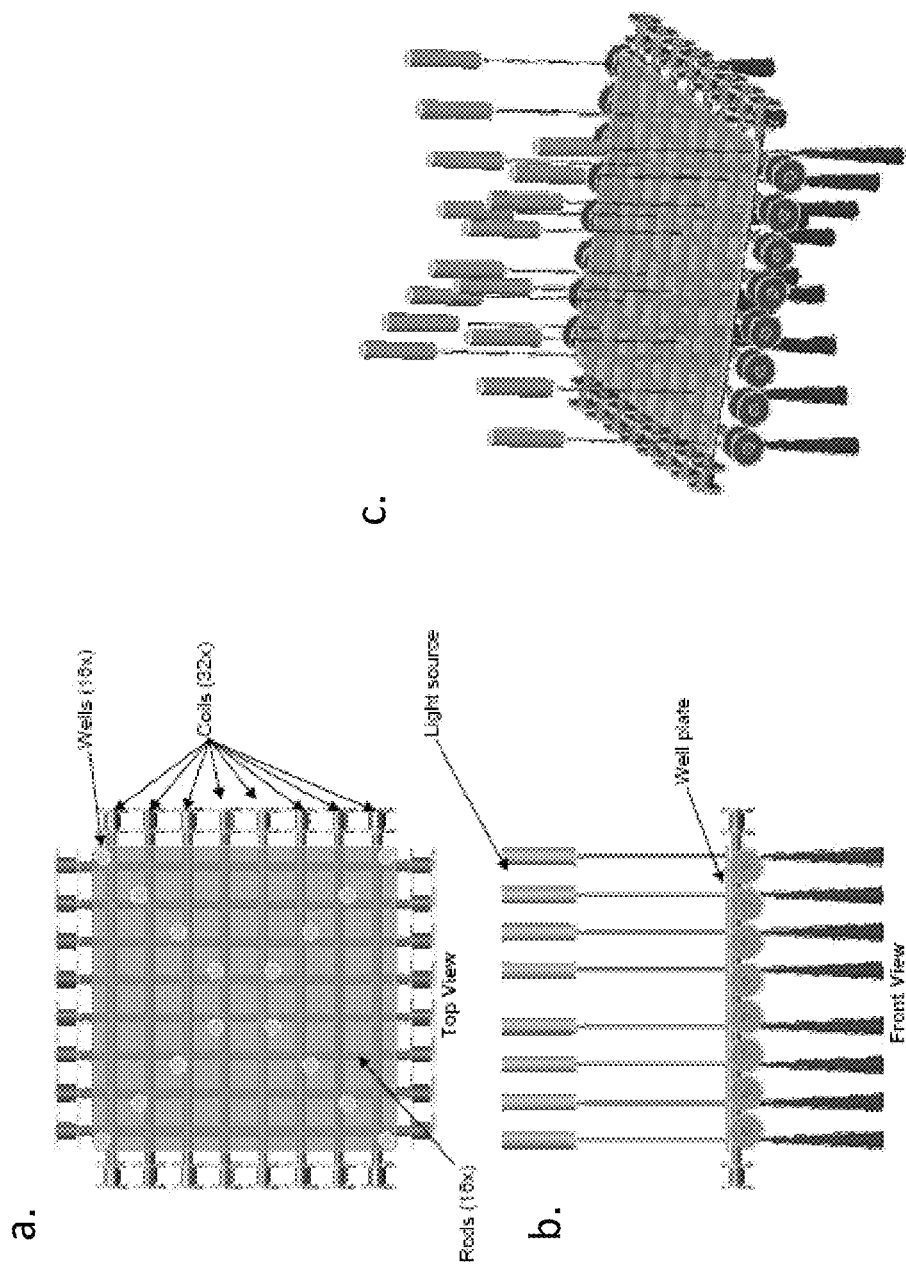
FIG. 33a-c

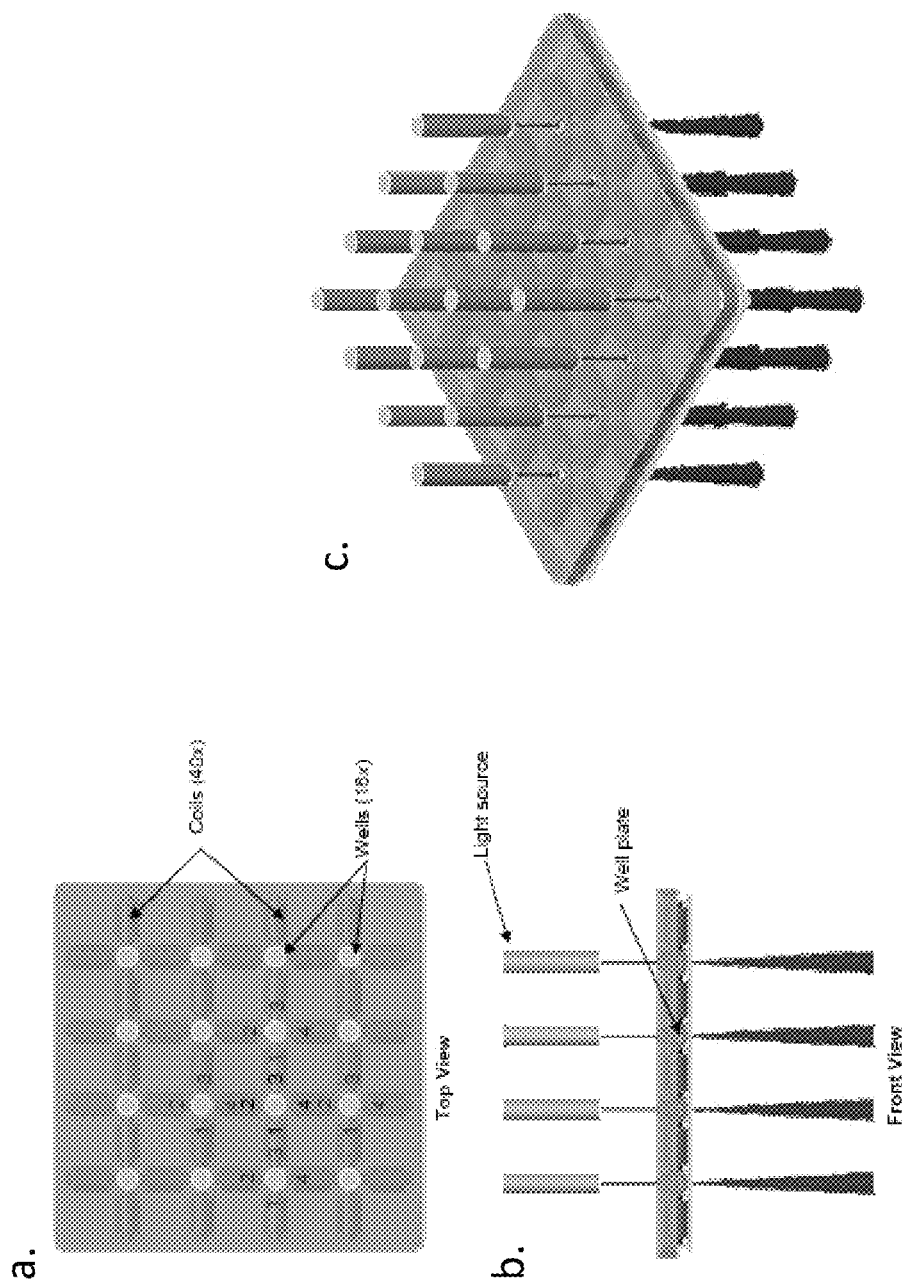
FIG. 34a-c

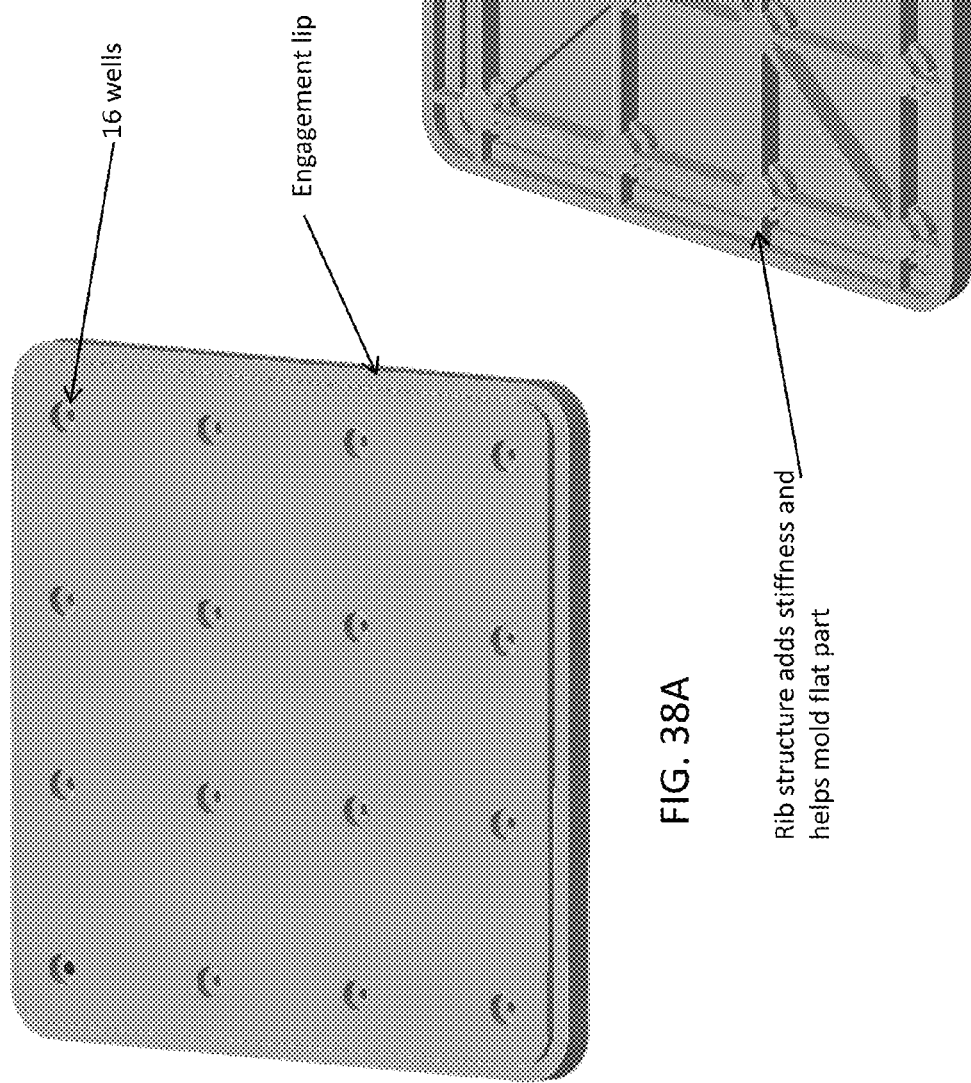

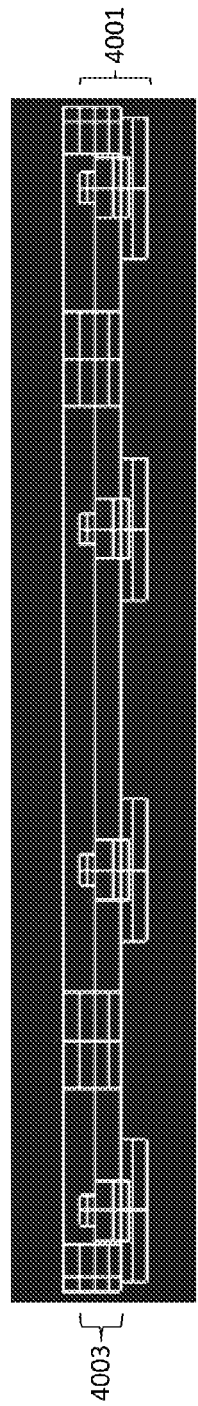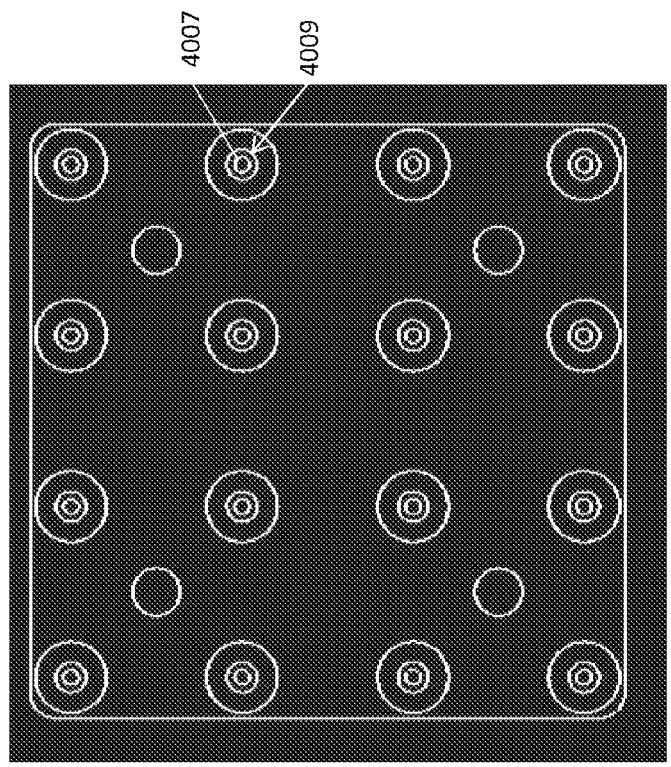
FIG. 40A
FIG. 40B

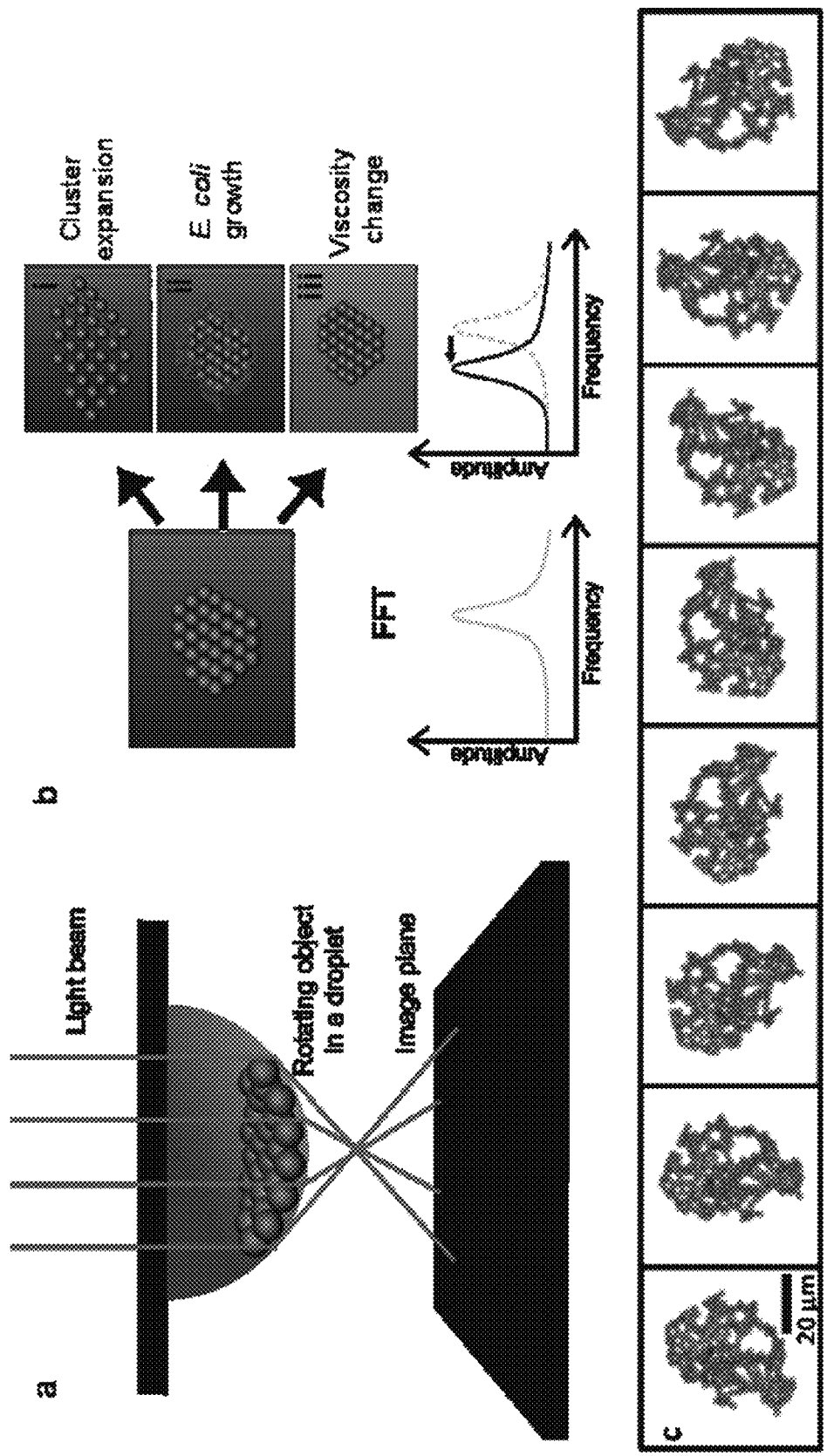
FIG. 46a-c

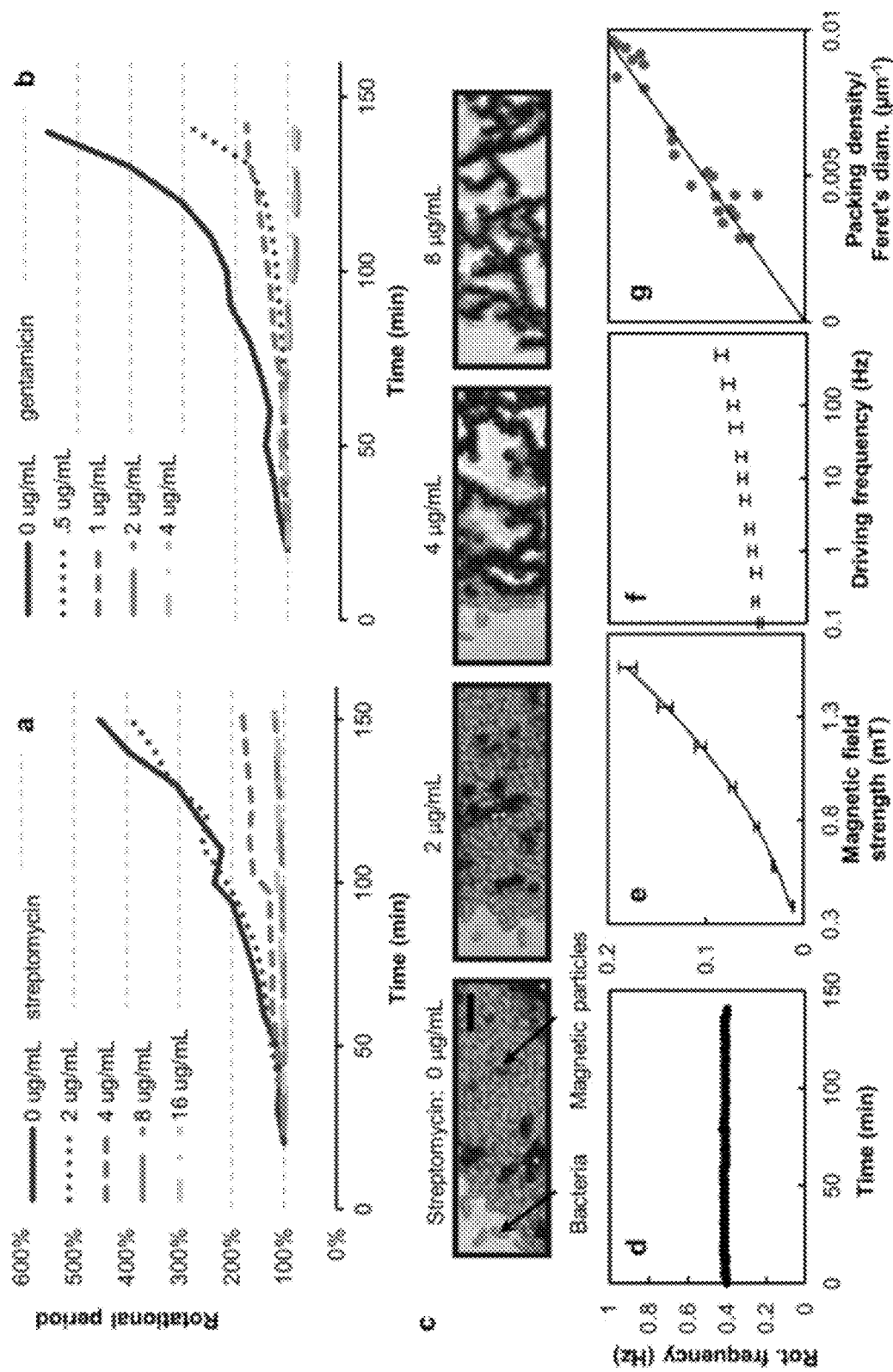
FIG. 47a-g

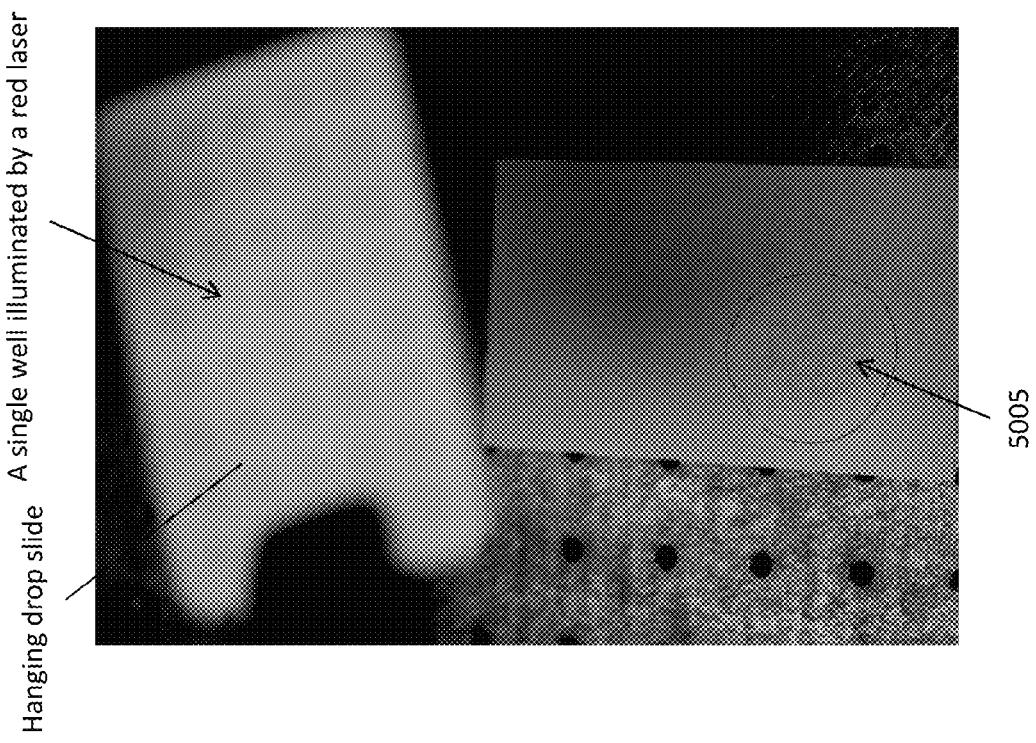
FIG. 50C  A single well illuminated by a red laser
Hanging drop slide
5005
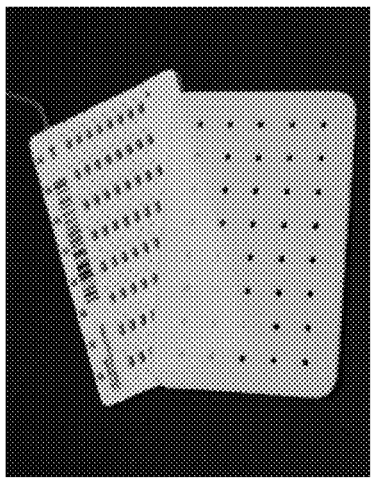
FIG. 50A
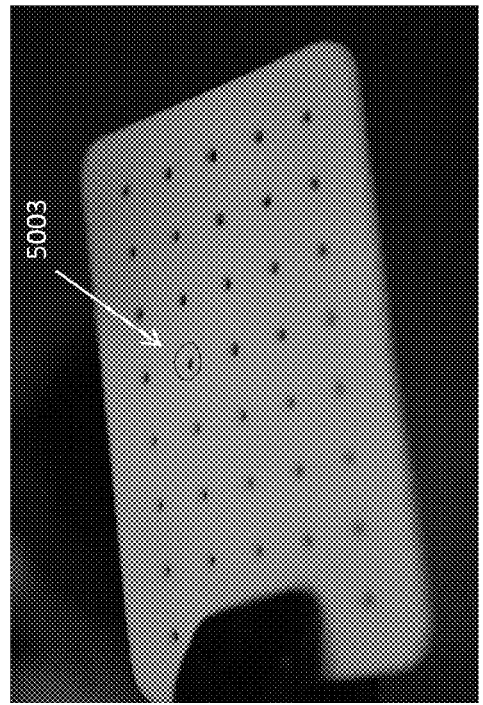
FIG. 50B
5003

ASYNCHRONOUS MAGNETIC BEAD ROTATION SENSING SYSTEMS AND METHODS

CROSS REFERENCE TO RELATED APPLICATIONS

This patent application claims priority to each of: U.S. provisional patent application Ser. No. 61/402,310, filed on Aug. 27, 2010 and titled "Multi-Well Reader Device, Disposable Card, and Method for Asynchronous Magnetic Bead Rotation Assays"; and to U.S. provisional patent application Ser. No. 61/474,123, filed on Apr. 11, 2011, and titled "Asynchronous Magnetic Bead Rotation Sensing Systems and Methods," which are both expressly incorporated herein in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

STATEMENT REGARDING FEDERALLY SPONSORED RESEARCH OR DEVELOPMENT

This invention was made with government support under DMR0455330 awarded by the National Science Foundation and EB009550 awarded by the National Institutes of Health. The government has certain rights in the invention.

BACKGROUND OF THE INVENTION

As reported by the U.S. Center for Disease Control (CDC), there are over 100,000 bacteria-related deaths per year in the United States alone. Of these infections, large percentages are caused by antibiotic-resistant microorganisms. Infections due to resistant organisms are occurring at higher frequencies and this increase in resistance is only worsened by the slowing pace of development of new antibiotic agents. Indeed, there has been a 53% decrease in FDA approved antibiotic agents between the years 1983 and 2002 (Spellberg, B, J H Powers, E P Brass, L G Miller, and J E Edwards, Jr., Trends in antimicrobial drug development: implications for the future, Clin. Infect. Dis. 38, 1279-1286, May 2004). With the number of available antibiotics decreasing, there is an ever increasing need to determine the most appropriate antibiotic therapy. In an attempt to preserve the effectiveness of available antibiotics, stewardship programs have also been implemented and their effectiveness studied (MacDougall, C. and R. E. Polk, Antimicrobial Stewardship Programs in Health Care Systems, Clinical Microbiology Reviews 18, 638-656, October 2005). Nonetheless, the compounded problem of emerging resistance and slowing development of new antibiotics has left many clinicians frustrated (Talbot, G H, J Bradley, J E Edwards, Jr., D Gilbert, M Scheld, and J G Bartlett, Bad Bugs Need Drugs: An Update on the Development Pipeline from the Antimicrobial Availability Task Force of the Infectious Diseases Society of America Clinical Infectious Diseases 42, 657-668, March 2006). While development of new antibiotics is one approach, it only addresses part of the problem. What it does not address is the need and role that rapid diagnostics have in appropriately managing antibiotics. In some cases, overexposure of bacteria can ultimately lead to pan-resistant organisms for which there are no currently available antibiotics that can be used for effective treatment (Boucher, H W, G H Talbot, J S Bradley, J E Edwards, Jr, D Gilbert, L B Rice, M Scheld, B Spellberg, and J Bartlett, Bad Bugs, No Drugs: No ESKAPE! An Update from the Infectious Diseases Society of America, Clin. Infect Dis 48, 1-12, January 2009). Even organisms that are not pan-resistant can be extremely harmful to patient populations and create a severe burden on the health system (Chu V H, Crosslin D R, Friedman J Y, et al., *Staphylococcus aureus* bacteremia in patients with prosthetic devices: costs and outcomes, Am J Med 118, 1416, December 2005). One such organism is methicillin-resistant *Staphylococcus aureus* (MRSA). MRSA-related infections can appear in many different forms, such as blood infections, skin infections, respiratory infections and others (Boucher H W, G R Corey, Epidemiology of methicillin-resistant *Staphylococcus aureus*, Clin. Infect Dis. 46, S344-9, June 2008). In the US, there are an estimated 19,000 MRSA-related deaths per year, which leads to more deaths in the US than HIV/AIDS and Tuberculosis combined (Klevens R M, J R Edwards, F C Tenover, L C McDonald, T Horan, R Gaynes, Changes in the epidemiology of methicillin-resistant *Staphylococcus aureus* in intensive care units in US hospitals, 1992-2003, Clin. Infect Dis 42, 389-91, February 2006; and Boucher H W, G R Corey, Epidemiology of methicillin-resistant *Staphylococcus aureus*, Clin. Infect Dis. 46, S344-9, June 2008). The number of MRSA cases per year has historically been rapidly increasing—in 2003, there were a reported 400,000 inpatient MRSA-related cases (Noskin G A, R J Rubin, J J Schentag et al., National trends in *Staphylococcus aureus* infection rates: impact on economic burden and mortality over a 6-year period (1998-2003), Clin. Infect Dis 45, 1132-40, November 2007). MRSA is now so common that in intensive care units (ICU) it accounts for more than 60% of *S. aureus* isolates (National Nosocomial Infections Surveillance (NNIS) System report, data summary from January 1992 through June 2004, issued October 2004, Am. J. Infect Control 32, 470-85, October 2004).

One method that has been commercialized to rapidly identify MRSA infections is molecular diagnostics. Identification of resistant microorganisms by the use of molecular diagnostics has shown tremendous progress and usefulness. In the case of MRSA, molecular tests are based on detection of the mecA gene in addition to a sequence that is specific to *S. aureus*. While molecular diagnostics provide rapid information that is useful for screening and even initial choice of antibiotic, it does not necessarily determine the ideal antibiotic, based on the minimum inhibitory concentration that ultimately determines the most appropriate antibiotic therapy. This key fact is true for many detection methods including impedance (Yang, L., Y. Li and G. F. Erf, Interdigitated array microelectrode-based electrochemical impedance immunosensor for detection of *Escherichia coli* O157:H7, Anal. Chem. 76, 1107-1113, 2004), quartz crystal microbalance (Su, X.-L. and Y. Li, A self-assembled monolayer-based piezoelectric immunosensor for rapid detection of *Escherichia coli* O157:H7, Biosens, Bioelectron. 19, 563-574, January 2004), bioluminescence (Fujinami, Y., M. Kataoka, K. Matsushita, H. Sekiguchi, T. Itoi, K. Tsuge and Y. Seto, Sensitive detection of bacteria and spores using a portable bioluminescence ATP measurement assay system distinguishing from white powder materials, J. Health Sci. 50, 126-132, 2004), plasmon resonance (Fratamico, P. M., T. P. Strobaugh, M. B. Medina and A. G. Gehring, Detection of *Escherichia coli* O157:H7 using a surface plasmon resonance biosensor, Biotechnol. Tech. 12, 571-576, July 1998), microcantilever sensors (Ilic, B., D. Czaplewski, H. G. Craighead, P. Neuzil, C. Campagnolo and C. Batt, Mechanical resonant immuno-specific biological detector, Appl. Phys. Lett. 77, 450-452, 2000), among others.

In order to determine the most appropriate antibiotic therapy, antibiotic susceptibility testing must be performed, where the minimum inhibitory concentration (MIC) is measured. The MIC information gleaned from MIC values can have a major impact on patient mortality. For example, in one study, mortality rates related to ventilator-associated pneumonia were reduced from 60.8% to 33.3% when antibiotics were initially properly administered (Kumar A, D Roberts D, Wood K E, et al. Duration of hypotension before initiation of effective antimicrobial therapy is the critical determinant of survival in human septic shock, Crit. Care Med 2006; 34:1589-96, 2006). To achieve optimum treatment, antibiotic susceptibility testing and reported MIC values must be performed. This is even the case when a rapid diagnostic has been used to determine resistance based on the mecA gene. For example, when the MIC value of a MRSA isolate is near or above 2 μg/mL, a therapeutic agent other than vancomycin (e.g. daptomycin or linezolid) should be implemented (Deresinski, S., Counterpoint: Vancomycin and *Staphylococcus aureus*—an antibiotic enters obsolescence. Clin. Infect Dis. 44, 1543, 2007; and Sakoulas, G, Moise-Broder, P A, Schentag, J, et al., Relationship of MIC and Bactericidal Activity to Efficacy of Vancomycin for Treatment of Methicillin-Resistant *Staphylococcus aureus* Bacteremia, J. Clin. Microbiol 42, 2398, 2004).

The emergence and spread of antibiotic resistance is a global health concern, as pathogenic species increasingly adapt to antimicrobial agents and classes. Standard antimicrobial susceptibility testing (AST) protocols typically take over 24 hours for a full analysis; as a result, patients are often prescribed empiric therapies prior to diagnosis. Incorrect empiric therapies, such as the inadequate, inappropriate, or overly broad-spectrum use of antimicrobial agents, result in poor patient response and contribute to the increase in multi-drug resistant pathogens. Decreasing the use of unnecessary antibiotics and treating patients with narrow-spectrum agents will help confront this global problem; one approach towards this goal is through the development of rapid AST for earlier diagnosis. Earlier diagnosis will enable more appropriate therapies to be prescribed, reduce antibiotic use, and may lead to more effective treatments. Subsequently, it will reduce health care costs, length of hospital stays, and the spread of antimicrobial resistance.

Traditional methods of microbial identification and differentiation of the infectious organisms rely on phenotypic characteristics, such as morphology and growth. However, molecular diagnostic techniques are increasingly used as adjuncts in clinical AST. These diagnostic techniques, in particular the polymerase chain reaction (PCR), enable rapid detection of pathogen-derived nucleic acids in clinical specimens, thereby reducing identification and diagnosis to a few hours. However, molecular methods are typically more expensive than phenotype-based assays, genetically identical bacteria may exhibit phenotypic heterogeneity potentially leading to inappropriate treatments, and only a few resistance genes have been firmly associated with phenotypic resistance. Ultimately, phenotype-based methods, specifically determining the minimum inhibitory concentration (MIC) of the bacterial species, remains the 'gold standard' for AST. Currently, rapid clinical AST measurement tools utilize the growth-based microdilution technique (incorporated by the various commercially available AST systems) to determine the MIC, which is defined as the lowest antibiotic concentration that inhibits visible growth after overnight incubation. Nevertheless, the complete AST protocol, from pathogen isolation to MIC determination, takes well over 24 hours due to the combination of long culture time (18-24 hours) and the AST measurement time (requiring 6-24 hours). Towards the goal of achieving faster AST measurements, there is a need for the improvement of optical detection methods and/or the development of new approaches to detect bacterial proliferation.

Microfluidic technologies have been used to reduce the turnaround time for AST. By confining single or small cell populations of bacteria in nanoliter volume droplets, the effective concentration of cells in a system increases. Furthermore, the droplet systems are not subjected to dilution effects that are apparent in bulk systems; as a result, cellular biochemical signals or reaction products accumulate in the droplet more rapidly. Using a microfluidic droplet system, the MIC values for *Staphylococcus aureus* cells that were exposed to antibiotics were obtained within 7 hours by measuring the accumulation of a fluorescence viability indicator. Another microfluidic approach confines cells in gas-permeable microchannels with high surface-to-volume ratios, which increases oxygen diffusion into the system. Increased levels of oxygen available to the cells resulted in faster replication rates and bacterial cells accumulated in the channels more rapidly. *Escherichia coli* (*E. coli*) bacteria exposed to antibiotics were cultivated in these high surface-to-volume microfluidic channels, allowing AST measurements based on the turbidity of the sample to be obtained within 2 hours from the start of cultivation.

There is also a need for detection of bacterial/microbial contamination of food, including particularly agricultural food testing. Accurate methods for detecting and identifying diverse groups of pathogenic bacteria are essential for protecting the public from foodborne bacteria.

Recently, asynchronous magnetic bead rotation (AMBR) has been applied towards bio-sensing applications, such as bacterial cell and analyte detection. See, e.g., U.S. Publication No. 2008/0220411 to McNaughton et al. The AMBR biosensors are based on a technique in which a magnetic bead is placed within an external rotating magnetic field and changes in this magnetic bead's physical properties (i.e. shape and volume), or changes in its environment, translate into detectable changes in the bead's rotation rate. For instance, when a viable cell that is attached to a magnetic bead grows, the rotation rate of an asynchronously rotating magnetic bead may decrease. However, under bulk experimental conditions, AMBR biosensors can be subjected to bead translation, magnetic interactions (if the sample is not sufficiently dilute), surface adhesion and stiction effects, which may reduce the efficiency or accuracy of the system. Further, although it is desirable to optically monitor the rotation rate of the magnetic bead(s); although larger beads may be more readily visualized, it would be helpful to enhance the visualization of even small magnetic particles used as probes.

Thus, there is a need for AMBR-based systems that allow for determination of bacterial growth and binding in a manner that avoids many of the issues discussed above. In addition, it would be beneficial to allow parallel testing of a plurality of rotating magnetic bead assays. Other improvements to the existing AMBR systems may address the design of the sensing apparatus, including the camera or visualization system, controlling the formation of aggregates of magnetic beads for monitoring cell growth, sorting of magnetic particles prior or during AMBR (e.g., to separate those with bound cells from those that are unbound), preparation of coated beads having appropriate buoyancy, detection of cell growth even when the system is not rotating the magnetic beads, detection of bacteria in a blood sample directly, enhancing or speeding-up bacterial growth in combination with AMBR, and droplet-based microfluidic platforms that use AMBR biosensors for rapid growth studies at the single cell and small cell-population level.

The variations of the AMBR biosensors, systems and methods described herein may be used in any combination or sub-combination. At the single cell level, heterogeneity studies or single cell kinetics studies become possible due to the high sensitivity of these improved systems. For clinical AST, studies of collective cellular behavior are desired since cells act in a cooperative manner to provide protection, improve survival against competitors and initiate quorum sensing. Towards this end, the AMBR systems described herein may allow rapid measurement of changes in cell growth in response to external factors, and offer improvements over currently existing biosensors, including previously described AMBR sensors.

SUMMARY OF THE INVENTION

Described herein are techniques that allow for sensitive and rapid measurement of bacterial growth. The method and techniques described herein may solve many of the problems mentioned above. The present techniques are capable of measuring the growth of a small number of bacterial cells, including single cell sensitivity. Application of the techniques described herein may enhance the determination of antimicrobial therapies, which will not only reduce antimicrobial resistance, but may also save lives. These techniques may also be applied to enhancing food safety. The improved AMBR techniques described herein may also be used for optimizing drug therapies, including optimization of chemotherapies for personalized treatment of cancers.

For example, the techniques taught herein may allow for MIC values to be obtained in hours instead of days (from clinical specimen). Although other approaches to accomplish this have been under development, such as microcantilevers (Gfeller K Y, N Nugaeva, M. Hegner, Micromechanical oscillators as rapid biosensor for the detection of active growth of *Escherichia coli*, Biosens Bioelectron 21, 528-533, 2005; and Godin M, F F Delgado, S Son, W H Grover, A K Bryan, A Tzur, P Jorgensen, K Payer, A D Grossman, M W Kirschner, S R Manalis, Using buoyant mass to measure the growth of single cells, Nat. Methods, 2010 7, 387-90, 2010), two-photon excitation (Koskinen J O. T Stenholm, J Vaarno, J Soukka, et. al. Development of a rapid assay methodology for antimicrobial susceptibility testing of *Staphylococcus aureus*, Diagn. Microbiol Infect. Dis. 3, 306-316, 2008), and impedance sensors (Varshney M, Y. Li, Interdigitated array microelectrodes based impedance biosensors for detection of bacterial cells, Biosens Bioelectron 15, 2951-60, 2009), the techniques described herein offer numerous advantages over previously reported methods. For example, the present techniques can utilize inexpensive off the shelf components that can be placed on printed circuit boards, can take advantage of magnetic beads and because of this, can be easily automated as has been done by a large amount of in vitro diagnostic products (e.g. MagNA Pure from ROCHE), and can have a detection limit on the single cell level.

There are multiple benefits to reducing the MIC time, including a dramatic improvements in patient outcome and reductions in costs to the health care system. As mentioned, the techniques and method described herein may be referred to as "asynchronous magnetic bead rotation" (AMBR), and modifications or improvements thereof. This name is used as a matter of convenient reference and not of limitation.

AMBR is an emerging biosensor platform, which is based on the rotational dynamics of magnetic particles in rotating magnetic field, placed in a fluidic environment. The rotation rate of a magnetic body depends on variables such as its volume and magnetic moment, and fluid viscosity. Using these relationships it is possible to use magnetic particles as extremely sensitive biosensors, called AMBR sensors. The systems, applications, improvements and methods for AMBR sensors described herein offer substantial improvements and modifications of previously described AMBR systems.

Thus, described by example herein are devices, systems and method for monitoring cell growth, including (but not limited to) bacterial cell growth. In particular, described herein are methods and systems for performing antibiotic susceptibility testing, and methods of determining and/or identifying bacterial contamination or infection. The systems described herein may allow for parallel testing or processing of samples in a small and cost-effective footprint, including multiwell plates configured to allow parallel testing of cell populations. The plates may be used as part of an automated (or semi-automated) reader system that is configured to permit and allow cell growth. The plates or sampling chamber may also be configured to enhance visualization or optical sampling of the rotational rate of magnetic beads, and particularly aggregates of magnetic beads while permitting cell growth and division.

For example, the methods, devices and systems for performing asynchronous magnetic bead rotation may include features allowing for control of the optics (including both illumination, visualization and analysis of rotation), control of the sample size (e.g., well size, or droplet size), control of the sensing modality (including a static observation mode), control of clustering or aggregation of the magnetic beads, and control of the magnetic beads themselves. The description may be divided up into the sections listed below, however it should be understood that the features, methods or techniques described in any of these sections may be incorporated or combined with any of the other methods, techniques or features (including systems) described in any other section, entirely or in part.

The method, devices and systems described herein are particularly useful for adapting and improving AMBR so that it can be performed rapidly and robustly. Thus, many of the improvements described herein include modifications that allow multiple assays may be performed in parallel, and improving the ability to detect rotation of magnetic particles. For example, described herein are features which allow robust multiwell processing, which has previously been difficult or impossible to achieve.

In particular, described herein are AMBR techniques in which relatively large (e.g., more than about 5 magnetic particles, more than about 10 magnetic particles, more than about 100 magnetic particles, etc.) clusters of magnetic particles are formed either before or after binding of cells, and the cluster(s) of cells are rotated to perform the AMBR assay. The use of one or more large rotating clusters within a testing well may improve detection (as the size of the cluster makes rotation easier to detect) and may enhance sensitivity. The cluster may be formed at an interface (e.g., fluidic interface) and the interface may be configured to help form and maintain the cluster and may also help control the position of the cluster. For example, the interface may be a curved interface, which may include a curved well bottom, a hanging droplet, an oil-water interface, or the like. The shape of the well may also be configured to lens, or magnify, the image of any rotating magnetic particles (including clusters) within the well. For example, the shape of the well may include a curved interface that acts as a lens to magnify images of the rotating magnetic particles within the well so that it can be readily detected by an imaging surface of an imaging sensor.

For example, described herein are methods of monitoring cell growth and/or binding by asynchronous magnetic bead rotation (AMBR) in a cluster of magnetic particles, the method comprising: allowing cells to bind to magnetic particles; forming a cluster of the magnetic particles; applying a rotating magnetic field at a driving rate so that the magnetic particles rotate asynchronously to the applied magnetic field at an asynchronous rotation rate; and detecting a change in the asynchronous rotation rate indicative of cellular binding and/or growth in the cells.

The clusters may be formed by magnetic interaction between the magnetic particles. For example, forming the cluster may comprise forcing a low interparticle distance, allowing the particles to magnetically interact. In some variations, clusters may be formed by applying a magnetic field to drive the magnetic particles together (allowing closer proximity); for example, the rotating magnetic field may initially be applied at a higher rate or intensity (e.g., 10× the "normal" rotating magnetic field intensity or rate of rotation) to enhance clustering.

In some variations, the cells may be added to the magnetic particles to allow them to bind. Cells (e.g., prokaryotic cells, eukaryotic cells, etc.) may bind to the magnetic particles specifically or non-specifically; for example, cells may bind to the magnetic particles which have been functionalized by a specific antibody to bind to the target cells. Binding may occur by simply adding the magnetic particles (e.g., beads) to a solution including the target cells. After binding, the magnetic particles (which may include bound cells) may be magnetically sorted or purified from the rest of the sample. For example, the magnetic particles may be magnetically pulled from the mixing solution, or they may be magnetically immobilized and rinsed, or some combination of these steps. Magnetic purification may also assist in forming clusters of magnetic particles. Thus, any of the methods described herein may include the step of magnetically separating the magnetic particles from a sample containing the cells.

A cluster of magnetic particles may be held by gravitational forces at an interface (e.g., liquid-air, liquid-liquid, and/or liquid-solid interfaces). Thus, the magnetic particles may be more or less buoyant compared to the media in which they are rotated. As mentioned, the well or chamber in which the particles (or cluster) are rotated may also be configured to help keep the particles in a particular location, which may make it easier to detect the particles rotation.

The shape of the cluster may also be controlled. For example, a cluster of magnetic particles may be formed into a planar (e.g., substantially flat) surface. Other geometries of clusters may be globular and linear and may be affected by the bound analyte, including (but not limited to) cells. In general, the overall shape of the cluster may also affect the rotational rate. Thus larger clusters typically rotate more slowly than smaller clusters during asynchronous rotation. The same number of magnetic particles may form different shapes when clustered, and these shapes may be influences by the bound analyte. Thus, the effects of binding and growth may exaggerate the AMBR effect.

As mentioned, the target cells may be added to the magnetic particles either before or after the particles have been clustered. For example, allowing the cells to bind the magnetic particles may comprise combing the magnetic particles and cells before the magnetic particles are clustered.

In general, large clusters of magnetic particles (e.g., >5, >10, >20, >50, >100, >200, >500, etc. magnetic particles per cluster) may be formed. For example, the step of forming a cluster of magnetic particles may include forming a cluster of between about 10 and about 10,000 particles. In some instances, where nanoparticles are used, cluster sizes may be much higher. Any appropriate size of magnetic particle (or mixture of sizes or range of sizes). For example, magnetic particles may be sized between 100 nm and 10 μm (e.g., 1 μm), or larger.

Any appropriate rotating magnetic field may be applied to drive rotation of the cluster of magnetic particles. In general, the driving rotating magnetic field is sufficient to drive rotation of the cluster of magnetic particles so that the cluster rotates asynchronously relative to the driving rotating magnetic field. As described in greater detail below, when the cluster of magnetic particles are rotating asynchronously with the driving magnetic field, cell growth (or additional binding) can be detected as a change in the asynchronous rotation rate.

In some variations the driving magnetic field is a circular rotating magnetic field. For example, the step of applying a rotating magnetic field may comprise applying a rotating magnetic field of constant amplitude. The rotational rate of the driving magnetic field is typically constant for a particular well.

The methods, devices and system described herein may be used to test for any appropriate cell type, including mixtures of different cells. For example, the target cells being examined may be prokaryotic (e.g., bacterial) cells, or eukaryotic (including human cancer) cells. Plant cells, yeast cells, fungal cells, or the like may also be tested as described herein.

Also described herein are integrated and automated systems for monitoring asynchronous magnetic bead rotation to determine cell binding and/or growth. These systems may include: a sample chamber configured to hold a multiwell sample plate; a driving magnetic field source configured to apply a rotating magnetic field to drive asynchronous rotation of magnetic particles within a plurality of wells of a multiwell sample plate within the sample chamber; and an optical detector configured to optically detect rotation of magnetic particles from a plurality of wells of a multiwell sample plate within the sample chamber.

In general, any of the systems described herein may be configured to sustain the cells, either by including incubation (e.g., temperature, humidity, gas mixture, etc. regulation), or by being configured for use in an incubator. Thus, in some variations the system includes an AMBR station or module to receive the samples to be rotated; this module typically includes the sample chamber, driving magnetic field source(s), and optical detector(s). The AMBR station/module may be configured to include incubation by regulating temperature, humidity and/or gas mixture as appropriate for the target cells. Alternatively, the AMBR station/module may be configured for use within an incubator; for example, the module may include openings to allow humidified air to reach the cells from the incubator, and may be adapted for use at the humilities and temperatures within the incubator. In some variations the AMBR station/module may be surrounded or partially surrounded by a housing.

The systems described herein may also include an analyzer module to receive information from the optical sensor and to analyze this information. In some variations the system may include an analyzer that is integrated with the optical sensor; in other variations the analyzer is partially integrated and partially separated from the optical sensor, or completely separated from the optical sensor. For example, the system may include a processor coupled to the optical detector and configured to determine rotational frequency information on the rotation of magnetic particles of a plurality of wells of a multiwell sample plate within the sample chamber. Thus, an analyzer module may include a processor. The optical sensor an analyzer may be directly or indirectly (e.g., wirelessly) coupled.

In some variations the systems described herein include a multiwell sample plate. The sample plate typically includes a plurality of wells into which the magnetic particles and bound cells may be held. The arrangement of wells may be complimentary to the optical sensor and/or driving magnetic field source, so that the magnetic field driver(s) may apply the rotating magnetic field to one or more (or specific individual) wells of the plate, and the optical sensor may detect rotation of the magnetic particles, or cluster of magnetic particles, within one or more of the wells of the plate. Described below are various types of multiwell plates that may be adapted for use with the systems herein, including hanging droplet plates and curved bottom plates, as well as oil-droplet plates. In some variations these plates are disposable multiwell sample plates.

Any appropriate driving magnetic field source may be used. An appropriate driving magnetic field source is typically configured to apply a rotating magnetic field to one or more (or all) of the wells of the multiwell plate. In some variations this is achieved by rotating a magnetic source; in some variations multiple magnetic sources are positioned around the plate (or around individual wells of the plate) and sequentially activated to create a rotating magnetic field as seen by the magnetic particles in the plate. For example, the driving magnetic field source may comprise a plurality of inductors. These inductors may be arranged around either the entire plate, to apply a single rotating magnetic field to all of the wells, or around individual well or groups of wells, allowing separate control of the rotating magnetic fields applied to individual or sub-sets of wells in a plate. Thus, a plurality of inductors may be configured to be separately controlled so that various sub-combinations of inductors may be controlled to separately apply rotating magnetic fields to a subset of the plurality of wells. A driving magnetic field source may therefore include a plurality of inductors configured to generate a plurality of rotating magnetic fields driving asynchronous rotation of magnetic particles within different wells of a multiwell sample plate within the sample chamber.

The applied driving magnetic field may be rotated in any appropriate orientation so that the rotating magnetic particles (or clusters) may be optimally detected by the optical sensor. For example, a driving magnetic field source may be configured to apply a rotating magnetic field in a plane that is parallel to a multiwell plate within the sample chamber; this arrangement may be particularly helpful when the imaging sub-system (e.g., optical detector/sensor) is arranged to image down through the well, e.g., perpendicular to the plane of rotation. In some variations the driving magnetic field may be rotated perpendicular to the plane of the sample chamber. In some variations out-of-plane rotation may be used, which may result in a processing field.

Any appropriate optical detector (or detector) may be used. For example, the optical detector may include a CCD imaging device, or other direct-imaging device, having an imaging surface onto which the image of the rotating cells may be formed. The optical detector may also include a light source (or sources); any appropriate light source may be used, including LED light sources, laser light sources, or the like. Thus coherent or non-coherent light may be used. In addition, the light may be collimated or un-collimated. An optical detector may be configured to image through a curved interface on a multiwell sample plate so that the curved interface of the multiwell sample plate lenses light passing through a well of the multiwell sample plate onto the optical detector to magnify an image of rotating magnetic particles within the well. The light may be directed perpendicular to the rotating magnetic particles, or it may be directed at a non-zero incident angle (e.g., between −30 and 30 degrees, etc.).

In general the systems described herein are integrated systems which may observe (in parallel) multiple sample wells. These systems may also be automated to allow minimal user control; the user may simply add the plate into the sample chamber after loading the magnetic particles with bound cells, and allow it to run for the desired sample time (e.g., 2-12 hours, 4-8 hours, etc.). Results may be automatically displayed and/or transmitted and/or stored for review by the user. Data from the system may be calculated (e.g., by a processor), and/or graphs, curves, or other simplified representations may be generated, stored and/or displayed. In some variations the system may include one or more alerts, alarms, indicators or the like to indicate both the status of the system and/or the ongoing results of the assay.

Also described herein are integrated and automated system for monitoring asynchronous magnetic bead rotation to determine cell binding and/or growth, the system comprising: a sample chamber configured to hold a multiwell sample plate wherein individual wells of the multiwell sample plate have curved interfaces; a driving magnetic field source configured to apply a rotating magnetic field to drive asynchronous rotation of magnetic particles within wells of a multiwell sample plate within the sample chamber; and an optical detector configured to optically detect rotation of magnetic particles from light lensed though a curved interface of a well of a multiwell sample plate within the sample chamber.

As mentioned above, any of the systems described herein may be configured for (and may include) a multiwell sample plate wherein each well of the multiwell sample plate comprises a curved interface through which light may be lensed onto a sensing surface of the optical detector. These wells of the sample plate may include a curved surface (e.g., a curved fluidic surface) that may be sized and shaped to lens the light passing through the well, and/or size and shaped to position and/or orient the magnetic beads (e.g., cluster of magnetic beads) within the well. In some variations the multiwell sample plate comprises hanging droplet wells.

Any of these systems may also include a processor coupled to (or integrated with) the optical detector and configured to determine rotational frequency information on magnetic particles within a plurality of wells of a multiwell sample plate within the sample chamber.

Also described herein are integrated and automated systems for monitoring asynchronous magnetic bead rotation to determine cell binding and/or growth, the system comprising: a sample chamber configured to hold a multiwell sample plate wherein individual wells of the multiwell sample plate have curved interfaces; a driving magnetic field source comprising a plurality of inductors arranged to apply a plurality of rotating magnetic fields to drive asynchronous rotation of magnetic particles within wells of a multiwell sample plate within the sample chamber; an optical detector configured to optically detect rotation of magnetic particles from light lensed though a curved interface of a well of a multiwell sample plate within the sample chamber, wherein the lensing magnifies an image of magnetic particles within the well; and a processor receiving information from the optical detector and configured to determine frequency information on the rotation of magnetic particles within a plurality of wells of a multiwell sample plate within the sample chamber.

Also described herein are methods of monitoring cell growth and/or binding by asynchronous magnetic bead rotation (AMBR) of magnetic particles within a well having a curved interface, the method comprising: passing light through a well having a curved interface, the well containing at least one magnetic particle bound to an analyte, wherein the curved interface is positioned opposite of an image plane of an optical detector; applying a rotating magnetic field at a driving rate so that the magnetic particle rotates asynchronously with the applied magnetic field at an asynchronous rotation rate; and optically detecting light passing through the well that is lensed on an imaging surface by the curved interface to detect a change in the asynchronous rotation rate of the magnetic particles indicative of cellular binding and/or growth in the cells.

The step of optically detecting light passing through the well may include passing light through a curved interface of the well formed by the bottom of the well (e.g., a solid curved surface) or the curved surface of a droplet (e.g., hanging droplet). The step of optically detecting light passing through the well may include optically detecting light on the imaging surface that is magnified only by the curved interface of the well, without any additional lensing. For example, a magnifying objective is not necessary to magnify and/or focus the image of the cells.

In some variations it may be beneficial to include one or more growth/division modifying agents in the wells of the sample plate. For example, agents creating conditions in which bacterial cells are viable but not culturable (VBNC) may speed up the detection of bacteria in some assays. In some variations these agents may be referred to as growth accelerating agents because they act to either accelerate growth of the target bacteria, or modulate the bacteria so that they grow (e.g., elongate) without dividing, which may enhance the ability of the AMBR system to detect them.

For example, described herein are methods of monitoring cell growth by asynchronous magnetic bead rotation (AMBR) of magnetic particles, the method comprising: allowing cells to bind to magnetic particles; exposing the cells to a specific growth accelerating agent; applying a rotating magnetic field at a driving rate so that the magnetic particles rotate asynchronously to the applied magnetic field at an asynchronous rotation rate; and detecting a change in the asynchronous rotation rate indicative of cell growth.

Examples of specific growth accelerating agents include drugs (e.g., certain antibiotics), and other conditions that result in bacterial elongation without dividing (e.g., temperature modulation, etc.). For example, it is known that for certain bacteria cold temperatures, carbon dioxide, desiccation, high osmolarity and/or nutritional deprivation may induce elongation. Thus a growth-accelerating agent may be an agent inducing elongation, including one or more of: antibiotics, cold temperature, carbon dioxide, high osmolarity, etc. The growth-accelerating agent may be matched to the target cell type (e.g., bacterial type).

Thus, in some variations, the step of detecting a change in the asynchronous rotation rate indicative of cell growth may comprise detecting a change in the asynchronous rotation rate of magnetic particles within different wells having different concentrations of specific growth accelerating agent.

In general, any of the systems and methods described herein may be used to determine a minimum inhibitor concentration (MIC) of a cell. In particular, methods and systems for rapidly determining (in parallel) MIC may be used. For example, described herein are methods of determining a minimum inhibitory concentration (MIC) for an antibiotic by asynchronous magnetic bead rotation (AMBR) of magnetic particles, the method comprising: allowing cells to bind to magnetic particles; distributing the magnetic particles and cells into a plurality of wells, wherein the wells comprise a curved interface, wherein at least some of the wells include an antibiotic in a plurality of different concentrations for different wells; applying a rotating magnetic field at a driving rate so that the magnetic particles within the wells rotate asynchronously to the applied magnetic field at an asynchronous rotation rate; and detecting a change in the asynchronous rotation rate indicative of cell growth in each of the plurality of wells.

The method may also include the step of determining a minimum inhibitory concentration for the antibiotic from the detected change in the asynchronous rotation rate for the plurality of wells.

The systems and method describe here may be applied to food testing to determine food safety. For example, described herein are methods of rapidly testing for a foodborne pathogen using asynchronous magnetic bead rotation (AMBR) of magnetic particles, the method comprising: homogenizing a food sample; allowing bacteria from homogenized sample to bind to magnetic particles; applying a rotating magnetic field at a driving rate so that the magnetic particles rotate asynchronously to the applied magnetic field at an asynchronous rotation rate; and detecting a change in the asynchronous rotation rate indicative of cellular binding and/or growth in the cells. In some variations the homogenization step is optional (as the sample may be sufficiently amenable to binding any bacteria to the magnetic particles).

The method may also include enriching the homogenized food sample to increase the number of bacteria. Enrichment may include incubation (with or without agitation) in an enriched growth medium. As mentioned, this method may also be performed in the presence of a growth accelerating agent (e.g., elongation agent). For example, the method may include adding a growth accelerating agent so that bacteria bound the magnetic particles elongate.

The method may also include clustering or aggregating the magnetic particles. In some variations the method includes using a multiwell plate having a curved interface. For example, the method may include placing the magnetic particle within a well having a curved interface.

This method may be particularly useful for testing for one or more of the more common foodborne pathogens. In particular, the magnetic particles may be treated with binding agent specific to one or more of these pathogens. For example, the magnetic particles may include a binding agent specific for one or more of: *Salmonella; Listeria; E. coli* O157; *Campylobacter*; and *Vibrio*.

Also described herein are methods of optimizing patient care, including personalized patient care. For example, described herein are methods of optimizing cancer therapies using asynchronous magnetic bead rotation (AMBR) of magnetic particles, the method comprising: homogenizing a tumor sample; allowing tumor cells from homogenized sample to bind to magnetic particles; exposing different aliquots of the magnetic particles with bound tumor cells to different therapeutic agents and/or different concentrations of therapeutic agents; applying a rotating magnetic field at a driving rate so that the magnetic particles rotate asynchronously to the applied magnetic field at an asynchronous rotation rate; and detecting a change in the asynchronous rotation rate indicative of cell growth for each of the different aliquots of the magnetic particles with bound tumor cells. In some variations, the method includes aggregating or clustering the magnetic particles of each aliquot. As mentioned above, the method may be performed within a well having a curved interface; for example, each aliquot of magnetic particles may be placed within a well having a curved interface.

Also described herein are methods of sorting magnetic particles bound to an analyte from magnetic particles unbound to an analyte. Such a method may include the steps of: placing a plurality of magnetic particles in communication with a first surface; applying a rotating magnetic field to the magnetic particles, wherein the rotating magnetic field is rotating in an oval pathway above a critical frequency for the magnetic particles; and differentially driving the unbound magnetic particles across the first surface away from the magnetic particles bound to the analyte.

BRIEF DESCRIPTION OF THE DRAWINGS

FIG. 1a is a schematic representation of an AMBR sensor on a microscope, including an electromagnet, sample chamber, rotating magnetic bead and microscope lens or sensor. FIG. 1b shows cell elongation (from i to ii). FIG. 1c illustrates the effect of elongation of the attached bacterium on the rotational period of the magnetic particle. The rotational period change is observed as a peak shift in the FFT spectrum. FIG. 1d shows a scanning electron microscopy image of a magnetic bead system, in which a single E. coli cell is attached to a 2.8 µm magnetic bead. The scale bar is 2 µm.

FIG. 2a shows schematic figures and FIG. 2b shows 100× oil immersion optical microscopy images of a magnetic particle with initially a single bacterium attached and subsequent cell divisions. The scale bar is 2 µm. FIG. 2c is a graph showing cell growth and division as observed with this variation of an AMBR system. Cell division is observed at 104 minutes and again at 177 and 199 minutes. The error bars correspond to the measurement error in the rotational period and the exponential fits are a guide to the eye. FIG. 2d shows rotational data of the AMBR system at 177 minutes, showing the second cell division. Intensity data is acquired from a region of interest in the microscopy video. FIG. 2e shows optical microscopy images of the cell division. Data in FIGS. 2c and 2d have been normalized, to 1, at time zero.

FIG. 3a shows an image of a 16 well card made by injection molding and Polydimethylsiloxane (PDMS). FIG. 3b illustrates exemplary results showing raw periodic laser intensity data corresponding to the rotation of the sample for one well; FIG. 3c is an image of a 16 sensor array AMBR system prototype that incorporates low-power lasers and phototransistors to measure rotational data (with black tray that supports the disposable card). FIG. 3d illustrates a graph of antibiotic susceptibility results for averaged and normalized data with E. coli bacteria. FIG. 3e shows bright field microscopy images of a group of beads and bacteria in the presence of 1 µg/mL ampicillin at 2000 seconds and 6000 seconds; FIG. 3f shows as a similar group of cells and magnetic bead in 8 µg/mL ampicillin at 2000 seconds and 6000 seconds.

FIG. 11 schematically illustrates rotation of a small number of magnetic microspheres at the bottom of a 96-well microplate.

In FIG. 13A the electromagnets are not installed; in FIG. 13B the lasers are not installed.

In FIG. 15A, the aperture between the light source and the top of the well has a diameter a that is less than the diameter of the well, b (a<b). In FIG. 15B the arrangement of FIG. 15A is shown including an aperture above the optical detector (having an opening of diameter d), which may reduce crosstalk between adjacent wells.

FIGS. 16A-16G illustrate the lensing effect of various wells that may be included as part of a multiwell plate for AMBR testing. In FIG. 16A the index of refraction at the curved aperture between the solution (n1) and the outer surface (n2) is such that n1>n2, thus the rays converge towards the optical sensor. In contrast in FIG. 16B the index of refraction n1 is less than the index of refraction n2 (n1<n2), thus the rays diverge. FIGS. 16C and 16D illustrate the scenario for spherical droplets, another example of which is shown in the top-opening hanging droplet well shown in FIG. 16E.

FIG. 17a shows a stable magnetic particle group formed after the application of a rotating magnetic field at 100 Hz, 1 mT. FIG. 17b shows the same group from FIG. 15a after increasing the field strength of the rotating magnetic field to 100 Hz, 10 mT for 10 seconds. The scale bar is approximately 20 micrometers.

FIG. 18a-d illustrate various clusters of magnetic particles rotated by AMBR over time.

FIGS. 19A and 19B illustrates one method for the formation of a cluster of magnetic particles.

FIGS. 23a-e illustrate the formation and use of a microfluidics chamber. For example, FIG. 23(a) show s microfluidic glass channels were patterned and etched using standard glass lithography. FIG. 23b shows an image of the microfluidic droplet device. FIG. 23c is a picture of the microfluidic device inside the electromagnet coils, which generate a rotating magnetic field at its core. FIG. 23d is an optical microscopy image of an 8.8 μm magnetic bead rotating asynchronously with an external rotating magnetic field at a 50 Hz driving frequency, bead rotation rate being much lower (0.8 Hz). Visual aid is provided to observe the bead rotation. FIG. 23e shows droplets of 0.5 nL to 1 nL in volume were formed by applying a vacuum at the outlet and applying hydrostatic pressure at the oil inlet. A microfluidic device of this design holds between 50 and 75 droplets.

FIG. 24a illustrates the frequency of the number of beads per droplet with various particle concentrations. The data is fitted to the Poisson model. FIG. 24b shows frequency-dependent rotational response curves at driving frequencies between 0.1 Hz and 1000 Hz. The solid line represents the rotational response dominated by a permanent dipole; the dotted lines connect the data to aid in visualization. FIG. 24c shows rotational response of fifty 8.8 μm beads in 50 Hz driving field in droplets (top) and on glass surface with 106 beads/mL concentration (bottom). The rotational period for beads in droplets was calculated to be 2.11±0.62 s, providing a coefficient of variation of 30%. The beads on glass surface are subject to magnetic and surface interactions; as a result, the average rotational period was 3.5±1.4 s, (40% CV). The data is fitted to the normal distribution. FIG. 24d shows normalized rotational response of 8.8 μm magnetic beads at a driving frequency of 50 Hz for 300 minutes under constant environmental conditions.

FIGS. 25a-25d show Single cell growth measurements using the AMBR sensor. FIG. 25a is a schematic representation of bacterial growth and division at select time points, which corresponds to (in FIG. 25b) light microscopy images of bacterial growth and division. FIG. 25c shows the rotational period of the bead and bacteria complex (AMBR biosensor) shown in FIG. 25b. At the point of division, at 103 minutes, the rotational period decreases, as the effective volume of the biosensor is substantially reduced. The data, of each bacteria generation, is fitted by an exponential curve. The error bars represent the measurement error. FIG. 25d shows an optical microscopy image sequence of the bacteria division process at time 103 minutes.

FIGS. 26a-26c show small cell-population growth and susceptibility measurements using the AMBR sensor. For example, FIG. 26a shows optical microscopy images of small cell-population growth on an 8.8 μm magnetic bead in MH-PB solution. FIG. 26b shows the rotational period of the 8.8 μm bead corresponding to the figures above (circles), and bacteria that have been fixed in glutaraldehyde (squares). The data is fitted with an exponential curve. FIG. 26c shows averaged rotational responses from 3 separate experiments of 0 μg/mL and 0.5 μg/mL and 2 separate experiments of 2 μg/mL and 4 μg/mL gentamicin. The MIC, as determined by the Vitek2, is 1 μg/mL. Bacteria treated with gentamicin concentrations below the MIC continued to grow, whereas bacteria treated with concentrations above the MIC did not show noticeable growth. The difference is evident within 15 min. Data sets are fitted to an exponential curve. The error bars represent the measurement error.

FIGS. 32a-c illustrate one variation of a driving magnetic field source for a system for monitoring asynchronous magnetic bead rotation, configured from two pairs of Helmholtz coils.

FIGS. 33a-c illustrate another variation of a driving magnetic field source for a system for monitoring asynchronous magnetic bead rotation, configured as a grid.

FIGS. 34a-c illustrate another variation of a driving magnetic field source for a system for monitoring asynchronous magnetic bead rotation, configured similarly to a motor.

FIGS. 38A and 38B show one variation of a multiwell plate having 16 wells.

FIGS. 40A and 40B show schematics of a multiwell pate similar to that shown in FIGS. 38A and 38B.

FIGS. 46a-c illustrate one example of the use of a cluster of magnetic particles in an AMBR system.

FIGS. 47a-g illustrate the use of a cluster of magnetic particles to determine MIC.

FIGS. 50A and 50B show a slide having handing droplet wells that are open on both the top and bottom; FIG. 50C illustrates imaging rotation of a cluster of magnetic particles though a well from the slide of FIG. 50A.

DETAILED DESCRIPTION OF THE INVENTION

Figure 1:
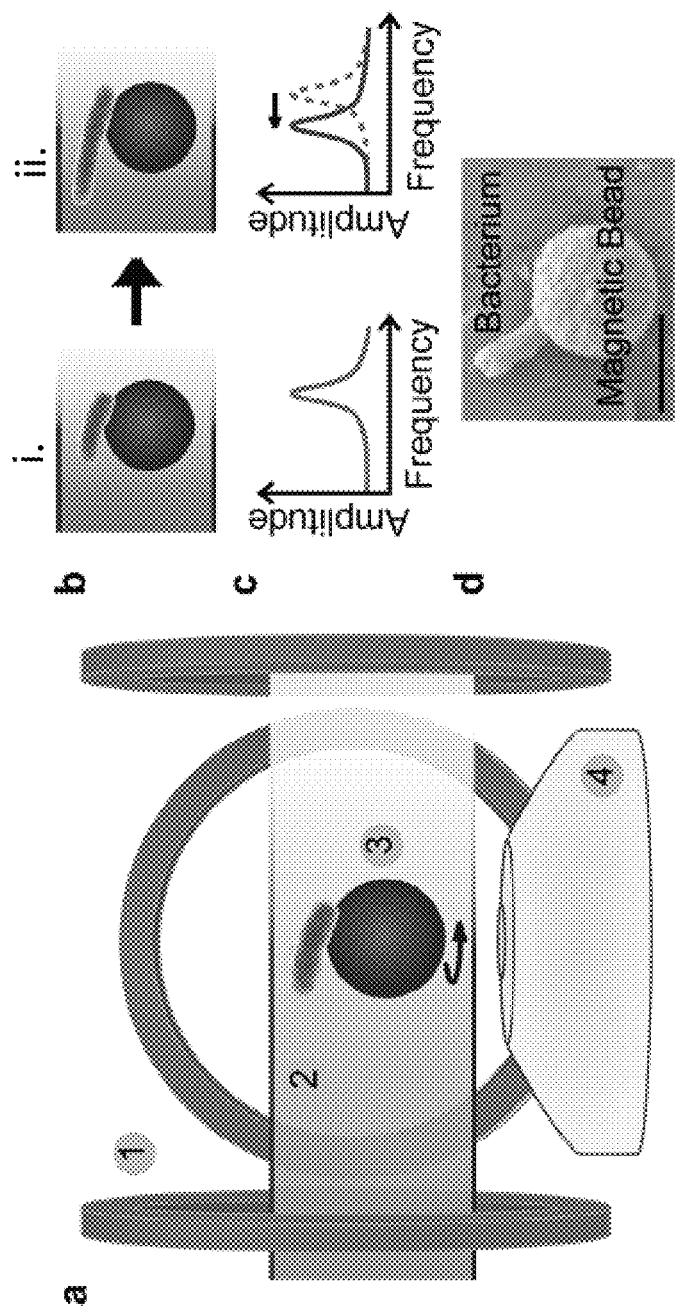
FIGS. 1a-d illustrate detection of single-cell elongation using the AMBR method.

Described herein are systems, devices and methods for monitoring (or enhancing the monitoring of) cellular growth and/or activity using magnetic particles. In particular, described herein are asynchronous magnetic bead rotation (AMBR) systems, devices, components, and methods, including methods for monitoring cell growth/death and response.

For narrative convenience, the description below is divided up into various sections, however the concepts, devices, methods and systems may be combined in whole or in part with one or more of the other systems, and are not (unless the context makes it clear otherwise) exclusive.

Typically, in AMBR, a magnetic particle (e.g., a bead) is exposed to a driving rotating magnetic field that is rotating above a critical frequency so that the rotational rate of the magnetic particle is sensitized to changes in the shape or size of the particle including object bound to the particle. In some cases (e.g., particularly with ferromagnetic beads) at low driving rates the magnetic bead rotates synchronously with the driving magnetic field, referred to as the synchronous mode. When the magnetic particle rotates at a rate that is slower than the driving rate, the system may be referred to as operating it the asynchronous mode. In contrast to the synchronous mode, in the asynchronous mode the rate of rotation of the magnetic particle slows as analytes binds and/or swell on the particle. The amount of slowing may depend on the shape and size of the bound analyte. While the magnetic particles remain in the synchronous mode, binding and swelling (e.g., growth) does not appreciably slow the rotation of the magnetic particle.

The magnetic particles that may be used for AMBR (which may be paramagnetic, superparamagnetic, or ferromagnetic) may be functionalized so that they bind to an analyte. Although the various and examples described herein refer to analytes that are cells, other analytes may be detected, including molecules (proteins, carbohydrates, etc.) nucleotides, and the like. If the analyte is a cell, such as a prokaryotic or eukaryotic cell or cells (e.g., bacterial, cancer cells, etc.), the rate of rotation of the magnetic particle in the asynchronous rotation mode may depend upon the size and/or shape of the bound cells. Changes in the cell shape or size, including changes in the number of cells as the cell grows, divides and/or dies, will alter the rotational rate of the magnetic particles. Thus, by monitoring the rate of rotation of the magnetic bead or beads bound to analyte in the asynchronous mode, it is possible to detect and monitor cell activity, including cell growth and death, and response to drugs that affect cell metabolism (e.g., antibiotics).

Thery of Magnetic Bead Rotation in AMBR

The rotational response of a magnetic bead, when placed within an external rotational magnetic field, is frequency dependent and is governed by its permanent or induced magnetic dipole. A magnetic bead with a permanent magnetic dipole, in a rotating magnetic field with a frequency of $\Omega$ will have an average rotational frequency of $\langle \dot{\theta} \rangle = \Omega$, when $\Omega < \Omega_c$ and $\langle \dot{\theta} \rangle = \Omega - \sqrt{\Omega^2 - \Omega_c^2}$, when $\Omega > \Omega_c$ where the critical frequency $\Omega_c = mB/\kappa\eta V_H$, where m is the bead's magnetic moment, B is the magnetic field amplitude, $\kappa$ is the shape factor (6 for a sphere), $\eta$ is the dynamic viscosity, and $V_H$ is the hydrodynamic volume of the rotating body. When $\Omega > \Omega_c$, information about the magnetic bead complex or the external environment can be calculated by observing its rotation rate. For experimental conditions in which m, B, and $\eta$ are constant, $\Omega_c$ is inversely proportional to $\kappa$ and $V_H$, which we define as the effective volume, $V_{eff}$, as shown by $$\langle \dot{\theta} \rangle = \Omega - \sqrt{\Omega^2 - (A/V_{eff})^2}, \quad (1)$$

where $A=mB/\eta$ is a constant.

For magnetic beads with an induced dipole, the bead's rotational frequency is $\theta = (\chi'' B^2 V_m)/(\mu_0 \eta \kappa V_H)$, where $\chi''$ is the imaginary susceptibility of the bead, $V_m$ is the volume of the magnetic content of the bead, and $\mu_0$ is the permeability of free space. For experimental conditions in which $\eta$, B, $\chi$, $\mu_0$, and $V_m$ are constant, the rotational rate of the bead is expressed by $$\dot{\theta} \text{ is proportional to } 1/\kappa V_H \text{ which is prortional to } 1/V_{eff} \quad (2)$$

In summary, the changes in the effective volume for beads can be observed by measuring changes in the rotational rate for particles with either permanent or induced magnetic dipole.

Currently AMBR systems may monitor the rotation of magnetic particles under the driving rotating magnetic field to detect the asynchronous rate of rotation. The rate of rotation is typically monitored using a laser (e.g., focusing laser or coherent light source), a microscope, camera, and typically software to help visualize and detect the rate of rotation. Described herein are devices, system and methods that may simplify and improve AMBR, including significantly improving the monitoring of cells.

The present devices and method described herein (AMBR devices, systems and methods) use magnetic beads that may rotate asynchronously when a driving magnetic field used to rotate the magnetic beads exceeds a critical frequency. Above this critical frequency, the particle's rotation is asynchronous with the external field, thus the particle is in an asynchronous condition. In some of the variations described herein, the magnetic beads are clustered so that the AMBR technique may be applied by rotating the entire cluster (or in some variations multiple clusters) of magnetic particles in the asynchronous regime. Changes in this asynchronous rotational rate of the entire cluster of particles may be used to detect bacteria, monitor their growth, and measure their response to antibiotics with single cell sensitivity. Furthermore, measurement of cluster's rotation is straight-forward, simple, and inexpensive: it can be performed with any of the prototype devices described herein using low-cost and readily available electronic components, e.g. diodes and photodiodes, allowing for broad applicability. Rather than only being able to measure population growth, the AMBR methods described herein can also measure the growth of a small number of bacterial cells with single cell sensitivity. With the present techniques, appropriate antimicrobial therapies can be quickly determined, which will not only help to reduce antimicrobial resistance, but reduce detrimental effects from bacterial accumulation.

FIGS. 1a-1d illustrate the rotation of a single magnetic particle in the asynchronous mode in order to illustrate the general AMBR technique. For example, in FIG. 1a, an AMBR sensor system is described including a microscope 4, an electromagnet 1 forming the magnetic driver, a sample chamber 2, a magnetic particle 3 with a bound cell. The optical sensor is the microscope lens. The electromagnet is configured to apply a rotating magnetic field so that the magnetic particle(s) rotate asynchronously with the rotating magnetic field. In this asynchronous mode, cell elongation may be detected, as indicated in FIGS. 1b and 1c. In FIG. 1b the bound cell grows over time to elongate from the size shown in FIG. 1b(i) to that shown in FIG. 1b(ii). The particle may be rotating during this incubation period as a constant driving rotating magnetic field is applied. As shown in FIG. 1c, the elongation of the attached bacterium can be measured by observing the change in the rotational period of the magnetic particle/bacterium complex, which is caused by the increase in the effective volume. The rotational period change is observed as a peak shift in the fast Fourier transform (FFT) spectrum shown to the right in FIG. 1c(ii). This may also be shown using autocorrelation. FIG. 1d shows a scanning electron microscopy image of a magnetic bead system, in which a single E. coli cell is attached to a 2.8 μm magnetic bead.

Thus, the AMBR technique may be used to achieve a high sensitivity for detection of both binding and growth of bacteria. For example, sequential binding events of single E. coli cells can be measured. With the attachment of each cell, the magnetic particle's rotational rate is significantly slowed.

Another example is shown in FIGS. 2a-2e, which shows that with the growth of one E. coli cell, the rotational period slowed by more than 400% in a short time period. These figures also show data for multiple cell divisions, where each time a division occurs the rotational period is reduced. This reduction is a result of either the daughter cell dividing off of the particle or dividing and attaching to the particle in a different orientation. For susceptibility measurements, the overall trend of slowing is observed over minutes or hours. The overall slowing of the period essentially is the growth curve of the attached bacteria. When no bacteria are present on the surface of the bead or when the bacteria are not actively growing or dividing, the rotational period is constant. When there is growth, it can be observed as an exponential increase in the rotational period of the bead.

Figure 2:
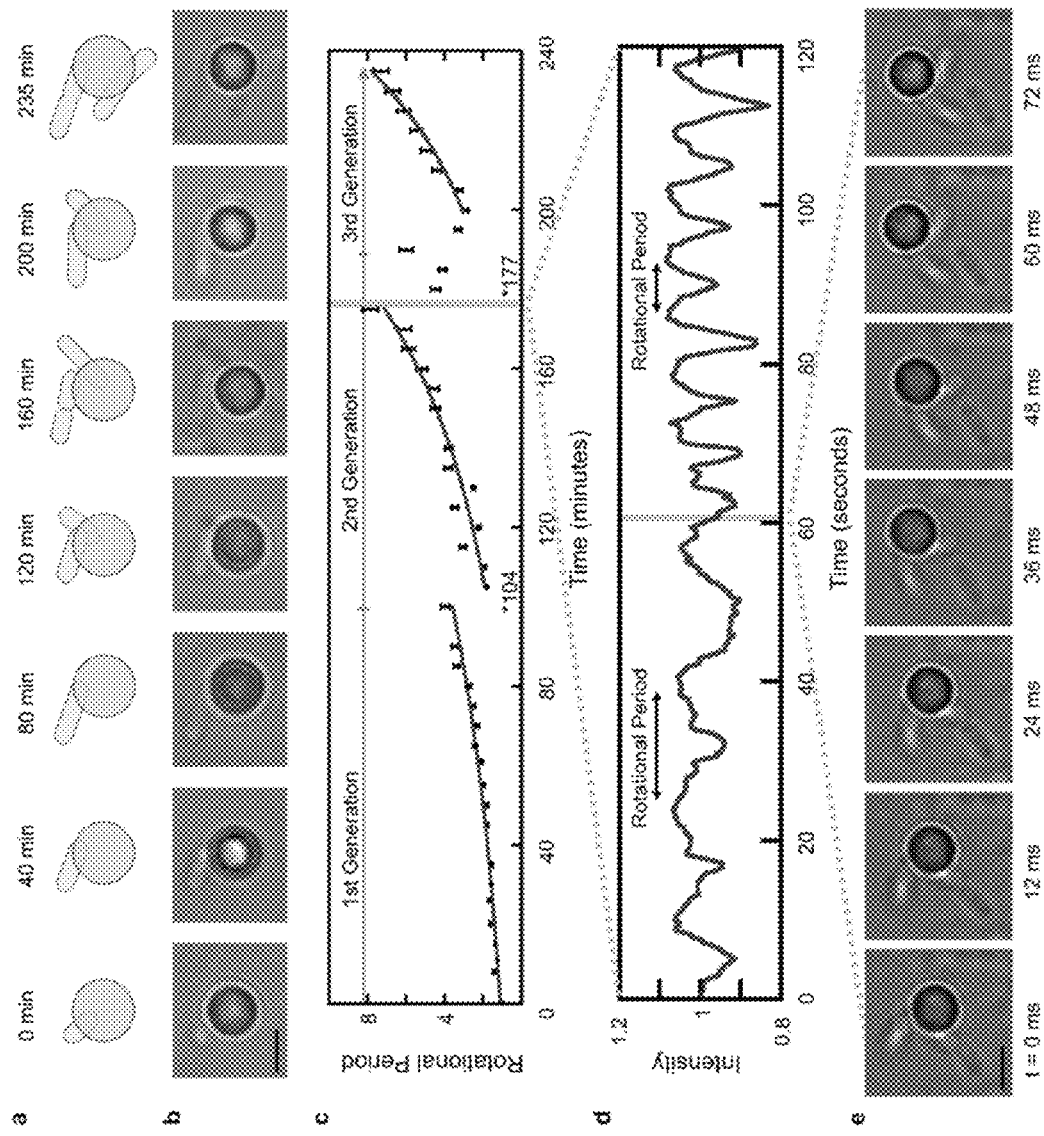
FIG. 2 illustrates growth and division of a single E. coli bacterium, measured with an AMBR system and observed with an optical microscope.

In FIG. 2a-2e, growth and division of a single E. coli bacterium, measured with an AMBR sensor and observed with an optical microscope, is monitored. FIG. 2a is a schematic of the magnetic particle and bound bacteria. FIG. 2b shows 100× oil immersion optical microscopy images of a magnetic particle with initially a single bacterium attached and subsequent cell divisions. Cell growth and division as observed with the AMBR technique by monitoring cell rotation, as shown in FIG. 2c, observing the rotational period of the magnetic particle. Cell division is observed at 104 minutes and again at 177 and 199 minutes. The error bars correspond to the measurement error in the rotational period, and the exponential fits are a guide to the eye. As an example, rotational data of the AMBR sensor at 177 minutes, showing the second cell division, are illustrated in FIG. 2d. In this example the frequency of rotation was determined from intensity data acquired from a region of interest in the microscopy video, as shown in FIG. 2e, which are optical microscopy images of the cell division occurring at approximately 60 seconds.

While using single beads allows for straight-forward measurements on the microscope as shown in FIGS. 1a-1d and 2a-2e, it is not as straightforward to measure a single 2.8 μm bead rotating in an integrated, automated system. Single particles are simply harder to detect, visualize and track rotations. One solution proposed herein is the use of clusters of magnetic particles, rotating together, in the AMBR system.

Clusters of magnetic particles for use in an AMBR system may contain any appropriate number of magnetic particles. For example, between about 5 and about 10,000 particles, between about 10 and about 5000 particles, between about 100 and 1000 particles, etc. Such clusters of magnetic particles (particularly clusters of more than about 5 particles) are typically avoided in magnetic bead assays including AMBR assays, because they may be difficult to control (e.g., position) because it was believed that the rotation may be unpredictable in the asynchronous mode, particularly if one or more of the particles broke away from the cluster; this could be misinterpreted as a change in binding or cell size. The systems and methods described above have determined that this presumed problem may be dealt with by controlling the manner in which the clusters are formed and/or the shape of the well in which the clusters are rotated, as well the manner in which the clusters are rotated and/or the formulation of the media.

Figure 3:
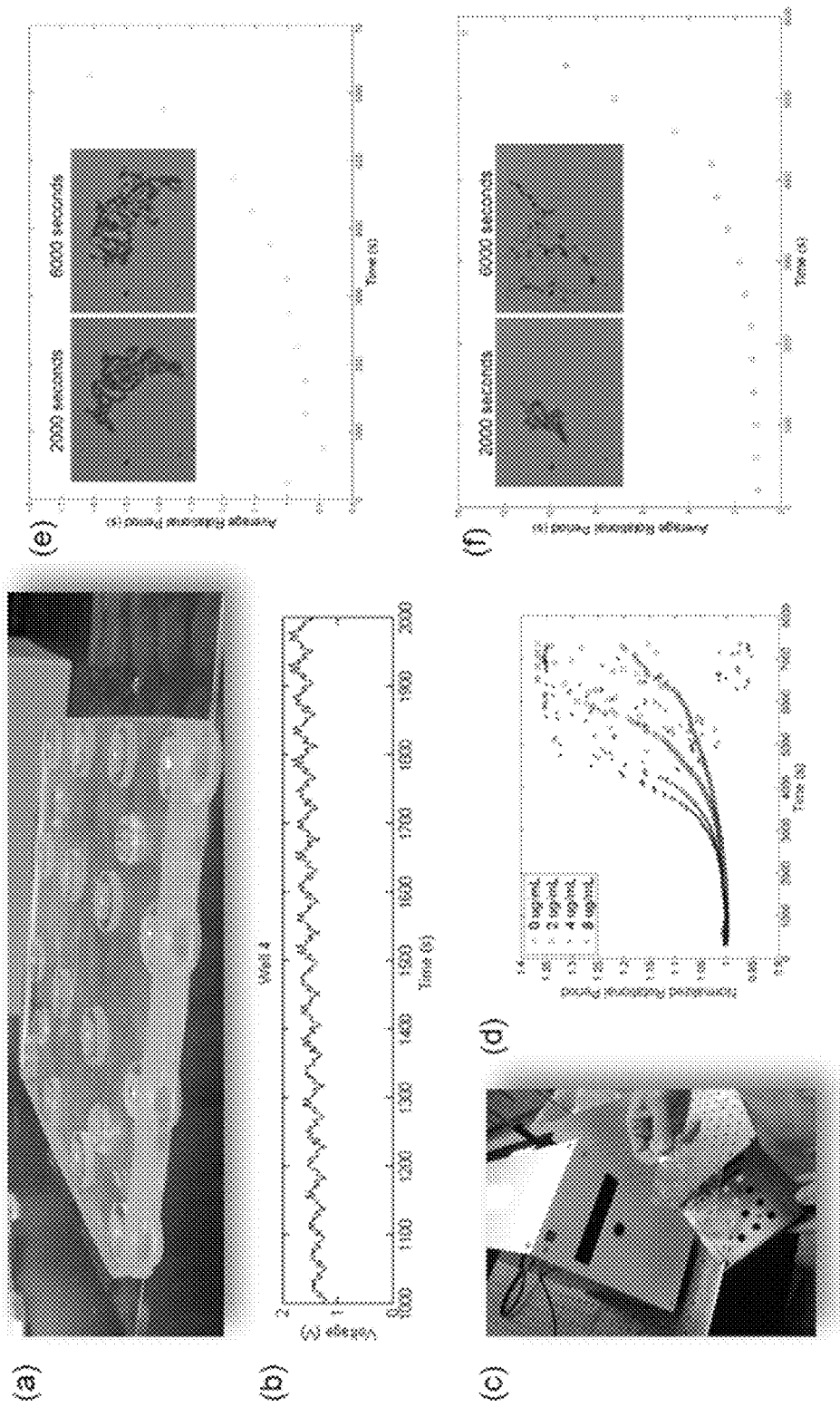
FIGS. 3a-f illustrates results from one variation of a multiwell prototype device using a 16-well disposable card.

In practice, the inventors have found that the use of clusters in an AMBR assay has numerous unexpected advantages. For example, when cell division occurs, a significant portion of the bacteria remain on the surface of the particles. Thus, a more reliable growth response may be detected (as cells are not all shed into the medium). When a cluster or group of particles is used, similar sensitivity as seen with single-particle AMBR can be obtained. Clusters may be readily detected and their rotation more easily optically resolved. This effect has been confirmed and the growth results are shown in FIG. 3d with E. coli. Surprisingly, when a cluster of particles is used, the observed growth curve is much more continuous and smooth as compared to single particles (e.g., see FIG. 2e). This allows for response to antibiotics to be measured in a reproducible manner, which makes the technique more clinically relevant. FIGS. 3a-3f illustrate a prototype device that has been used as a proof-of-principle for the rotation of clusters and use of multiwell sample plates. The example shown in FIG. 3a is a 16-well disposable plate. Each well in the plate (which may also be referred to as a "card") has been treated to contain a single cluster of magnetic particles that rotate as a group. As described below the treatment may include the application of a magnetic field to cluster the particles either before, during or after the addition of bacteria or other cells. The particles may be weakly magnetically attractive. FIG. 3d shows results obtained when monitoring the growth of a small group of E. coli on clusters of magnetic particles in the presence of 0, 2, 4, and 8 μg/mL of antibiotic (ampicillin). As can be seen from the FIG. 3d, the rotation period of the group increases as the bacteria grows. In this example, the antibiotic ampicillin acts as a growth accelerating agent. Although ampicillin may prevent or inhibit division of the cells, as the concentration of ampicillin increases, the bacteria become elongated, increasing in length more quickly than at lower concentrations of ampicillin. Thus differences in cell growth can be seen in approximately one hour (the rotational period doubles in one hour). This growth observing time is indeed rapid (up to 6 times faster), compared to other methods, such as turbidity, which can require as long as 6-24 hours with the Vitek 2 to measure growth of already isolated bacteria. The configuration of FIGS. 3a and 3c includes three elements: a rotating magnetic field, a cluster of magnetic particles that responds to the rotating field by rotating asynchronously, and a method to detect rotation of the cluster. Another aspect of this example is the concurrent parallel measurement from different wells of rotating clusters, which is described in greater detail below.

Magnetic particles are already in widespread used in clinical diagnostic settings to magnetically separate nucleic acids and are also commonly used to perform whole cell separation of cell lines (for food testing and for stem cell isolation). Such magnetic particles are already FDA approved for immunomagnetic separation as a step before performing polymerase chain reaction (e.g. BacLite and Magnapur) in identification of MRSA.

The present techniques offer a number of features not present in conventional measuring systems. These may include: a means to create a rotating magnetic field; a means of measurement of the asynchronous rotational period of one or more microscopic beads coated with specific antibodies, wherein the rotational rate, driven by a magnetic field, is inversely proportional to the fluidic drag; the fluidic drag increases when bacteria adhere to the bead (detection); bacterial growth results in additional drag whereas failure to grow results in no change (Susceptibility testing). Fluidic drag and bacterial growth testing could also be performed using other cells, such as, but not limited to, yeast and mammalian cells. Any appropriate cell type may be used.

In the context of clusters of magnetic particles (or beads), asynchronous magnetic bead rotation (AMBR) refers to magnetic particles or groups of magnetic particles that rotate at a rate slower than a rotating magnetic field. Binding events of bacteria to an AMBR magnetic bead cluster may cause step wise changes in the rotational period. As more bacteria bind, the sensor's rotational period increases. Growth may be indicated by the continual slowing of the rotational period. So, as the bacteria grow, they become larger or increase in number (on or near the particle) and increase the drag felt by the magnetic particle ("sensor"). This drag change can result from a change in hydrodynamic volume changes of the rotating particle or particle group or by viscosity changes in the surrounding environment, where both result from growth of bacteria. Growth curves in different environments can then be measured in parallel and susceptibility can be determined. Detection of cell growth also depends on affinity binding, but instead of observing a step-wise change in the rotational period, a growth curve is observed. Thus, observation of a growth curve indicates presence of bacteria ("detection by growth").

Example Testing Protocol

Figure 4:
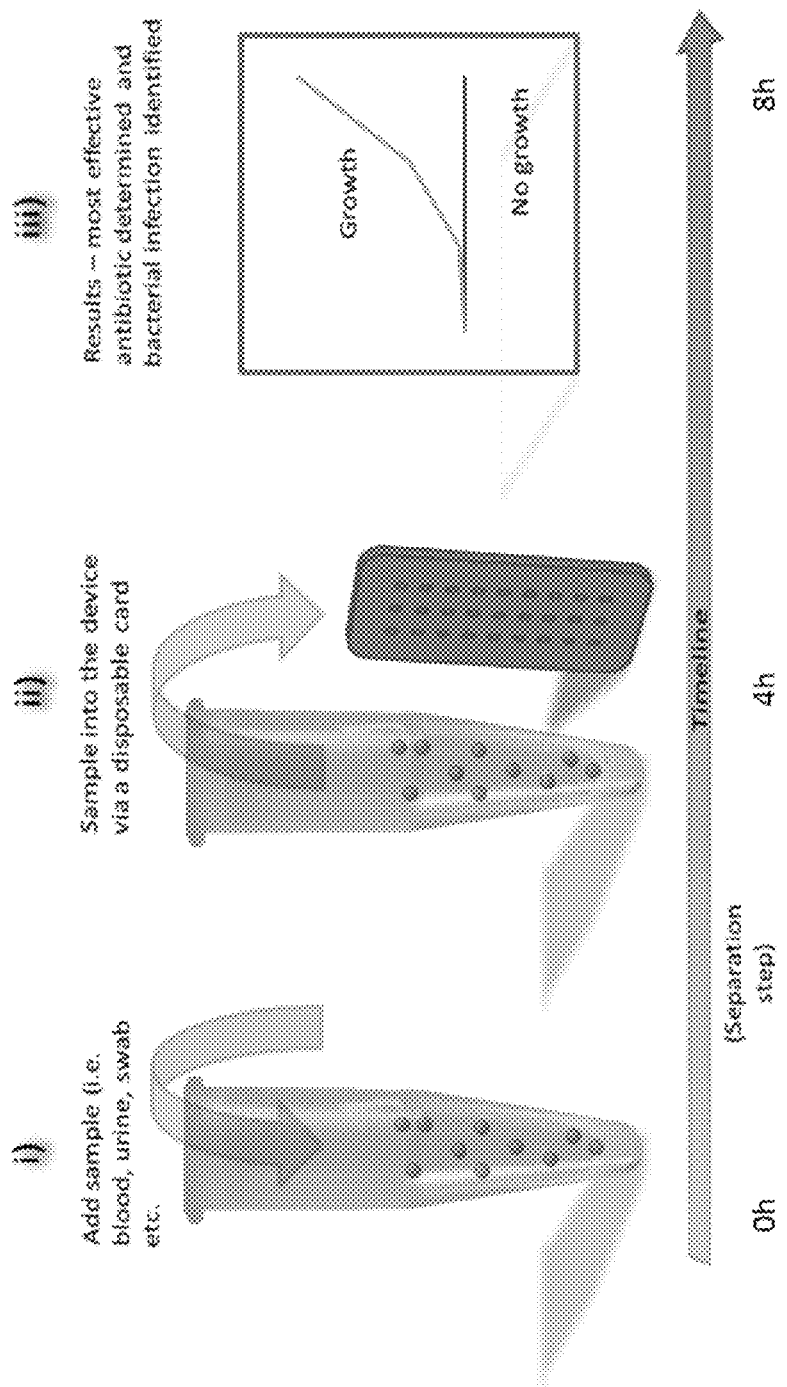
FIG. 4 illustrates one variation of an exemplary method of using AMBR to determine cellular growth.

A clinical sample (e.g. blood, urine, etc) may be mixed with a Muller-Hinton (MH) or phosphate buffered saline solution that contains magnetic beads that are coated with antibodies specific to the pathogen of interest. The bacteria and beads are incubated together to allow for ample time to bind and if necessary, population growth of the bacteria. Immunomagnetic separation is then performed using a magnetic pick pen (or regular magnetic separator) and the separated beads, with attached bacteria, are re-suspended into MH broth. This solution (now containing only bacteria with attached bacteria) is then placed into the disposable (preferably multiwell) plate, where the beads are asynchronously rotated in the card reader for detection/identification and antibiotic susceptibility testing, where the minimum inhibitory concentration will be determined. In some variations, the magnetic particles (with bound cells) are not washed or purified from the sample material; the assay may be run with the sample material present (e.g., in whole blood, etc.). FIG. 4 illustrates one example of a similar testing protocol. In this example, the sample (blood, food, tissue, etc.) is added to the magnetic particles in a manner that allows them to bind. The magnetic particles may then be separated (magnetically) and washed. In some variations the particles and cells may be placed into various wells of a test card/multiwell plate. In some variations sufficient numbers of magnetic particles may be included to form a cluster within each well. Finally, the magnetic particles are rotated in the asynchronous regime and monitored optically to determine cell growth (elongation and/or division). In some variations antibiotic or other conditions or agents may be used in individual wells.

Figure 5:
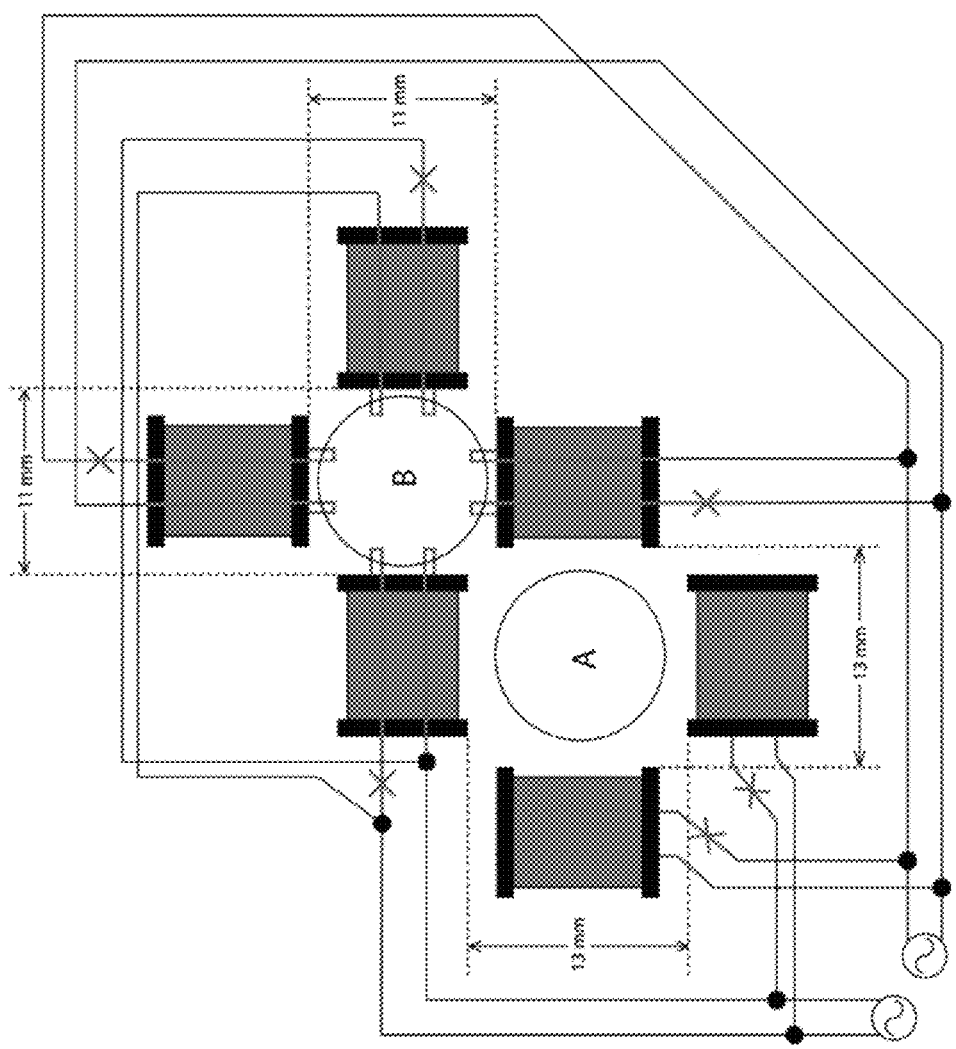
FIG. 5 illustrates multiple inductors used to form a driving magnetic field source.
Figure 10C:
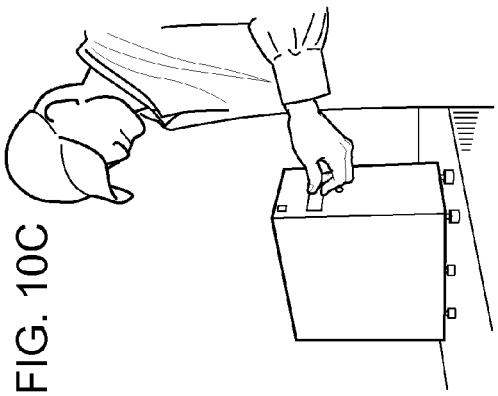
FIG. 10 illustrates one variation of a 16 well prototype that enables 16 growth measurements in a disposable multiwell card.
Figure 10B:
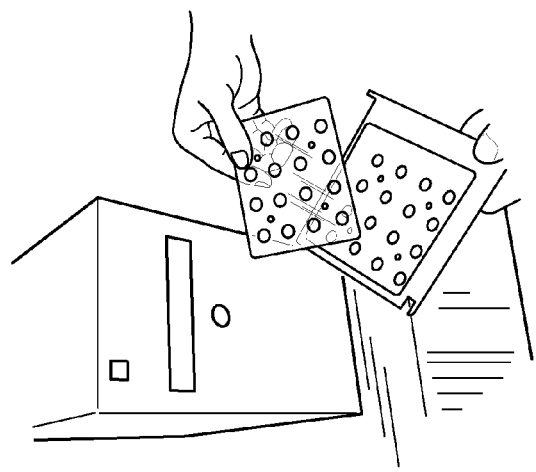
Figure 10D:
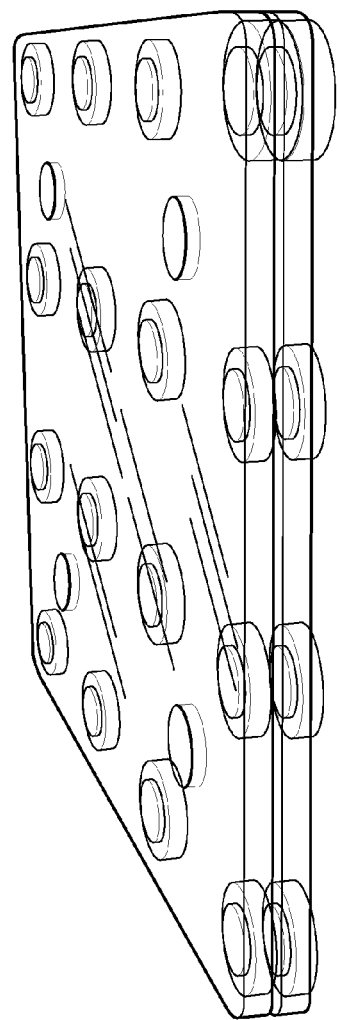
Figure 10A:
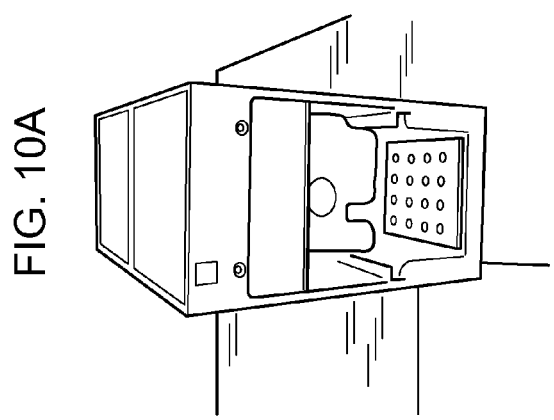

In practice, any appropriate magnetic field driver may be used to apply the driving magnetic field to one, a subset or all of the wells of the multiwell plate. For example, a permanent magnet may be physically rotated, or a plurality of electromagnets may be controlled to generate a rotating magnetic field. For example, in some variations off the shelf inductors may be placed on a printed circuit board, such that each well in the disposable card is surrounded by four inductors. This is the configuration used in the 16 well prototype shown in FIGS. 5 and 10a, where only location B (as shown in the configuration in FIG. 5) is used. While four inductors are used in the current prototype for a single well, rotating magnetic fields could also be created by using more or less than four inductors. FIG. 5 is an exemplary setup for a pair of wells (A and B); the layout shown in FIG. 5 may be repeated mosaic-like to form a plurality of rotating magnetic field drivers that each separately control the applied magnetic field in a single well. In this example, a single inductor may be used as part of the driver for three (or possibly more) wells.

Figure 6:
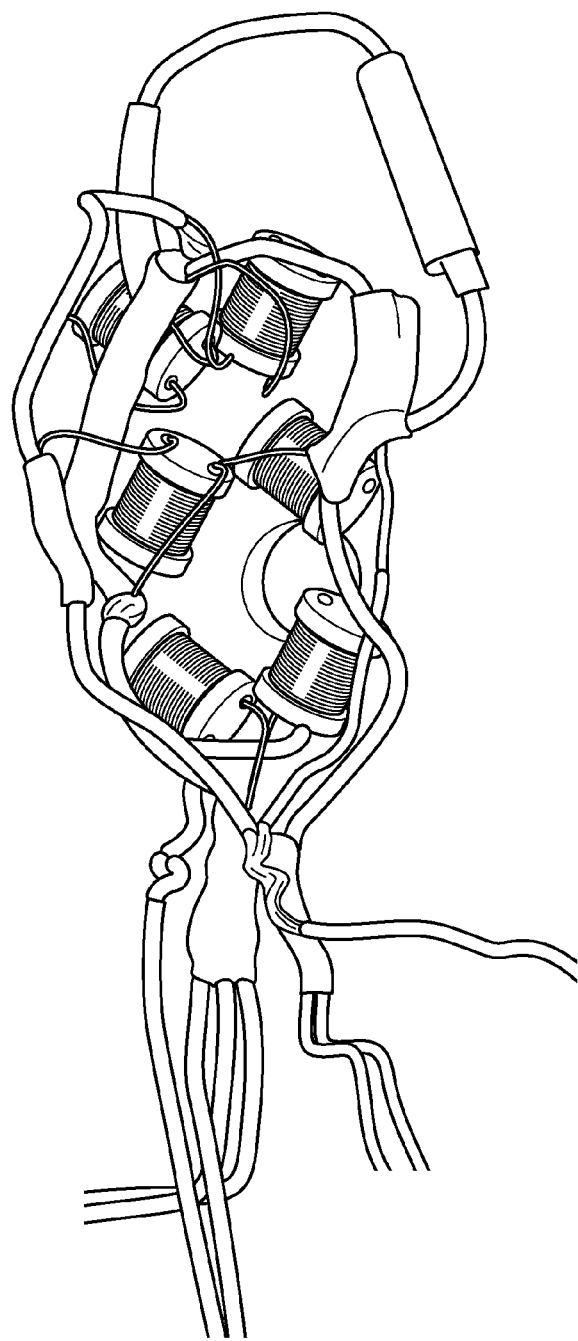
FIG. 6 shows an implemented version of the inductors forming a driving magnetic field source shown schematically in FIG. 5.

This general configuration in FIG. 5 allows for there to be a well at least at locations A and B. The differences between the well locations are in the strength of the generated magnetic field, where, for example at location B the field may be stronger than at location A. This setup also may utilize off-the-shelf inductors. The positioning of the inductors in this 2-field setup is the same as in a conventional 1-field setup but the wiring has been altered to produce constructive interference in both dimensions for A and B. An example wiring configuration is shown in FIG. 5. (The 'X' that appears on one terminal of each inductor represents the long end of the inductor. An image of a tested inductor setup is shown in FIG. 6.

Figure 7A:
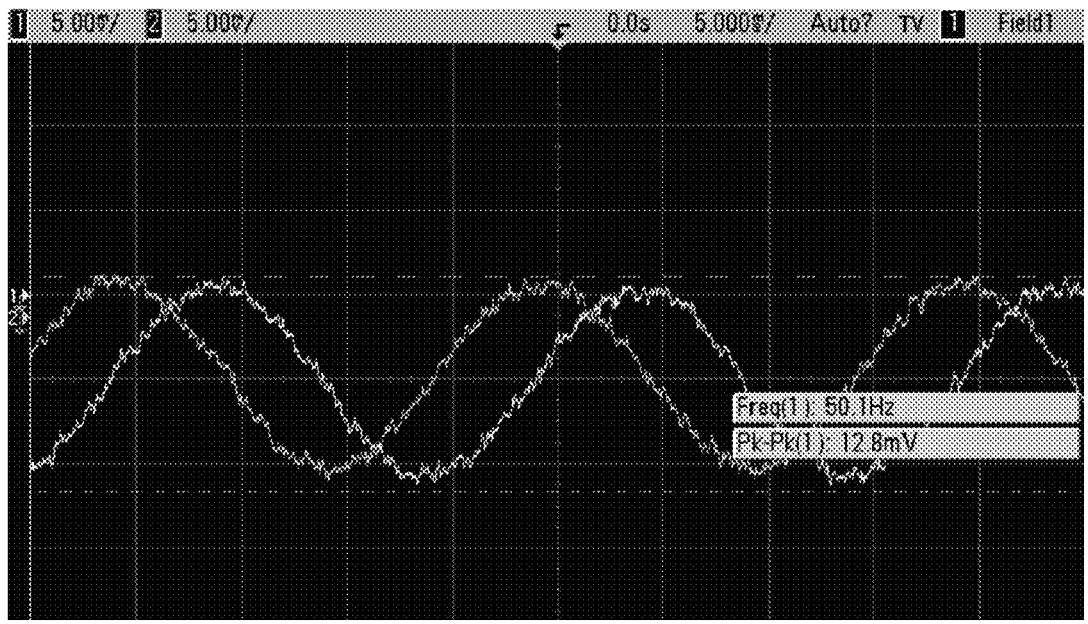
FIG. 7A shows the field characterization for location A in the exemplary schematic shown in FIG. 5, where the field strength=1.28±0.1 mT.
Figure 7B:
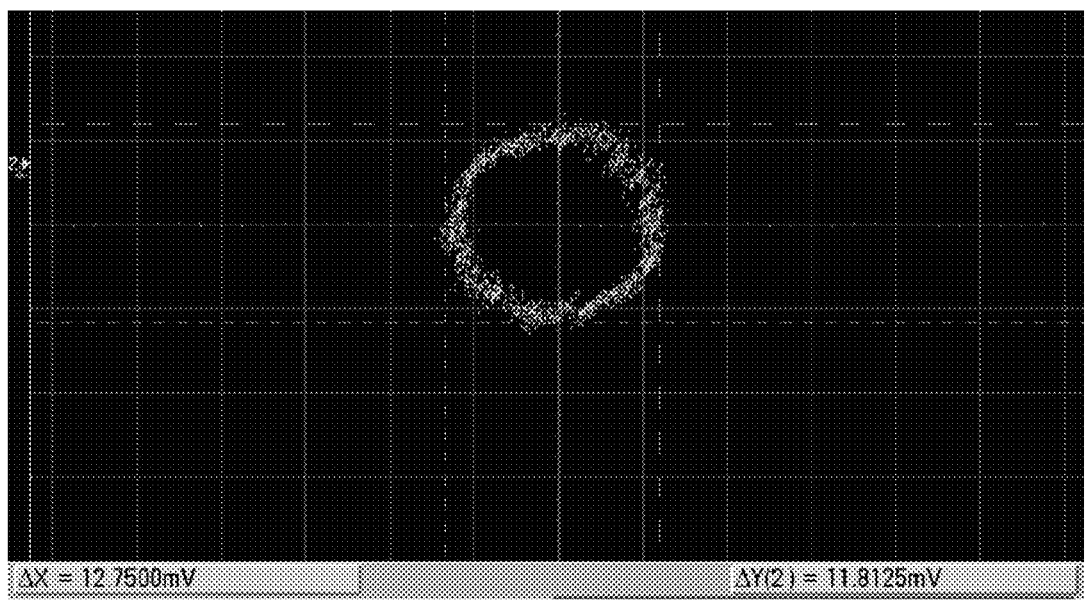
FIG. 7B illustrates the circularity of the produced field.
Figure 8A:
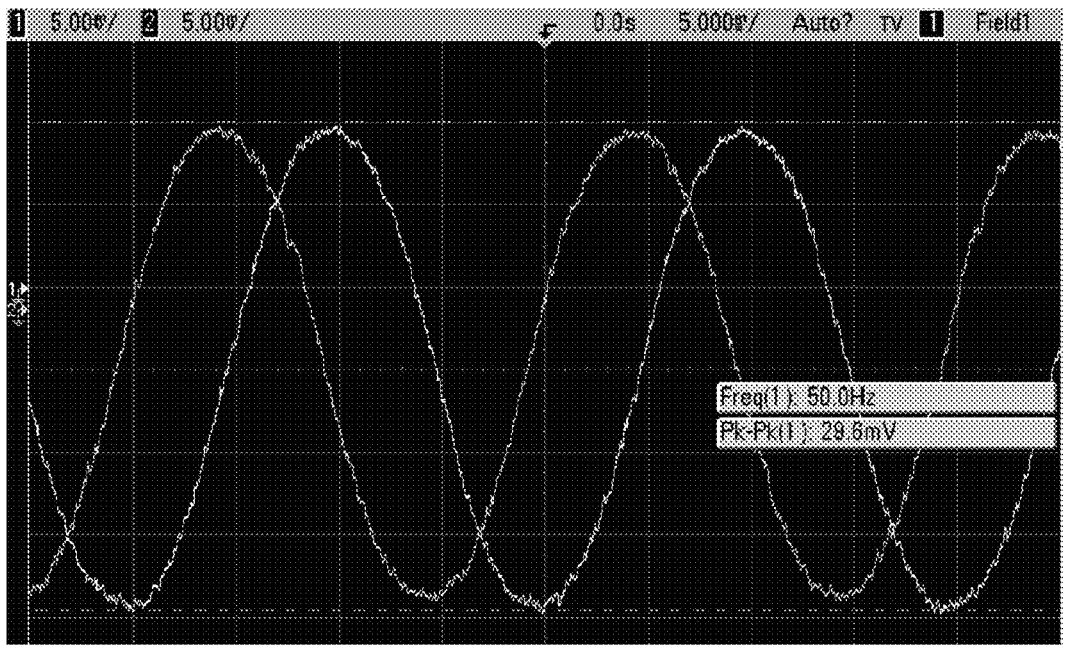
FIG. 8A shows the field characterization for location B in the exemplary schematic shown in FIG. 5, where the field strength=3±0.2 mT.
Figure 8B:
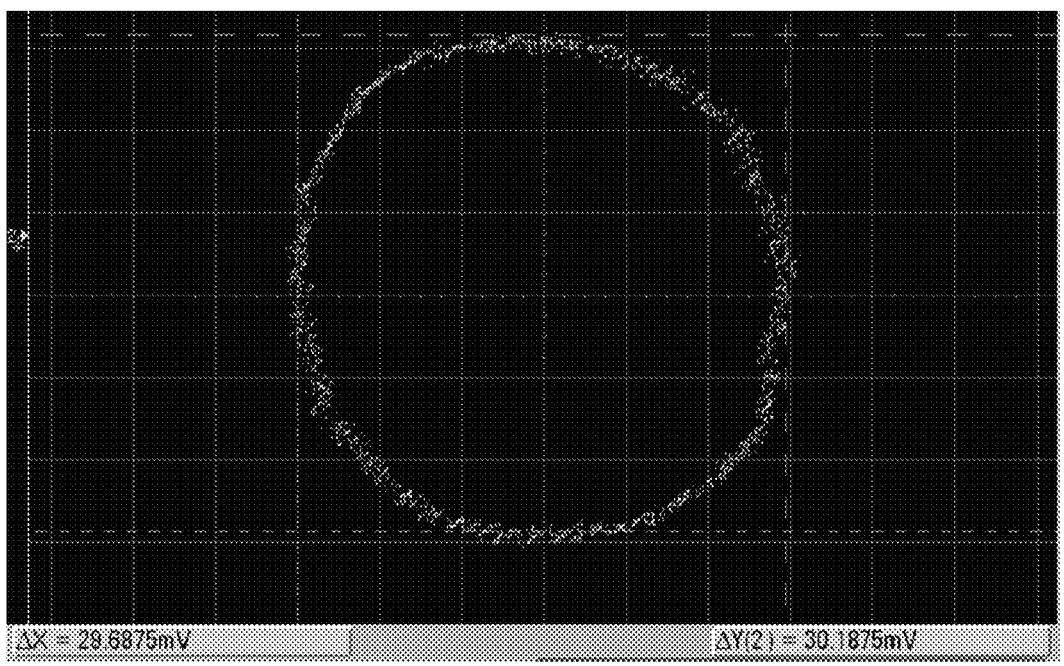
FIG. 8B illustrates the circularity of the produced field.

In this example, the resulting fields were tested using a 2D field probe (see, FIGS. 7 and 8). Graphs containing both x and y fields as well as a graph of the x-field vs. y-field were prepared for the fields and both locations A and B. The probe outputs 5V/T (=>5 mV=1 mT). This shows that it may be possible to double the sampling capacity per area for some designs, drastically decreasing size. In other examples, one could provide an analogous setup, but that has equal field strengths at locations A and B, e.g., using different inductors and changing the dimensions of the inductor arrays.

In any of the variations described herein, a multiwell card or plate may be used. A multiwell pate or card may be disposable or reusable. In general this card (or plate, or cartridge) may be disposable and have multiple wells. In some variations the wells may be pre-loaded with drugs (e.g., growth accelerating agents, including antibiotics, etc.); for example each well may contain a different amount of dried or lyophilized antibiotics. In some variations the wells may have lyophilized growth media. The wells may be hydrated with magnetic beads with attached bacteria (if bacteria are present in clinical sample).

Any of the wells described herein (and particularly the multiwell plates) may include one or more curved interfaces. The curved interface may aid in both positioning a cluster of magnetic particles as mentioned, but it may also help in imaging the cluster, as described in detail below.

For example, when suspended beads are placed into the fluid, they may be randomly dispersed. If the well includes a curved interface, it may allow for gravity alone, or gravity in combination with an applied 1 D static magnetic field, to bring particles together and aggregates the combined particles at the lowest point of the curved interface. Application of a rotating magnetic field may further aggregate (cluster) the magnetic particles. At the end of this step, a single cluster of many magnetic beads with attached bacteria is formed and rotates as a single unit, typically staying in one place (e.g., the lowermost part of the curved surface; see, e.g., FIG. 11). Bringing the particles to a single point of a curved interface could also be accomplished by use of magnetic gradients. Additional methods for clustering the magnetic particles are described below (and illustrated, e.g., in FIGS. 19A-19B).

The curved surface also has the additional aspect of expanding the laser beam so that the modulated laser signal can be more readily measured with a photodetector (see card reader description). For each well in the card, one or a cluster of magnetic particles are then magnetically rotated (asynchronously) at the bottom of the well. Some variations utilize a curved air-fluid interface (e.g., hanging droplet), however a curved interface can also be plastic-fluid as in curved 96-well plates or in water/oil interface.

Upon cellular growth, the total hydrodynamic volume of the aggregate or cluster increases, thereby reducing the rotation rate (e.g. increasing the rotational period).

Any of the systems described herein may be configured as multiwell plate/card readers. For example, a card reader assembly may be configured to accept one or more disposable cards, where any card can be removed or inserted, without affecting the other cards; cards may be accessed in any order, or they may be analyzed in the order in which they are inserted, or otherwise.

For example, in some variations the system for performing AMBR may include a light source (such as lasers, LEDs, fiber optic, etc.) mounted vertically in the top of the assembly and in some examples is able to produce a plurality of collimated laser beams. It should be noted that collimated light is not necessary, but may be preferred in some variations. Each collimated beam in this example passes through a small pinhole and then through a sample well in the disposable card; an example of this is illustrated in FIGS. 14A-15B. Exemplary light sources, include both LED and laser light sources. In some examples the light sources are narrow-linewidth and/or tunable light sources.

Since the well in some variations is curved at the bottom, there is a lensing effect that may expand the beam and project a shadow image onto the photodetector (in some variations of the device, this is a phototransistor). If the beam is focused through the sample, a scattering pattern may be produced rather than an image. An array of phototransistors may be used to detect the laser intensity passing through each well, which is relayed to a computer through a data acquisition board.

In some variations, each well is surrounded, in-plane by four electromagnets (e.g., refer to FIGS. 5 and 6 for an example), such as four inductors in the horizontal plane that are perpendicular to each other. This variation of the driver is equivalent to a stator in a bi-phasic DC brushless motor, where a rotating magnetic field is generated by passing an (sinusoidal) ac current that is phase-lagged by 90 degrees to each set of electromagnets. Additionally, in some variations, two function generators may be used to produce the ac current, which is later amplified. PID temperature controllers may be used to heat the device to 37 deg C., particularly in variations in which the reader (AMBR system) is configured to act as an incubator (e.g., regulating temperature and/or humidity and/or gas mixture).

The asynchronous rotational period of the rotating cluster of magnetic particles may be measured using the light modulation that is produced when each laser beam (or other light) passes through the small magnetic bead cluster. The cluster has inherent optical asymmetry so the intensity of light that passes through the cluster depends on the cluster's orientation. In this way, the modulated signal is produced and as shown in FIG. 3b. From this, the rotation rate can be measured by simply tracking the peak-to-peak distance (period) of the modulated intensity. This data may be determined, for example, using an autocorrelation or FFT algorithm. Computer control (e.g., software, hardware and/or firmware) may be used to control collection and analysis.

In some variations, magnetic fields may be generated by an array of perpendicular Helmholtz coils, allowing for a plurality of individual magnetic fields to be generated (16 are used in the prototype in FIG. 10a), which are similar to that shown in FIGS. 5 and 6. Magnetic fields used to rotate the magnetic microsphere cluster may be low amplitude and have field values of, for example, 10 Oe and rotation rates of 100 Hz.

As mentioned, automatic control (e.g., computer control) may be used to track the rotational period of the magnetic bead cluster/aggregate in each well in real-time. In some variations software may be used to plot the growth curves (e.g., period on the y-axis and time on the x-axis) for each antibiotic concentration.

Figure 9:
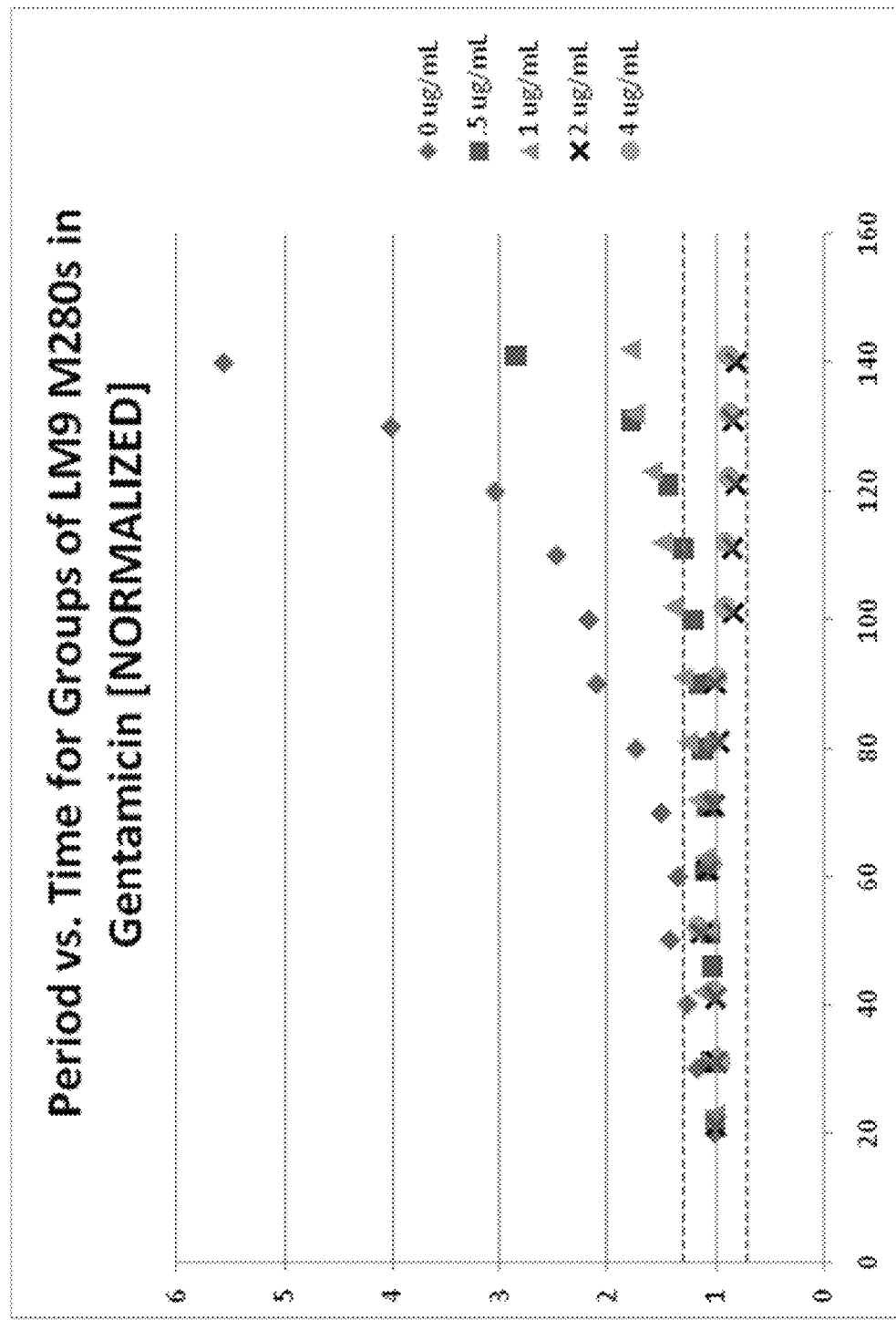
FIG. 9 illustrates the rotational period (in seconds) of rotating magnetic beads with attached E. coli versus time (in minutes) for various concentrations of antibiotic (Gentamicin).

Using the exemplary techniques just described, a minimum inhibitory concentration for a sample can be determined, as is shown in FIG. 9, where the minimum inhibitory concentrations (MIC) MIC=2 ug/mL. The dotted lines are at y=0.7 and 1.3 (±0.3). The y axis is the average rotational period in seconds and the x axis is time in minutes. While these growth curves were obtained by leaving the driving frequency at a single set rotational frequency of 100 Hz, it is also possible to obtain growth data by performing full frequency scans (scanning the driving frequency from low to high). However, frequency scans inherently take longer than setting the driving frequency to a single value.

Another exemplary device is shown FIG. 10a-10d. The multiwall plate in this example has 16 wells, and the system includes a corresponding 16 lasers and 16 phototransistors. The device accepts the 16 well disposable plate. The device may be used to perform parallel measurement of asynchronous rotation in 16 different well samples. Off the shelf inductors were used to generate the rotating magnetic field and create a scalable form factor for the prototype device, which is table mountable. Also, in this device we use inverted droplets to suspend a group of particles that rotate together.

The present techniques may be expanded to performing large number of parallel analyses. These techniques are not limited to a particular number of wells, nor to the number of parallel well measurements that may be made. Some or all of an array of samples may be measured in parallel, e.g., simultaneously in real time. Or some subset of the array may be measured in parallel or serial fashion, for example, when looking to stagger measurements over time for comparative purposes across samples.

Any appropriate plane of asynchronous rotation (e.g., of the applied rotating magnetic field) can be used, and can be adapted to various embodiments. For example, in some variations the plane of rotation is parallel to the plane of the well; in other variations the plane is perpendicular to the plane of the well. Thus, while asynchronous rotation can be done in a plane perpendicular to the sample plane, rotation can also be performed using a plane of rotation in the sample plane. This mode of rotation has many advantages when there is more than one particle in a microwell or a large well. Specifically, if there are multiple particles in a well (i.e. at the bottom of a round-bottomed microwell; see FIG. 11a-11b), then the particles will be pulled to the bottom of the well by gravity. A small array of particles forms and can rotate as a unit. When attached bacteria grow, either the particle-to-particle spacing changes or the amount of bacteria on the exterior of the array increases. Both may result in an increase in rotational period, allowing for rapid growth monitoring. This configuration may be especially useful in the case of monitoring the growth of a larger amount of bacteria rather than one bacterium on one magnetic particle.

As mentioned, the AMBR techniques for monitoring the response of magnetically driven particles described herein have several advantages over conventional techniques, one of which is the ability to rapidly monitor the growth of cells, such as bacteria. A larger sensor array assembly, where each array is capable of monitoring an individual sample, but where the design is based on a 96 well plate, may also be used (see FIGS. 12 and 13A-13B). This configuration may also be used is biological assays testing, and enables monitoring an ensemble of particles in parallel with the specific application of fast determination of minimum inhibitory concentrations (MIC) of bacteria.

Figure 12:
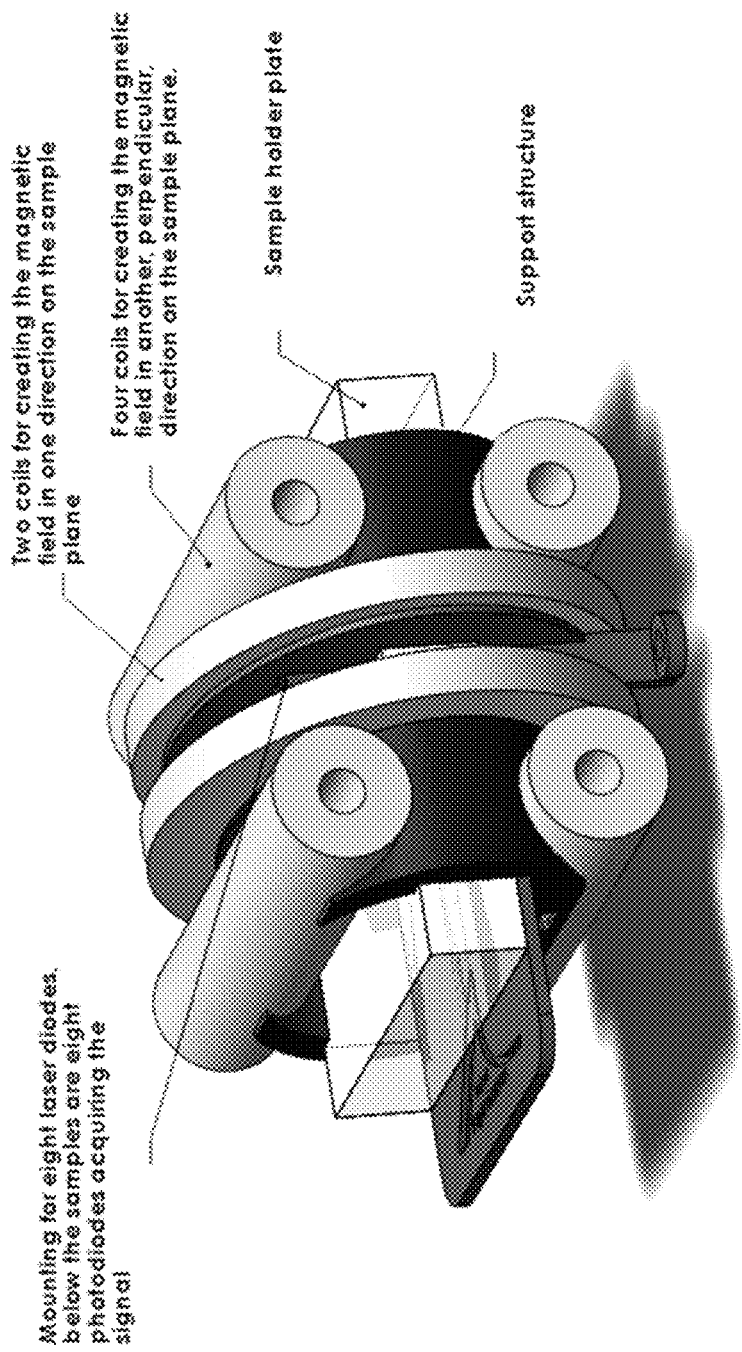
FIG. 12 shows one variation of a system that houses a 96 well plate and monitors 8 wells simultaneously. This variation allows for simultaneous measurement of bacterial growth in 8 different environments, such as varying concentrations of antibiotics.
Figure 13B:
FIGS. 13A and 13B show partially deconstructed view of one variation of a 96-well microplate AMBR reader for measuring growth of bacteria.
Figure 13A:
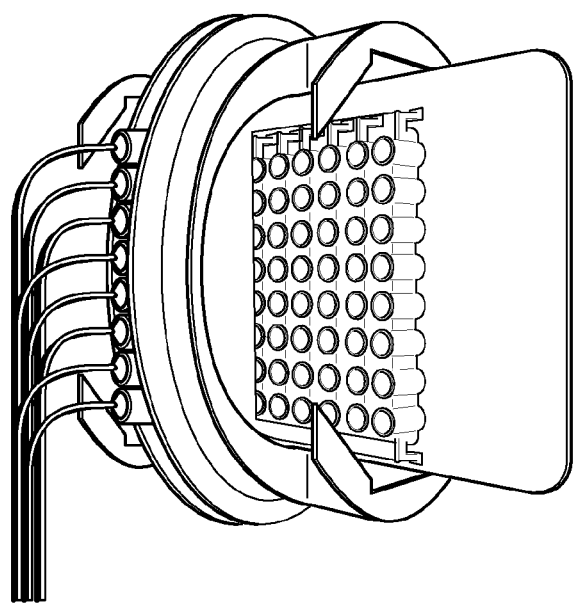

One particular advantage for the example shown in FIGS. 12 and 13A-13B is that it allows one to run 8 growth measurements at the same time, providing a rapid platform to determine an MIC in a 96 well (or higher) plate. A standard 96 well plate has 8×12 wells. An advantage to having an 8 well sensor is that the plate can be moved over by one column so that another set of 8 wells can be tested. In this way, samples can be exposed to several different antibiotics (different columns of the well plate) at varying concentrations (different rows of the well plate).

This technique may have other applications as well. For example, these plates (e.g., 96 well plates) may be used in the area of bacterial infections, offering an accurate, fast, low cost, low power, compact and easy to use device for determination of MICs. The potential impact for testing of single bacterial strains is promising. For example this technology is very applicable to when there is one bacterial strain that needs to be identified and tested for determination of an MIC.

While the design FIGS. 12 and 13A-13B has 8 sensors in a 1D array monitoring one row of a 96 microwell plate, in other examples the device may employ a 2D array that would enable monitoring for example every well in 96 microwell plate. Alternatively, the detectors and/or wells can be moved, so that the subsets of wells may be tested and used.

Currently, antibiotic susceptibility testing in the clinical lab has a turn-around time of two or more days. Excessive time-to-results can lead to inappropriate antimicrobial therapy. The present techniques, however, can dramatically reduce this time from days to hours.

Micrometer-scale and nanometer-scale magnetic particles may be rotated by the magnetic fields described herein.

Any of these systems may also be described in terms of drag. As discussed above, when magnetic particles are rotated by an external field, they can exhibit two types of rotational behavior. At low external rotation rates, magnetic particles rotate in-synch (phase-locked at a constant relative angle) with the external field. When the external rotational rate is increased, there is a point of criticality where the viscous drag experienced by the particle becomes equivalent to the magnetic torque acting on the particle. At this point, the particle becomes asynchronous (out-of-synch) with the external field. This point of criticality and therefore, the asynchronous rotation rate, is very sensitive to drag. As a result, when bacteria attach to the particle and grow there are significant changes in the speed of asynchronous rotation. Basically, the particle rotation slows with increasing cell size or concentration. In this way, cell growth can be rapidly detected. This general effect of slowing for increased cell size or concentration applies to any type of magnetic particle that rotates asynchronously with a magnetic field, e.g., ferromagnetic, paramagnetic, superparamagnetic, etc. In the above-described example, superparamagnetic beads from Invitrogen are used, "M-280"s.

Many of the techniques described herein utilize a method that is based on asynchronous magnetic bead rotation (AMBR) in which the magnetic beads are generally micron-scale and coated with pathogen specific antibodies. Bacteria are bound to the magnetic particles and allowed to grow, which has the effect of dramatically slowing the rotational speed of the magnetic particles. When placed in varying concentrations of antibiotics, susceptibility results can be rapidly obtained. This speed is a result of the well-demonstrated single-cell sensitivity of the AMBR method.

The AMBR methods described herein, and particularly those using the clusters of magnetic particles, are sensitive to the growth of bacteria at the single-cell level. This allows for extremely rapid susceptibility measurements to be made, which reduces instrument testing time. Also, since magnetic beads are used, sample preparation time may be reduced through immunomagnetic separation. By seamlessly combining immunomagnetic separation with AMBR, both the sample preparation time and instrument testing time are significantly reduced, which dramatically reduces the total test turn-around time.

In addition to the features described above, additional aspects and variations are provided.

Using Inverted Droplet as Self-Aligning Lenses for AMBR Applications

In some variations the AMBR procedure may be performed in a hanging droplet. The hanging droplet procedure, may offer many unexpected advantages. For example, an inverted droplet of fluid (water, growth media etc.) can be used as a sample platform for AMBR, allowing both the uninhibited rotation of the magnetic particles with bound analyte as well as enhancing the visualization of particle rotation. The shape of the hanging droplet, or of a sample changer that is similarly curved on the side facing the sensor (e.g., camera), may be used as a lens to focus and/or enlarge the shape of the magnetic particle(s) in the droplet.

Using inverted droplets, we have rotated single magnetic particles and groups of magnetic particles (including clusters), and measured the rotation rate either with an optical microscope or focusing a laser on it and measuring the intensity fluctuations.

In some variations an unfocused laser or an LED (in combination with a first pinhole) and a focusing pinhole may be used in place of a focused laser when using inverted droplets: the inverted droplet may act as a concave lens, magnifying the "shadow image" of the rotating object, and the signal can be measured, e.g., with a photodiode. The magnification of the shadow image may depend on the distance between the image plane (e.g., the imaging plane of the camera) and the sample; typically, the longer the distance, the higher magnification. In some variations, the light source (e.g., LED) may be collimated using one or more additional lenses (e.g., collimating lenses), fiber optics, or the like.

Figure 14A:
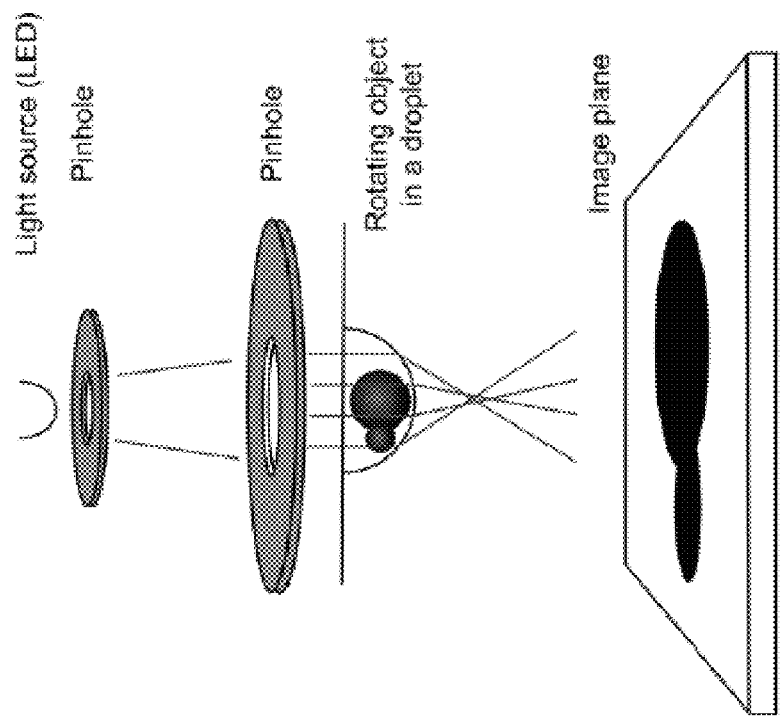
FIG. 14A is a schematic illustration of one variation of a system having a curved interface (e.g., shown here as an inverted droplet) resulting in a lensing effect, using an LED light source.

FIG. 14A shows a schematic illustration of one variation of this setup. In this example, the light source has been replaced with an LED light and a first pinhole. The first pinhole is separated from the second pinhole (referred to as a focusing pinhole) by a distance; the first and second pinhole may collimate the light from the LED, which may clarify the shadow cast by the rotating magnetic particle as magnified by the curvature of the hanging droplet or curved bottom of a chamber. In FIG. 14A, the sizes are not shown to scale (including the sizes of the magnetic particle and spacing of the pinholes). The size spacing of the pinholes may be fixed or adjustable. For example, in one variation the system is configured so that the spacing between the first and second pinholes is adjustable (e.g., by rotating a control knob, manually or automatically) to enhance contrast and/or focus of the rotating cluster on the image plane of the camera.

In this example, which is a hanging droplet example, the gravitational forces acting on the magnetic particles/cluster of particles drives drive them to the bottom of the inverted droplet, reproducibly aligning it with the light source and detector.

The hanging droplet variation may be used to image an AMBR sensor consisting of a single magnetic particle, or a group of magnetic particles, or a cell, or a group of cells which are rendered magnetic by (specific or nonspecific) attachment or engulfing of magnetic nano- or microparticles. For example, this set up may be used to image and analyze cells that have internalized magnetic nanoparticles. As mentioned above, the light source may be a laser or a non-coherent light source such as an LED.

More generally, any of the systems and methods described herein may be adapted for use with cells that internalize magnetic particles. Cells with internalized magnetic particle may be made to rotate and may cluster and be made to rotate as a cluster similar to the clusters of magnetic particles described herein.

In FIG. 14A, the image plane is typically the image plane of a camera. Any appropriate camera may be used. As discussed in greater detail below, the camera may be a photodetector or a pixel array (e.g., CCD, CMOS etc.). The term camera is intended to be broadly understood as a light-sensitive sensor or array of sensors that is configured to detect rotational motion based on the image plane.

In general, the sample (e.g., magnetic beads, magnetically labeled cells, etc.) is contained within a curved-bottom ("lensing") chamber. The chamber may be a hanging droplet chamber, in which the curvature of the droplet forms the lensing lower surface. As mentioned, in some variations the curved bottom of the lensing chamber is a curved bottom plate or well instead of a droplet. Thus, a lensing chamber is generally a structure for holding a sample so that the surface of the chamber facing the image plane of the sensing apparatus is curved to act as a lens, e.g., focusing the light through the sample and onto the image plane. A structure configured to form a hanging droplet over the image plane (e.g., hanging droplet plate) is one form of a lensing chamber.

Figure 14B:
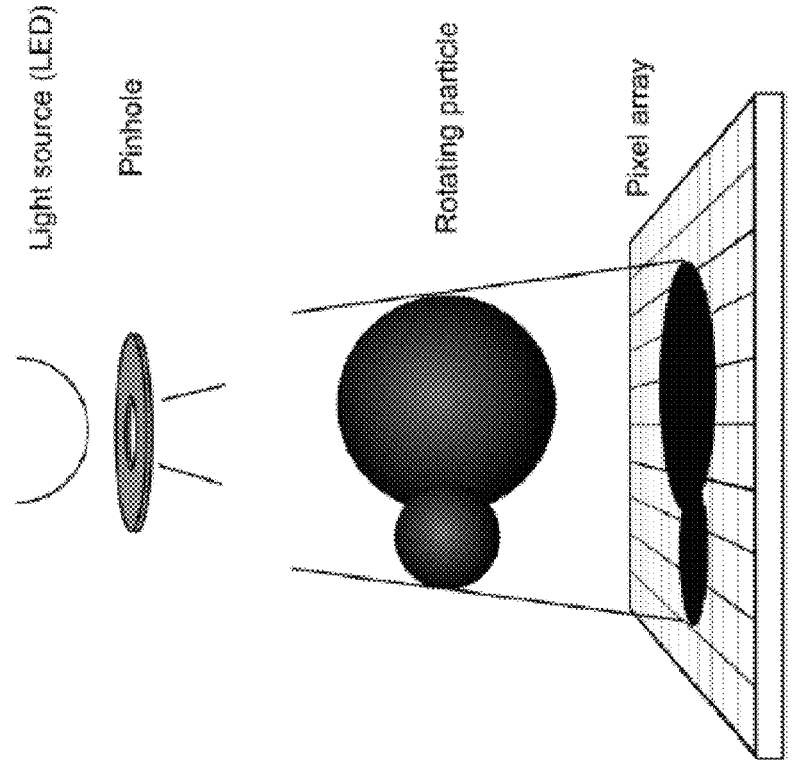
FIG. 14B is a schematic (partial) illustration of rotation of magnetic body imaged with an LED and a pixel array.

FIG. 14B shows another example of an AMBR system device schematically. In this example the rotating particle (with an attached analyte) produces a shadow image on the imaging sensor ("pixel array") that may be detected to determine frequency of rotation information.

Figure 15B:
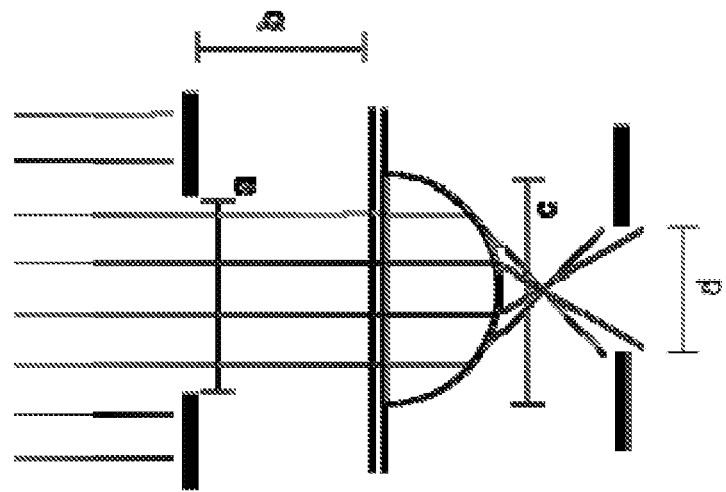
FIGS. 15A and 15B illustrate the lensing effect of a well having a curved interface.
Figure 15A:
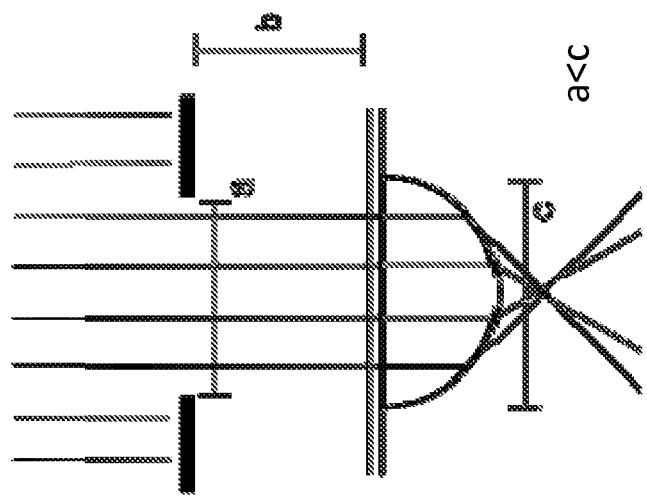

FIGS. 15A and 15B illustrate another configuration of a well having a curved interface, similar to that shown in FIG. 14A. In this example, the curved interface (which may be a hanging droplet or it may be multiwell device having a curved bottom surface) acts as a lens to produce an image that can be detected by the optical sensor (not shown) without requiring additional lensing. For example, in FIG. 15a the light (which does not have to be collimated as suggested by the figure) passes through a first aperture above the well having an opening of diameter "a". This diameter "a" is less than the diameter of the well, "c". In FIG. 15B, a second aperture is positioned above the optical sensor and has an aperture of size "d" which is less than "a". This second aperture may help prevent cross-talk between adjacent wells in a multiwell plate.

In general, the optical properties of the system may be configured to help optically detect rotation of the cluster of magnetic particles. For example, in FIGS. 16A-16G various configurations of wells having curved fluidic interfaces are shown. For each example, the optical properties at the curved interface (e.g., the index of refraction of the fluid in which the magnetic particles are rotating and the index of refraction of the surrounding medium) may determine how an image is passed onto the optical sensor. For example, in FIG. 16A the index of refraction of the well n1 is greater than the index of refraction of the plastic forming the well (n1>n2), thus the image has a focal plane above the optical sensor as shown. In contrast, when the magnitudes of the indices of refraction are reversed as shown in FIG. 16B the image projected onto the sensor is still magnified.

FIGS. 16C and 16D illustrate a similar phenomenon for spherical cross-sections (as may result from imaging through the side, rather than the top/bottom, of a well, or when using a droplet surrounded by oil. FIG. 16E illustrates one variation of a hanging droplet having an opening at the top. In this example, the hanging droplet well is formed as a channel through a solid substrate 1601.

Clustering of Magnetic Particles

As discussed above, in some variations it may be desirable to form a cluster of magnetic particles, which may rotate together as a group. This may simplify the determination of the rate of rotation of the magnetic particles, which will be the rate of rotation of the entire cluster of magnetic particles; the magnetic moments of the individual particles may add together and act to rotate the entire cluster. The cluster may also be referred to as a magnetic lattice. Described herein are methods and systems for controlling the formation of a cluster of magnetic particles, which may help normalize the analysis. In some variations, the system may apply a higher energy magnetic field (e.g., rotating magnetic field) for a brief time period to drive the formation of a regular cluster of magnetic particles. Thus, the magnetic lattices may be formed with a rotating magnetic field.

Figures 17A, 17B:
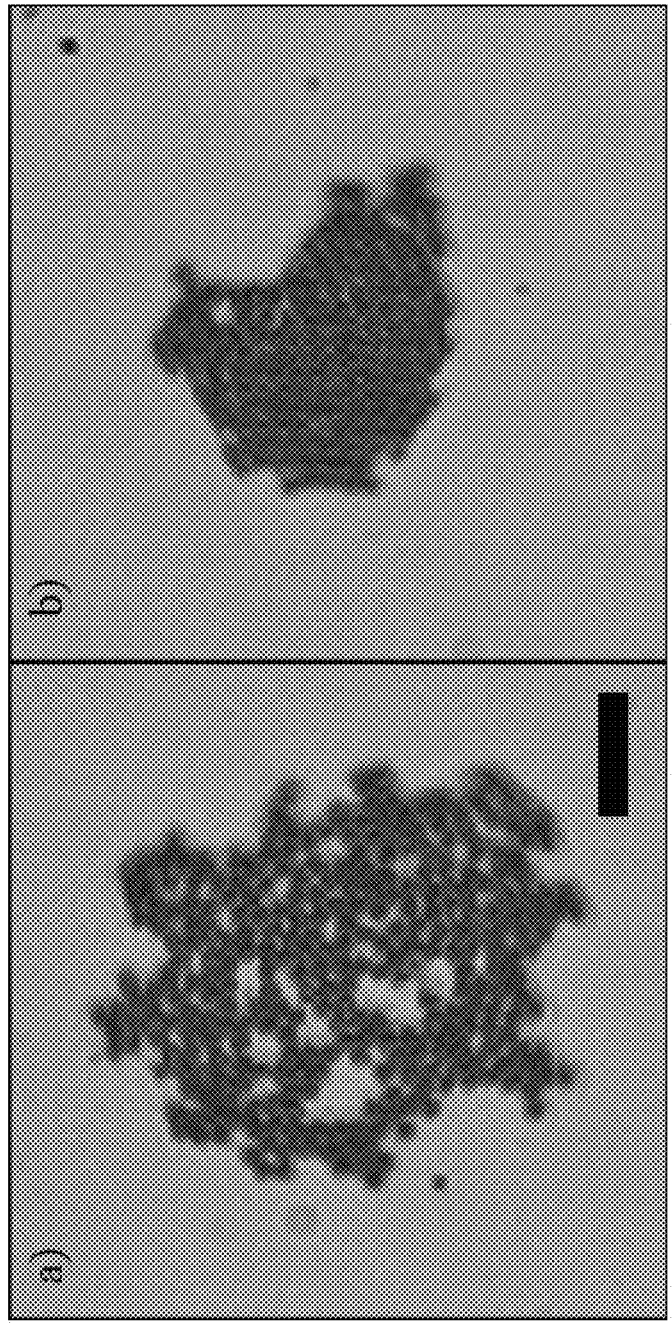
FIGS. 17a-17b illustrate formation of a stable, tightly-packed cluster of magnetic particles.

For example, a higher magnitude (e.g., 10 mT in this instance) magnetic field can be used to form tightly packed groups of group AMBR sensors. FIG. 17a shows a group of magnetic particles that was formed from 2.8 micrometer superparamagnetic particles (Invitrogen, Dynabead M280) in an aqueous casein solution. The cluster group was formed by the following procedure: first, the bead solution was deposited onto a Teflon-coated slide; second, the droplet was inverted and a permanent magnet was used to pull the beads to the bottom; and third, a 1-Dimensional field was applied to align beads into chains; finally a rotating field was applied. After the group (shown in FIG. 17a) had been rotating for 15 minutes (at which point it had reached a stable conformation), the field strength was increased by a factor of 10 for ten seconds. During the ten seconds, the group's rotation rate increased substantially. After the ten seconds, the field strength was returned to its original value and the group had changed to the more tightly-packed conformation shown in FIG. 17b.

In some variations, the step of increasing the magnetic field strength may include increasing the rate of rotation of the rotating magnetic field. In some variations, the step of increasing the magnetic field strength may include use of a 1D alternating (e.g. flipping) field. In some variations, both the strength and rate of rotation may be changed (e.g., increased) to form a stable, tightly-packed cluster. The duration of time that the rotating magnetic field is altered to form the cluster may be greater or less than 10 seconds. For example, in some variations, the strength of the rotating magnetic field is increased for 30 seconds, 1 minute, etc.

FIGS. 19A and 19B illustrate one method of forming a packed cluster of magnetic particles either before, during or after binding of cells (e.g., bacteria). In this example the magnetic particles are in solution in the well (FIG. 19A); a cluster may be formed near the bottom or apex of the curved interface by applying a static magnetic field (bar magnet 1901) to pull the magnetic particles down to the bottom of the interface as shown. Thereafter the static field may be removed, but the cluster may remain. The curved interface may also help maintain the cluster cohesion.

In some variations, the formed cluster may have crystallographic properties.

In use, cluster of magnetic beads may be particularly sensitive to the binding, growth (including both extension and division) and death of cells. For example, FIGS. 18a-18D schematically illustrates clusters of magnetic particles that may be asynchronously rotated to detect binding, growth and/or death of cells. In this example the clusters start originally as a mixture of cells bound to magnetic particles (shown in the left for FIGS. 18a-18d as identical starting conditions). During the normal growth of bacteria, as shown in FIG. 18a, the cells multiply but likely remain bound to the cluster. Thus as time goes on a relatively smooth growth curve may be measured. Alternatively if the cells are inert, as shown in FIG. 18b, neither dividing or otherwise growing, no change in asynchronous rotation will result, and thus no growth curve. In the presence of agents that encourage elongation or growth (but may inhibit cell division), as shown in FIG. 18c, the cell growth may be detected as a change in the rate of rotation caused by the expansion of the cluster and the attached cells. Finally, the opposite situation may occur when the cells on the cluster are actively removed or lysed, as shown in FIG. 18d; in this example, the cluster may actually contract, potentially increasing the rate of rotation.

Using a Camera Pixel Array to Monitor AMBR Sensor Rotation

As mentioned above, any appropriate camera may be used, generally functioning as a light-sensitive sensor or array of sensors that is configured to detect rotational motion based on the image plane.

For example, the system may include a camera comprising an array of sensors (e.g., a pixel array). In some variation, the camera may be configured as part of the system so that additional lenses are not necessary. Thus, a digital camera pixel array can be used to measure magnetic microparticle rotation without the need of lenses. In one exemplary system, by using a point light source some distance away, in this example an LED light source and a pinhole about 20 cm away as illustrated in FIG. 14B, the particle (or cluster of magnetic particles) can cast a shadow on the pixel array directly. The sample may be positioned as close to the pixel array as possible, for example, a few millimeters may be sufficient for particles with the size on the order of ten micrometers. Typically, the closer the sample is to the array, the smaller particles that can be imaged. A glass cover (covering the pixel array) does not have to be removed, and a zero thickness microscope slide can be used as a sample holder on top of that. This method is particularly well-suited to the detection of rotation of nonspherical particles, clusters of two or more particles, or particles and a cell or cell, as shown schematically in FIG. 14B.

Although this example includes the use of an LED/pinhole, any appropriate light source may be used with the system for directly imaging onto the pixel array. For example, a laser can be used as the light source, particularly if the beam is expanded. In some variations the pixel array corresponds to one or more CMOS chips. CMOS chips are typically inexpensive and the size of each pixel may be in the order of a micrometer; smaller pixels may also be possible (e.gg., in chips used in phone cameras).

In some variation the sample with the magnetic particle or magnetically-labeled cell is held within an oil-water emulsion for AMBR imaging. Typically, the oil is the continuous phase and the AMBR sensors (magnetic particles) are in aqueous droplets surrounded by oil. Simple emulsions can be generated by simply shaking the vial (which may result in a wide size distribution of droplet sizes, e.g., resulting in droplets a few microns to hundreds of microns in diameter). Oil-water emulsions may also act as lensing chambers, as mentioned above and shown in FIG. 16. The system may be configured (e.g., using microfluidics) to handle the water/oil emulsions. In some variations, the system, or a sub-component of the system (e.g., sample holder) can be configured to produce droplets of a desired (or regularized) size. An example of a microfluidic chamber for use with oil-water emulsions is described in more detail in part 8, below.

In variations in which the camera is a CMOS device, the device may measure multiple magnetic particles (sensors) or clusters in parallel. A theoretical limit for parallelization for a single CMOS is approximately 10,000 simultaneous samples (assuming a 1 cm by 1 cm CMOS chip and 100 um squared sample). For example, in some variations measurements of viscosity, cell growth, binding etc. may be made by monitoring individual multiple-pixel sized (or larger) magnetic particles using a pixel array. Alternatively, the pixel array may be used to measure properties by monitoring the rate of rotation of magnetic particles in a cluster or group. In some variations, properties may be measured (e.g., growth of a cell or a group of cells) by inducing magnetic moment by (specifically or nonspecifically) attaching magnetic nano- or microparticles to it. In any of these examples, the rotation may be detected using a CMOS, CCD, optical mouse sensor etc.

Sorting Magnetic Particles by their Critical AMBR Frequency

In some variations it may be desirable to sort the magnetic particles, for example, by separating particles with bound analyte (e.g., cells) from those that have not bound analyte. The application of an asymmetric rotating magnetic field (e.g., oval rotating magnetic field) may be used to separate magnetic particles based on their rotational properties.

Figure 20:
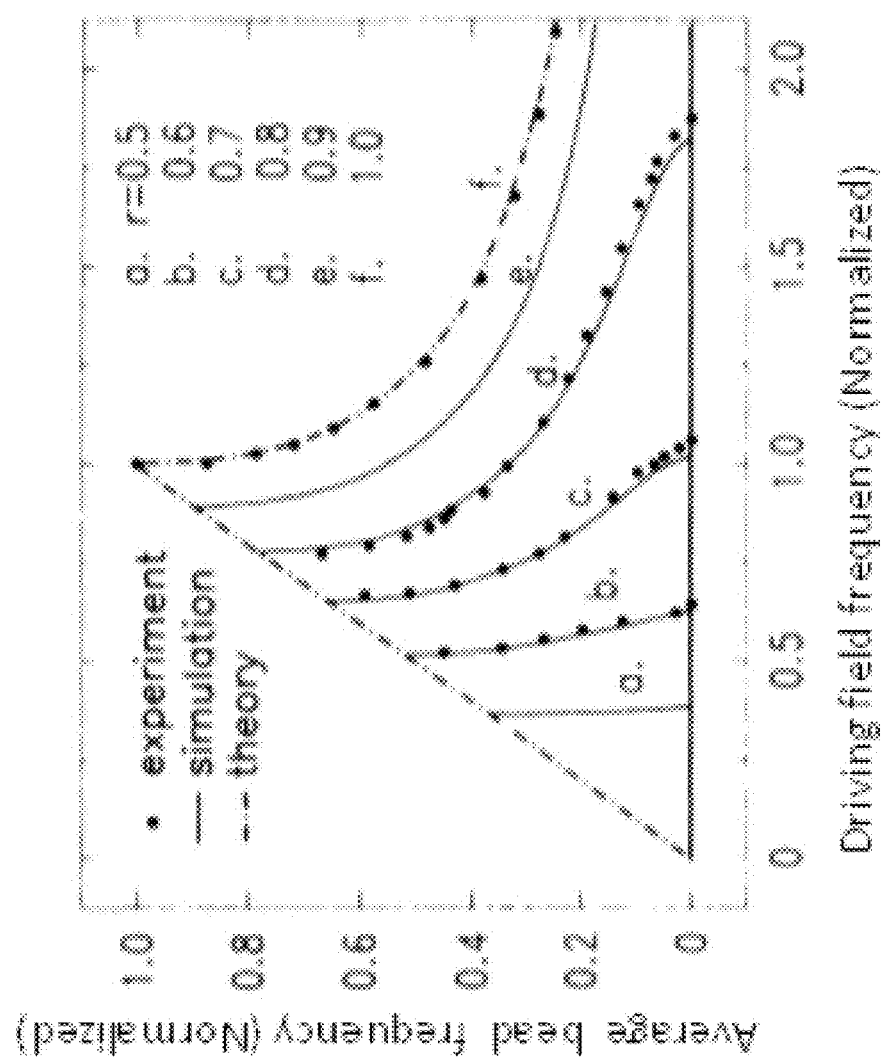
FIG. 20 shows magnetic particle rotation frequencies with varying field ovality. Where r=ratio of x component amplitude vs. y component amplitude of the magnetic field. The more elliptical the field, the lower critical and stopping frequency. This graph is adapted from G. Helgesen, P. Pieranski, and A. T. Skjeltorp, "Dynamic behavior of simple magnetic hole systems," Physical Review A 42, no. 12 (1990): 7271-7280.

For example, magnetic microparticles can be sorted by their critical asynchronous frequency by "rolling" the magnetic particles on a surface. By applying an oval rotating magnetic field, only those particles that possess a critical frequency above a certain value will rotate. When the magnetic particles are located on a surface (e.g., a flat surface), the particles may be "rolled" apart from non-rotating particles. For example, magnetic particle rotation frequencies in oval rotating magnetic fields with different x and y component strengths can be seen in FIG. 20. The critical frequency is inversely proportional to the volume of the rotating body, and therefore this method can be used to separate for example bare magnetic particles from magnetic particles with a single cell attached after binding procedure.

Although magnetic bead sorting using a typical rotating magnetic field has been described by B. B Yellen et al. ("Traveling wave magnetophoresis for high resolution chip based separations," Lab on a Chip 7, no. 12 (2007): 1681-1688), these previously described methods and techniques all required the use of micropatterned magnets. The method described herein applies an oval (non-circular) magnetic field to drive differential rotation/non-rotation and thereby separation of magnetic particles.

Figure 21B:
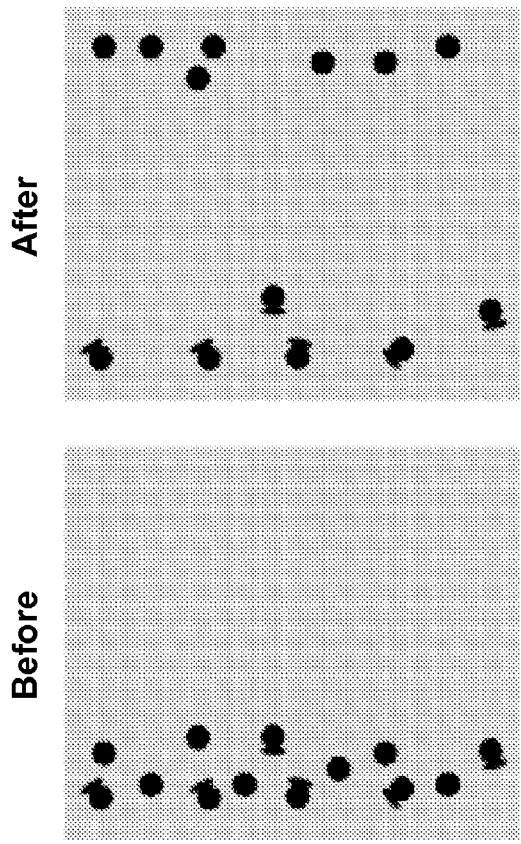
FIGS. 21A and 21B show examples of the separation of magnetic particles bound and unbound to analyte by the critical AMBR frequency, where the oval field rotates from left to right and out of the image plane.
Figure 21A:
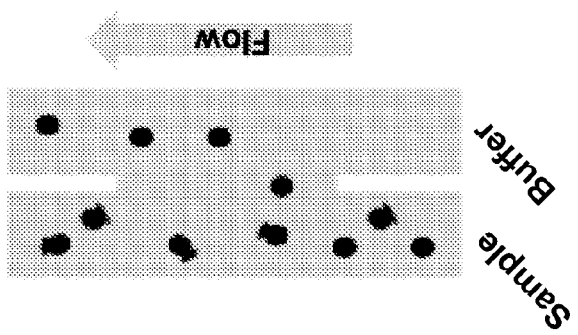

For example, FIGS. 21A and 21B illustrate one example of separation by critical AMBR frequency using an oval magnetic field. In this example, the oval field rotates from left to right and out of the image plane. The spheres shown are magnetic particles, and the ovals denote bacteria. In FIG. 21A, bare magnetic particles are separated from the ones that have a bacterium bound on a microfluidic channel; under the influence of the oval-rotation of the magnetic field, the unbound magnetic particles roll to the right of the figure, into a separate microfluidic channel, separating from the bound particles. Similarly, in FIG. 21B, a sample is shown in a microscope slide in the before (left side) and after (right side) application of an oval-rotating magnetic field. On the right the same is done on a microscope slide.

As mentioned, this method may be done with any appropriate analyte, including cells (e.g., bacteria, yeast, mammalian cells, cancer cells, etc.).

In some variations, the method for separating magnetic beads may include the use of a continuous magnetic field in addition to a rotating magnetic field, either simultaneously or sequentially. For example, in some variations, the system includes a surface on which the magnetic particles may be rolled or held, a source for a rotating (e.g., in an oval direction, as described above), and a source for a static magnetic field. The source for the static magnetic field may be the same as the source for the rotating magnetic field, operating in a "static mode" (other modes may include circular rotation and oval rotating, etc.).

Figure 21C:
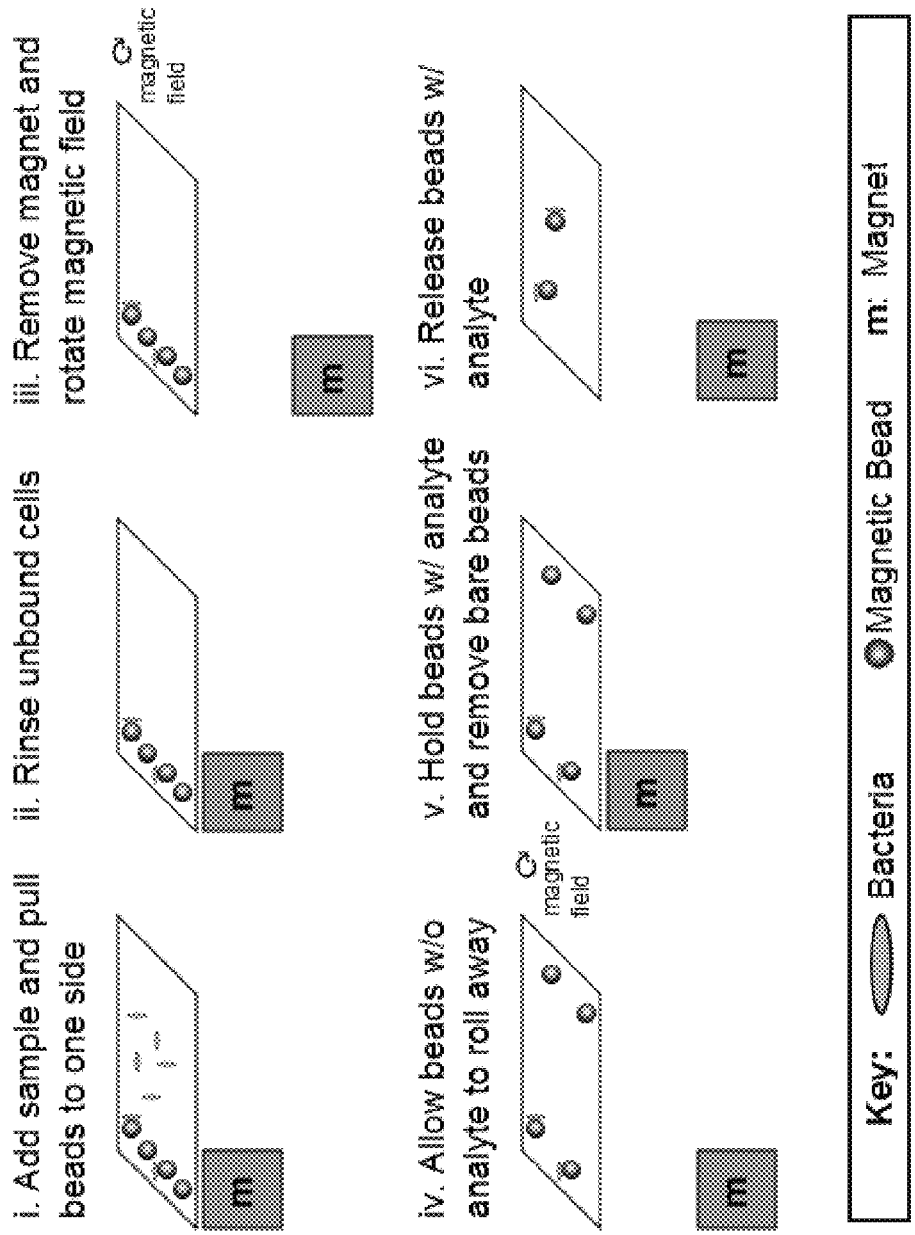
FIG. 21C illustrates one method of separating out magnetic particles bound to analyte (e.g., cells) from magnetic particles that are unbound, by the application of a non-circularly rotating magnetic field (e.g., oval magnetic field).

In some variations, the method may include a table top device, such as the variation shown in FIG. 21C, which uses a (static) magnetic force below the rolling surface to 1) position the magnetic beads and bound analyte, 2) perform an initial separation to remove unbound analyte, and 3) hold in position the magnetic beads with bound analyte while the bare beads are removed. In FIG. 21C the steps for separation are labeled "i" through "vi" and describe both a gross separation of non-magnetic particles (e.g., cellular debris, etc.) from magnetic particles by the application of the static magnetic field shown in FIGS. 5(C)(i) and 5(C)(ii), and the separation of magnetic particles that have bound analyte from unbound magnetic particles by application of an oval magnetic field, as shown in FIGS. 5(C)(iii)-5(C)(iv). Thereafter the unbound particles may be "washed away" by applying a magnetic field to hold just the bound particles, while washing away the unbound particles (e.g., those having a higher critical asynchronous frequency which will separate out during the application of the oval rotating field). The final washing steps are shown in FIGS. 3(c)(v) and 3(c)(vi).

The method for separating magnetic particles may be included in any of the AMBR procedures (and systems) described herein. For example, during magnetic isolation, only a (usually small) subpopulation of magnetic particles have a cell attached to them. In AMBR biosensor growth applications the greater the bacteria-to-beads ratio, the lower the signal-to-noise may be. Thus, it may be useful as a pre-step to isolate the subpopulation which has bacteria bound to it, e.g., providing a bacteria-to-beads ratio of (for example) at least 1. The method of sorting bound from unbound magnetic particles is not limited to AMBR, but may be used with other applications in which bacteria are bound to a magnetic particle. In some variations, magnetic particles can be sorted to isolate a homogeneous subpopulation of the particles for applications that require particle-to-particle uniformity.

Preparation of Half Coated Magnetic Particles with Tunable Density

In some variations it may be desirable to use magnetic particles that are more or less buoyant. Described herein are methods of making magnetic particles having a selected (e.g., predetermined) buoyancy.

Magnetic microparticles are widely used in the biosciences. High magnetic moment is required in many applications, however high magnetic moment also means high fraction of magnetic material. Since the specific gravity of most used magnetic materials is many times higher than water, the settling of the magnetic particles becomes an issue in some applications. Thus, it may be desirable to have more buoyant magnetic particles, or (in some variations) less buoyant magnetic particles, or magnetic particles that are neutrally buoyant (e.g., in aqueous solutions). A method to fabricate neutrally buoyant (e.g., having a specific gravity of one) magnetic particles is explained below. More broadly, the specific gravity of the particles can be tuned to the desired value by adjusting the method as described.

Figure 22A:
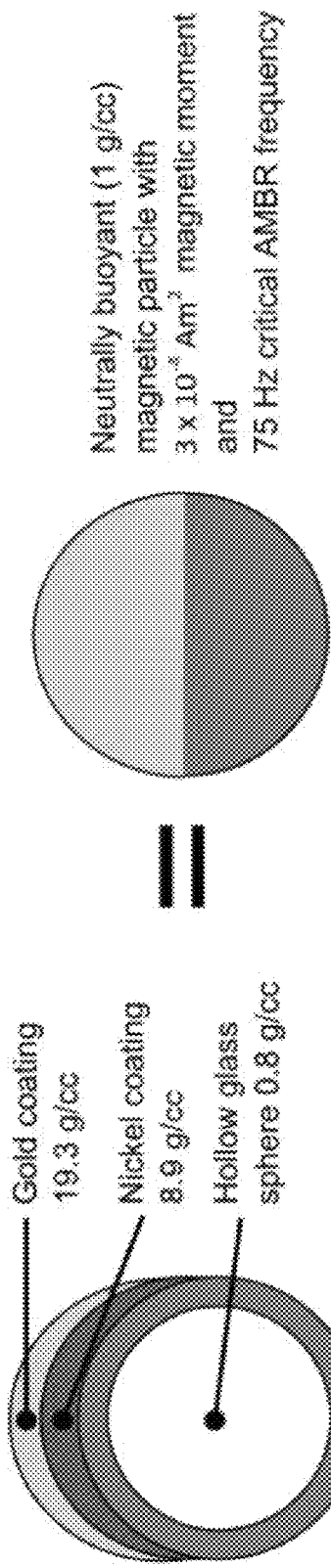
FIG. 22A illustrates the formation of a neutrally buoyant magnetic particle made by half coating a hollow glass sphere. Coating thicknesses are exaggerated for visualization.

Non-magnetic particles that have a low specific gravity can be made magnetic by coating them with magnetic material. This can be easily done with vapor deposition of Nickel or Cobalt. At the same time, the specific gravity of the particles would be increased; by adjusting (e.g., adding) the amount of coating, the density can be tuned or selected. For example, a 10 um diameter hollow glass spheres with a density of 0.8 g/cc may be turned to be neutrally buoyant by adding a 150 nm-thick layer of Nickel (8.9 g/cc) and 5 nm-thick gold (19.3 g/cc) coating. Considering that 10 um particles with 300 nm Nickel coating have $3 \times 10^{-4}$ $Am^2$ magnetic moment and 150 Hz critical frequency and that the critical frequency is proportional to the nickel coating volume, 10 um particles with a 150 nm Ni coating would be expected to have a magnetic moment and critical frequency half of those values (e.g., $1.5 \times 10^{-4}$ $Am^2$ and 75 Hz). FIG. 22A shows a schematic of this analysis.

In some variations, by using thicker gold coating than mentioned above, the particles may be made heavier than water and lighter than water with less coating, which enables the fabrication of sinking and floating magnetic particles.

Figure 22B:
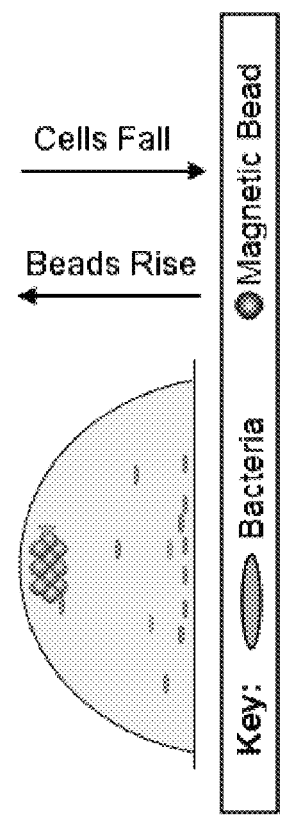
FIG. 22B illustrate one application for the use of buoyant particles.

In some variations, buoyant particles may be used to keep particles in a different location than any cellular fragments. Buoyant particles may be held at or near the top of a chamber (including at or near the top of a curved surface) so that any cellular fragments or debris (e.g., resulting from cellular death or lysis) will fall to the bottom of the sample chamber. For example, FIG. 22B shows one example of the use of buoyant particles that are lighter than water and which may be "floated" to the top of a chamber for rotation. As illustrated when the beads are rotated, debris (including unbound cells and other debris) may fall to the bottom of the chamber (by gravity), separating from the rotating particles near the top region. Thus, debris and non-target cells (e.g., bacteria) may be kept from the rotating magnetic particles, enhancing the accuracy of the AMBR procedure.

It should be noted that in some variations a static magnetic field may be used in addition to a rotating magnetic field to enhance or achieve this effect. For example, in some variations, a magnetic gradient may be used to suspend the magnetic particles (with bound analyte) as they are rotated. Thus, even neutrally buoyant or heavy magnetic particles may be suspended in this manner. For example, application of a static field (e.g., from a permanent magnet) in the presence of a rotation magnetic field may allow the magnetic particles to be suspended above the "bottom" of the chamber, so that debris may fall and separate from the rotating magnetic fields. In such variations the rotating magnetic field is applied over the magnetic gradient holding the cells "up", so that the magnetic particles rotate above the bottom of the chamber, allowing non-magnetic debris to fall to the bottom. In some variations this debris may be removed (e.g., by fluid flow).

Using an Optical Mouse Sensor to Detect AMBR Sensor Rotation

As mentioned above, any appropriate optical detector and/or optical sensor may be used to monitor the rotation of the AMBR sensor (e.g., magnetic beads), including arrays of sensor. One specific set of examples are sensors such as those used for an optical mouse. The circuitry and the detector of an optical mouse are typically used to detect the movement of a mouse by rapid image analysis. This same detector and circuitry may be used to track the rotation of an AMBR sensor, when the detector is used to image the rotation of a diffraction pattern created by a laser (or other light source) focused on the AMBR sensor.

Measuring Cell Growth by the Light Blocked by Magnetic Particles

In some variations, the methods for detecting and/or quantifying cell growth are based on AMBR and the application of a rotating magnetic field, in some variations, magnetic particles may be used to measure cell growth without applying a rotating magnetic field, in a static mode. For example, in one variation, magnetic microparticles may be used to isolate bacteria (e.g., with the use of specific antibodies) as is done in many clinical and scientific applications. After isolation, the magnetic particles can be accumulated on the bottom of an inverted fluid droplet (or other chamber, well, etc.). In a first ("AMBR" mode), the growth of the attached bacteria can be measured by measuring the rotation rate of the magnetic cluster. In some variations the system may include a second (e.g., "static" mode) wherein the bacterial growth may be monitored without rotating the magnetic particles; the bacteria growth may result in an increase the average distance between each magnetic particle as the bacteria population grows, and this growth can be measured by observing the intensity of the light from a laser (or other light source) passing through the sample. For example, if the magnetic beads are clustered to a relatively dense packing (e.g., by clustering them as described above), the densely packed magnetic particles may effectively block the light; because only a few bacteria are present and bound to the beads, the beads may pack closely together. As the bacteria grow and divide, the magnetic beads must spread apart, and cannot pack as tightly, allowing more light to pass through. Thus, in this mode, the magnetic particles may be used as a kind of "contrast agent" to make growth more easily visualized.

In some variations a static magnetic field may be applied to enhance or normalize the packing of the magnetic beads.

Thus, in some variations, bacterial growth may be measured without magnetic field present, with a stationary and expanding group. The analyte may be any cell type, including bacterial cells, cancer cells, yeast cells, etc.

Oil-Water Droplets and/or Microfluidic-Based Platforms

Asynchronous magnetic bead rotation (AMBR) may be performed on hanging droplets and on oil/water emulsions (e.g., droplets of water including the magnetic beads and analyte suspended in oil). For example an AMBR biosensor may use a droplet microfluidic platform that enables single cell and small cell population growth measurements for applications aimed at rapid antimicrobial susceptibility testing ("AST"). In one example, described in detail below, a small uropathogenic E. coli population was confined in microfluidic droplets and exposed to concentrations above and below the minimum inhibitory concentration (MIC) of gentamicin. Growth was observed below the MIC, and no growth was observed above the MIC. A 52% change in the sensor signal (i.e. rotational period) was observed within 15 minutes, thus allowing AST measurements to be performed within minutes.

The following materials and reagents were used in this example: PCR-grade mineral oil, Span® 80, and Bovine Serum Albumin (BSA); Dulbecco-PBS; Mueller Hinton II (MH Broth); dispensing tips, syringe barrels, and a barrel adapter kit; Pluronic F-68; Tygon Silicon Tubing (02-587-1D); Inlet/Outlet adapters; 8.8 μm streptavidin-coated superparamagnetic beads (8.8+0.8 μm); and Dynabead® M-280 Streptavidin-coated superparamagnetic beads (2.8+0.2 μm).

The microfluidic platform typically forms reproducibly or uniform-sized droplets of aqueous solution (e.g., media) including magnetic particles. The aqueous droplets are typically surrounded by a continuous phase that does not mix with the aqueous phase of the droplet. In this example, the continuous phase consisted of mineral oil with 1% SPAN 80 (v/v). For bead (magnetic particle) characterization experiments, the aqueous phase consisted of PBS solution: PBS with 1% Pluronic F-68 and 0.1% BSA. For biological experiments, the aqueous phase consisted of MH broth solution: MH with 1% Pluronic F-68 and 0.1% BSA, which will be referred to as MH-PB.

An example of a microfluidic device may be fabricated to include one or more channels through which the aqueous and continuous (oil) fluids may be mixed and moved to position the aqueous droplet for imaging (e.g., to monitor rotation). For example, channel geometries may be designed with software such as LEdit, to layout the design. The fabrication process may include photolithography and wet chemical etching steps, e.g., on a glass wafer, to form the channels and ports. For example, 50 nm Cr and 250 nm gold Au may be deposited onto a glass wafer; the wafer may then be patterned and the glass channels etched in hydrofluoric acid (49%) (CMOS grade) to a depth between 45 μm and 50 μm, as measured with a surface profilometer. The photoresist and metal layers may then be removed, the glass wafer diced to obtain individual devices, and inlet and outlet holes may be created with electrochemical drilling. The devices may be cleaned in Piranha solution (e.g., a 2:1 solution of sulfuric acid and hydrogen peroxide, respectively) and subsequently coated with a 2 μm layer of Parylene-C (PDS 1020 Labcoater). The devices may also be UV-glued to a 0 thickness microscope slide and inlet and outlet ports UV-glued to the device. A simplified schematic of this exemplary fabrication process is outlined in FIG. 23a and the assembled glass microfluidic droplet device is shown in FIG. 23b.

In one example, using the microfluidic device described above and in FIGS. 23a and 23b, experiments were conducted on an Olympus IX71 inverted microscope. The microfluidic device was placed inside custom-built electromagnet coils that were integrated on the microscope stage (see, e.g., FIG. 23c). In this example, the rotating magnetic field was generated with a custom LabView program and data acquisition board (NI PCI-6221). The magnetic field driving frequency range was 0.1 Hz to 1 kHz, and the magnetic field strength was 0.9 mT, as measured with a 3-axis magnetic field probe (Senis Gmbh, C-H3A-2m).

Magnetic bead characterization experiments were conducted at 21° C. Single cell experiments were conducted at 21° C., with a 100× oil immersion objective. The magnetic field driving frequency was set at 500 Hz for control and growth experiments. One-minute videos at 15 frames per second (fps) were taken in 5-minute intervals with a digital camera. Small cell-population experiments were conducted at 35° C., with a 40× objective. The microfluidic device was placed on an ITO slide that was heated and maintained at a set temperature, 35+0.2° C. This temperature was monitored by a thermocouple that was coupled to the surface of the slide with a thermally conducting silver paste, Arctic Silver 5 (ARCTIC SILVER). The magnetic field driving frequency for small cell-population control and growth experiments was set at 50 Hz, and continuous videos were taken for a minimum of 5 hours at 2 fps. For small cell-population control and antibiotic response experiments, 1-minute videos were taken at 20 fps in either 5-minute or 20-minute intervals.

As mentioned, movies were captured with a digital camera (Basler, piA640-210 gm). The videos were analyzed using ImageJ (for example, see FIG. 23d). The rotational frequency of the bead complex was determined by monitoring the fluctuations in intensity profile at the target area of interest using ImageJ's 'plot z-axis profile' functionality. This intensity plot was analyzed by applying a Fast Fourier Transform (FFT) to the raw ImageJ data in MATLAB. The experimental error in determining the rotational period was designated as the FFT peak's full width at half max (FWHM) of the amplitude signal.

Prior to experiments, the microfluidic devices were incubated with Rain-X (SOPUS Products) for at least 10 minutes to render the channel surfaces hydrophobic. The continuous phase wetted the channel walls and fully entered the channels. The hydrostatic pressure applied at the inlet of the continuous phase was controlled by adjusting the height of the reservoir. 10 μL of aqueous solution was dispensed into the aqueous inlet port. A vacuum pump was connected to the outlet. To create droplets of approximately 0.5-1 mL in volume—see, e.g., FIG. 23e, the vacuum strength was set between 70 kPa to 90 kPa and the hydrostatic pressure of the continuous phase was set between 1.2 kPa and 1.9 kPa.

In this example, the streptavidin coated M-280s and 8.8 μm magnetic beads were incubated with biotinylated anti-*E. coli* (Abcam, ab20640-1) at 37° C. for 2 hours on a shaking platform at 175 rpm. A uropathogenic clinical *E. coli* isolate was grown on Muller-Hinton agar plates (BBL) at 37° C. for 16 to 18 hours. A 2 mL vial of Mueller Hinton II (MH) broth was inoculated with bacteria to a 0.5 McFarland standard (approximately $1.5 \times 10^8$ CFU/mL). Anti *E. coli* functionalized magnetic beads, M-280 beads for single-cell growth experiments and 8.8 μm magnetic beads for small cell-population growth experiments, were introduced to the bacteria solution and the sample was incubated at 37° C. for 1.5 hours in a 1.5 mL microcentrifuge tube on a shaking platform at 175 rpm. This allowed the bacteria to bind to the beads and enter the exponential phase. The bacteria-bound beads were isolated with a magnetic separator (PickPen 1-M), washed in MH broth twice, and re-suspended into MH-PB.

In some variations, the bacteria were fixed with glutaraldehyde, an MH broth solution with 0.5% glutaraldehyde was used. Bacteria-bound beads were isolated with a magnetic separator, washed twice, and re-suspended into MH-PB with 0.5% glutaraldehyde.

Serial dilutions of Gentamicin were prepared in MH-PB broth at concentrations of 4, 16, and 32 μg/mL, and aliquots were stored refrigerated at 4° C. Before each experiment, the antibiotic solution was diluted to their final concentrations of 0.5, 2, and 4 μg/mL, respectively, by adding 350 μL MH broth experimental solution to the 50 μg/mL of the initial gentamicin aliquot solutions. The bacteria-bound beads were isolated with a magnetic separator (PickPen 1-M), washed twice, and re-suspended into the antibiotic solution. Experiments started within 20 minutes of antibiotic exposure.

Device Characterization

Compartmentalizing single magnetic beads in water droplets suspended in oil reduced bead-to-bead magnetic interaction effects, bead to surface interaction effects, and prevented the bead from translating out of the field of view. The applied vacuum pressure at the outlet and the applied pressure at the inlets determined the resultant droplet size. For the following experiments, the droplets ranged from 0.5 to 1 mL in volume. The current device design accommodated between 50 and 70 droplets (e.g., FIG. 23e). For single magnetic bead experiments, we maximized the number of droplets containing a single magnetic bead; the encapsulation process follows Poisson statistics, which can be expressed by $f(\lambda, n) = \lambda^n e^{-\lambda}/n!$, where $f(\lambda, n)$ is the frequency of observing a droplet containing n beads at a given $\lambda$ value, and $\lambda$ is the expected average number of beads per droplet (e.g. $\lambda=1$, if 1 mL droplets were formed from an aqueous solution at a concentration 1 bead/mL). Droplets were formed from aqueous solution of 8.8 μm bead at the following concentrations: $1 \times 10^5$, $5 \times 10^5$, $1 \times 10^6$, and $5 \times 10^6$ beads/mL and the number of beads observed in each droplet was counted. The data was fitted with the Poisson distribution, and the corresponding Lambda values were found to be 0.043, 0.43, 0.75, and 3.2 (FIG. 24a). Using an initial concentration of $1 \times 10^6$ beads/mL ($\lambda=0.75$), we obtained single beads in 35% of the droplets formed.

The frequency-dependent rotational response of the 8.8 μm and M-280 magnetic beads isolated in individual droplets were characterized with AMBR at driving frequencies between 0.1 Hz and 1 kHz. The rotational behavior of the 8.8 μm beads was dominated by its permanent dipole for frequencies up to 1 kHz, whereas the rotational behavior of the M-280 beads was dominated by its permanent dipole at frequencies below 10 Hz and by induced dipole above 10 Hz (FIG. 24b). The rotational responses of fifty plain 8.8 μm magnetic beads were observed at 50 Hz driving frequency (FIG. 24c), and the average rotational period was determined to be 2.12±0.62 s, resulting in a magnetic responsiveness variability of 30%. Similar variability in magnetic responsiveness has been reported previously.

Under controlled environmental conditions, the rotational rate of a magnetic bead is expected to be time-independent. The rotational periods for single 8.8 μm beads and single M-280 beads were monitored for 2 hours. The rotational response varied by 5% for the 8.8 μm beads and by 3% for the M-280 beads, as shown in FIG. 24d. The sensitivity of the system was taken to be the minimum effective volumetric change needed to observe a change in the bead's rotational response (greater than the 5% experimental error observed for the 8.8 μm beads and the 3% experimental error observed for the M-280 beads, see above), corresponding to 0.09 μm sensitivity for 8.8 μm beads, and 0.03 μm sensitivity for the M-280 beads. Since the bead sensitivity was largely dependent on the initial bead diameter, the size choice of the magnetic bead is application dependent.

Single Bacterium Growth Measured with AMBR

Monitoring single cell growth with high sensitivity without the influence from neighboring cells is of interest in scientific and clinical applications such as cell heterogeneity, bacterial persistence and cellular kinetics. M-280 magnetic beads were used to monitor single bacterium growth and division events, as the smaller beads were more sensitive for monitoring smaller cell volumetric changes. The average size of an *E. coli* bacterium is 2 μm in length and 0.5 μm in diameter, which is comparable in size with a M-280 magnetic bead. In this system, nanometer growth was detectable by measuring changes in the bead s rotational response.

The schematic of the growth and division process for a single bacterium at 20° C. is presented in FIG. 25a. The corresponding changes observed with light microscopy and rotational response measurements are shown in FIG. 25b and FIG. 25c, and are in good agreement. Since the effective volume is dependent on the shape factor and the volume of the rotating body (AMBR biosensor), the time at which a substantial change can be observed depends largely on the orientation of the bacteria on the bead. For the case in which the bacterium was bound at one end and grew perpendicularly to the magnetic bead (FIGS. 25a and 25b), a 17±1% change in the rotational period was observed within 5 minutes (FIG. 25c), which is above the experimental error of 3%. From the time at which the rotational rate was first monitored until the time at which the bacterium divided (103 min), the rotational period increased by 400%.

The substantial drop in rotational period (reduction in the sensors effective volume) that was observed at 103 minutes corresponded with bacterial division. As a control, a single bacterium that was attached to a magnetic bead was fixed with glutaraldehyde and the rotational response was measured. No substantial change in the bead's rotational period was observed in 2 hours, which indicated a lack of growth (FIG. 25c). As a result, we concluded that the observed changes in the rotational period of the AMBR sensor were indeed due to the growth, or elongation, of a single bacterial cell. These findings correspond well with a previous study on single cell growth with AMBR biosensors.

Small Cell-Population Growth Measured with AMBR

To monitor small cell-population growth, 8.8 μm magnetic beads were used since the larger surface area provided greater binding capacity. Experiments were conducted at near physiological conditions, 35° C., and therefore, bacteria replication time was substantially reduced as compared to the single cell growth experiments. The growth of a small population of bacterial cells attached to a bead was measured with AMBR, as shown in FIG. 26a. As the bacteria grew and divided, some daughter cells re-attached to the magnetic bead and some remained detached, free-floating in the solution (FIG. 26a). Daughter cells that re-attached to the bead increased the bead's effective volume, which was observed by an increase in the rotational period (FIG. 26b). An 8±0.3% average increase in the rotational period was detected after 5 minutes, which is above the 5% experimental error (FIGS. 26a and 26b). As a result, the concentration of bacteria in the liquid environment exponentially increased. To ensure that the initial increase in rotational period was indeed a result of growth, the rotational period was monitored for bacteria-bound beads that were fixated with glutaraldehyde. A 3% variation in rotational period was observed for fixated bacteria, which was consistent with the control experiments for beads without bacteria. Therefore, the measured changes in the rotational period are attributed to bacterial growth.

Small Cell-Population Growth Response to Gentamicin

The AMBR droplet microfluidic platform was tested with respect to AST applications by measuring the growth response of a small population of uropathogenic *E. coli* towards gentamicin, a bactericidal antibiotic that interrupts protein synthesis. The effects of the antibiotics on the growth of the bacteria could be discerned within an hour. Bacteria bound to 8.8 μm beads were grown in 0, 0.5, 2, and 4 μg/mL concentrations of gentamicin, and the rotational periods of the beads were monitored for a minimum of one hour. Data for the first 50 minutes are presented in FIG. 26c. An increase in rotational period was observed for the bacteria cultured in 0 and 0.5 μg/mL gentamicin, which indicates bacterial growth. No substantial change in the rotational period was observed for the bacteria cultured in 2 and 4 μg/mL gentamicin, which suggests a lack of growth. The estimated MIC as determined with AMBR is consistent with the MIC value of 1 μg/mL, as determined with the Vitek 2 system (bioMérieux, Inc). A 100% difference in the rotational period between bacteria that were treated with gentamicin above and below the MIC was measured within 25 minutes. After only 15 minutes a 52% difference in the rotational period was observed. The rotational trend observed for bacteria treated with gentamicin above the MIC was indeed similar to the results for bacteria fixed with glutaraldehyde. With the presented AMBR microfluidic droplet platform, antimicrobial susceptibility results were obtained within 30 minutes (15 minutes for sample preparation and 15 minutes for AST measurements). The high sensitivity of this method suggests the potential usefulness of the AMBR microfluidic droplet platform sensor for rapid MIC measurements.

In these experiments we have demonstrated an AMBR biosensor microfluidic droplet platform that could have significant clinical importance, especially with the incorporation of high-throughput capabilities, portability, and reduction of cost. Large-scale analysis on single cells, or small populations of cells, is possible through the use of surfactants that allow droplets to be closely packed or through structures that enable parallel experiments. This will enable the study of cell heterogeneity and behavior at the single cell level and MIC tests to be conducted on small cell populations. Microfluidic device technologies to study single cells or small cell populations exist, nevertheless, most phenotype based systems are limited to direct microscope examination and analysis. Cantilevers provide a non-microscopy, highly sensitive technique to measure growth, but these systems require labor-intensive fabrication procedures, in addition to expensive and precisely controlled equipment. The AMBR biosensor can be integrated with a low-power laser and photodiode, which will eliminate the need for expensive and complicated microscope set-ups and increase the portability of the system. Furthermore, the microfluidic device can be fabricated from PDMS, which would substantially reduce the time and cost of fabrication.

The presented AMBR microfluidic droplet platform enables single cell and small cell-population growth to be rapidly monitored. This platform could be extended towards application for AST, to measure the MIC values. The droplets provide magnetic and hydrodynamic isolation between AMBR sensors and allow a single sensor to be monitored continuously for hours. Single cell growth and division events and small cell-population growth, in the absence and presence of antibiotics, was detected by measuring changes in the magnetic bead's rotational response; the results were verified with optical microscopy. We functionally characterized a uropathogenic clinical *E. coli* isolate response to antibiotics in less than 15 minutes and estimated the MIC to be between 0.5 to 2 μg/mL, a value that is consistent with clinical results. Further development of this platform could substantially reduce the current standard phenotypic AST measurement time (6-24 hours), potentially to below 15 minutes.

As an alternative to the use of a microfluidic device, it may also be possible to form water in oil droplets (i.e., an emulsion) by simply mixing water and oil by vigorous shaking, or using a blade etc. to mix.

In some variations, magnetic bead rotation sensors can be used in continuous flow microfluidic channels, by trapping magnetic bead sensor(s) in hydrodynamic traps, wells, and physical force. The rotation can be measured with a microscope, a laser-photodiode combination, or magnetic sensors (e.g. GMR, Hall sensors).

Example Measuring the Presence of Bacteria in Blood Using AMBR

In some variations the sample of material used to detect cellular growth (e.g., bacterial growth) may be taken directly from the patient, and may not need substantial preparation. The sample examined may be blood, urine, saliva, cerebrospinal fluid, or the like. For example, in one variation the sample is blood, and the AMBR system may be used to rapidly detect bacteria. In this example, the functionalized magnetic particles (e.g., the AMBR sensor) may be introduced directly into a patient specimen (e.g., blood). For example, magnetic particles configured to bind to bacteria (e.g., having antibodies or other functional groups configured to bind specifically or non-specifically to bacteria) may be mixed with the blood. In some variations anti-cogulats (e.g., heprin) and/or surfactants may also be included to minimize inhibition of rotation of the magnetic particles. The asynchronous rotation of the particles under a rotating magnetic field (e.g., at 100 Hz) may be examined to determine if there is any cellular growth in the sample. Since the normal content of the blood does not grow, growth (even if the beads are not specifically functionalized to bind bacteria) may indicate the presence of bacteria or yeast within the sample.

As mentioned, the sensor (magnetic particles) may be functionalized with specific antibodies, or the growth can be measured as described below (in part 10), via non-specific binding.

Additional Ways to Measure the Growth of Bacteria with AMBR

The growth of bacteria (and other micro-organisms) can be measured even if the AMBR sensor is not functionalized with specific antibodies. Example 1. The AMBR sensor particles can attach to bacteria by nonspecific binding (electrostatic, protein interactions etc.), after which their growth can be monitored. Example 2. The particles do not need to be attached to the bacteria at all. Preliminary studies suggest that the growth of bacteria can be measured using the AMBR sensor, even if the bacteria are not attached to the sensor. Viscosity of a solution can change due to 1) bacterial motility in some experimental conditions, 2) sedimentation, 3) the presence of bacteria (even if not motile), 4) biofilm formation. For example, biofilm formation may affect the rotation rate; thus the system may be configured to detect and measure biofilm formation.

Speeding Up the Bacterial Growth in Combination with the AMBR

Any of the systems described herein, and particularly the AMBR systems, may be adapted to enhance bacterial or cellular growth. For example, the systems described herein may include one or more cambers to regulate the temperature, humidity, gas mixture, pressure, and any other environmental parameter that may help regulate cellular growth. For example, in some variations the system includes an incubation chamber into which the sample chamber may be kept for growth during or between monitoring. In some variations the system may be further configured to speed up cellular (and particularly bacterial) growth. Bacterial growth may be sped up while monitoring its growth by changing the temperature, media, rotation rate, and/or oxygen content of the media. For example, increasing the rotation rate may allow the bacteria to have access to more nutrients; optimizing the temperature or droplet size may also enhance bacterial growth.

Forming Droplets by Dipping

As mentioned above, the systems described herein may be used with a hanging droplet system for growth and monitoring of cells. In addition to the microfluidic chambers described above, in some variations, hanging droplets may be formed by one or more chambers that are dipped in a solution including the sample (e.g., having suspended cells) and, in some variations, the functionalized magnetic particles (AMBR sensors). The dipping process may form the hanging drops containing beads. In an automated system, the hanging drop may be formed and positioned so that it may be monitored continuously or periodically; the drop may be contained within an environmentally controlled chamber (e.g., to regulate humidity and/or temperature, thereby maintaining the drop).

For example, in one variation, a material that has holes on the order of millimeter diameter (e.g., a mesh, etc.) may be dipped in aqueous solution to form droplets. Using this method, it is possible to form arbitrarily large number of droplets in a quick and reproducible manner. In some variations magnetic particles may be included in the solution. In some variations, magnetic particles may be dried onto the mesh, or introduced later. The droplets can be used as AMBR sensor sample holders, and/or as lenses, as described above. In some variations the mesh material is stretchy (e.g., rubber, etc.), allowing the size and form of the droplets to be changed after the formation of the droplet, thereby modifying the lensing properties of the hanging drop chamber. This may therefore allow some focusing of the hanging drop "lens".

Example Integrated and Automated Systems

Figure 27:
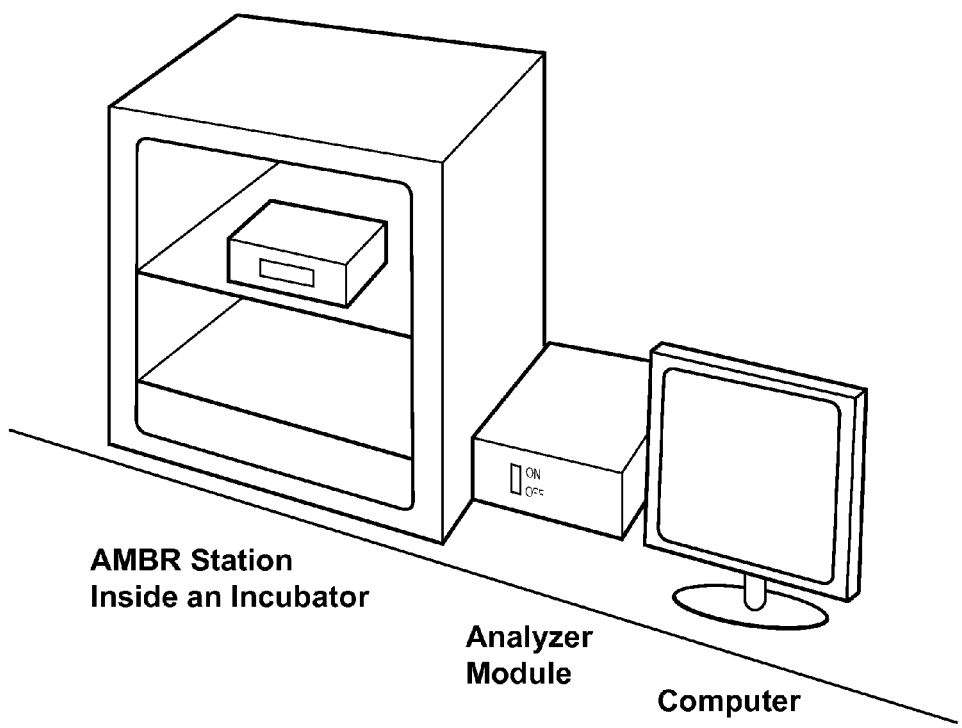
FIG. 27 shows one variation of an AMBR system configured for use within an incubator.

FIG. 27 illustrates one variation of an integrated and automated system for monitoring asynchronous magnetic bead rotation to determine cell binding and/or growth. In this example, the system is configured for use at least partially within an incubator. This exemplary system includes an AMBR station module that is configured to be positioned within the incubator, an analyzer module, likely containing a processor for receiving information from the optical sensor of the AMBR station module, and a computer, which may display, store, transmit or modify the date received from the system, including the analyzer module.

In general, the AMBR station module may include a sample chamber configured to hold a multiwell sample plate, a driving magnetic field source configured to apply a rotating magnetic field to drive asynchronous rotation of magnetic particles within a plurality of wells of a multiwell sample plate within the sample chamber; and an optical detector configured to optically detect rotation of magnetic particles from a plurality of wells of a multiwell sample plate within the sample chamber. The module may be surrounded completely or partially by a housing, and may be positioned within an incubator as shown. In some variations the optical detector also includes at least some processing capability (e.g., a processor) for interpreting the optical data to determine rotation of the magnetic particle cluster(s). The system may also include a control processor for coordinating the automated actions of the system, including maintaining the rotating magnetic field(s), collecting data on the rotation rate(s), and storing/transmitting/processing data. A control processor may be included in any of these modules.

In addition to the variation shown in FIG. 27, in some variations the AMBR station is integrated with the Analyzer module in whole or in part; in some variations the analyzer module and/or the AMBR station may include a computer or microprocessor.

Other variations of AMBR systems as described herein may be configured to be part of or to include an incubator or incubation chamber. For example, the sample chamber may be temperature-regulated, humidity-regulated, and/or gas mixture regulated (e.g., oxygen/carbon dioxide mix, etc.).

Figure 28:
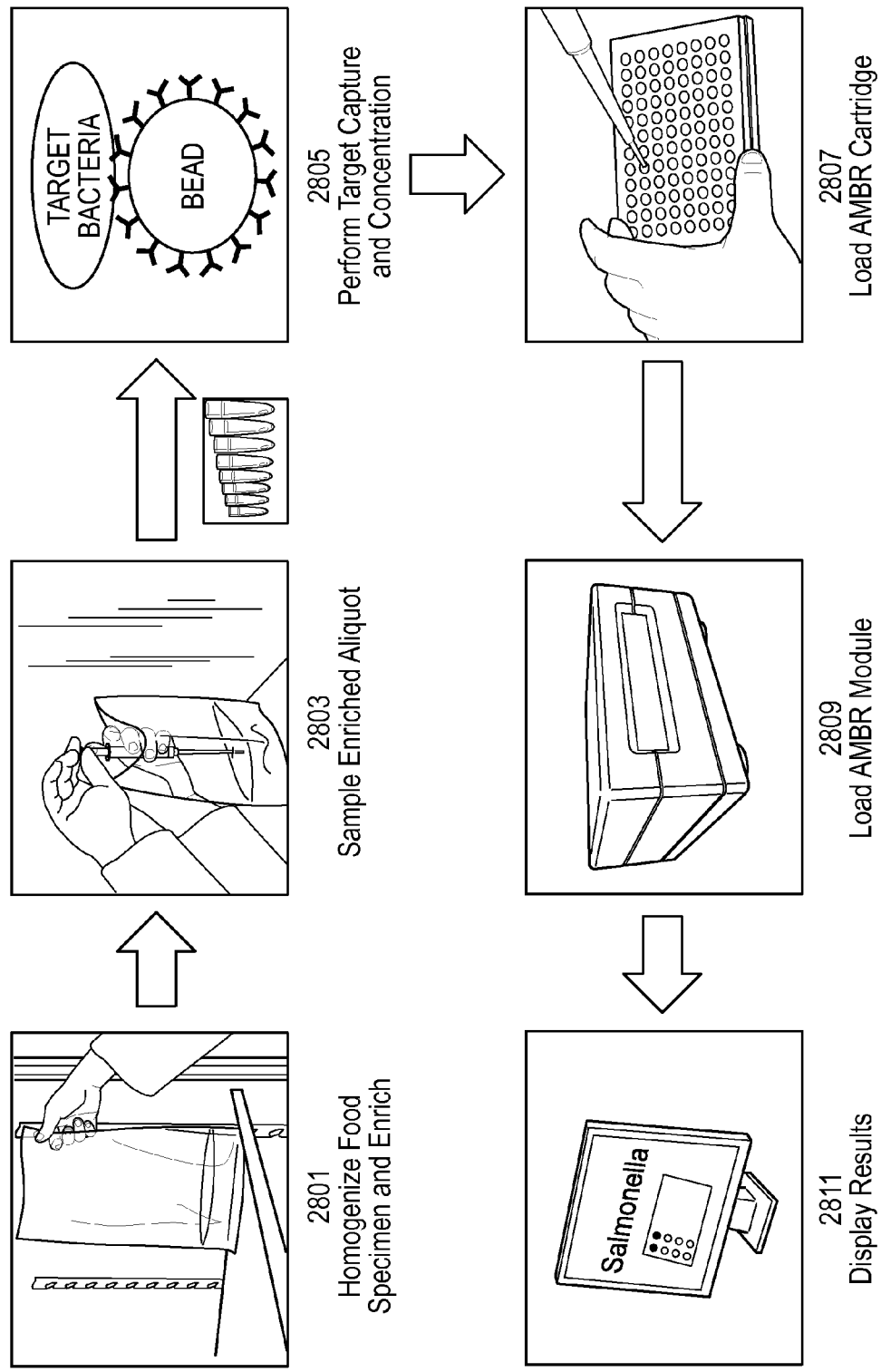
FIG. 28 illustrates one variation of a method of testing for food borne pathogens using AMBR as described herein.

In use, the systems described herein may be used to perform biological assays including, but not limited to, drug screening assays, toxicology assays, and food borne pathogen assays. For example, FIG. 28 illustrates one method of performing a food borne pathogen assay using the devices and methods described herein. In this example, a food specimen to be tested is first prepared so that any bacteria present may be bound to the magnetic particles. The magnetic particles may be first pre-treated to bind to the bacteria being examined. For example, the food sample may be homogenized 2801 and an aliquot of the homogenized sample enriched (e.g., by incubation in appropriate medium) 2803. Thereafter, an aliquot may be combined with the magnetic beads; alternatively this step may be performed prior to enrichment so that enrichment occurs in the presence of the beads. Thus, any target bacteria present may be bound to the beads 2605; the beads may then be washed and concentrated by magnetic separation. These beads and bound bacteria may then be aliquoted into wells of a multiwell plate having a curved interface, as shown 2607. The sample plate with multiple wells loaded may be incubated within the AMBR system module and clusters formed (or already formed) may be rotated by a driving magnetic field so that the clusters rotate asynchronously 2609. During the course of the observation period (typically less than 24 hours, less than 20 hours, less than 16 hours, less than 12 hours, less than 8 hours) the rotation rate of the clusters may be observed and tracked to determine if binding and/or growth is observed.

In this example it may be particularly helpful to observe cell growth, rather than division (copy). Thus, a specific growth accelerating agent may be used. For example a specific growth accelerating agent may be an antibiotic. Other specific growth accelerating agents are described above (e.g., cold, nutrient removal, high osmolarity, etc.) which may enhance "swelling" or elongation of the cells but may actually prevent them from dividing.

Figure 29:
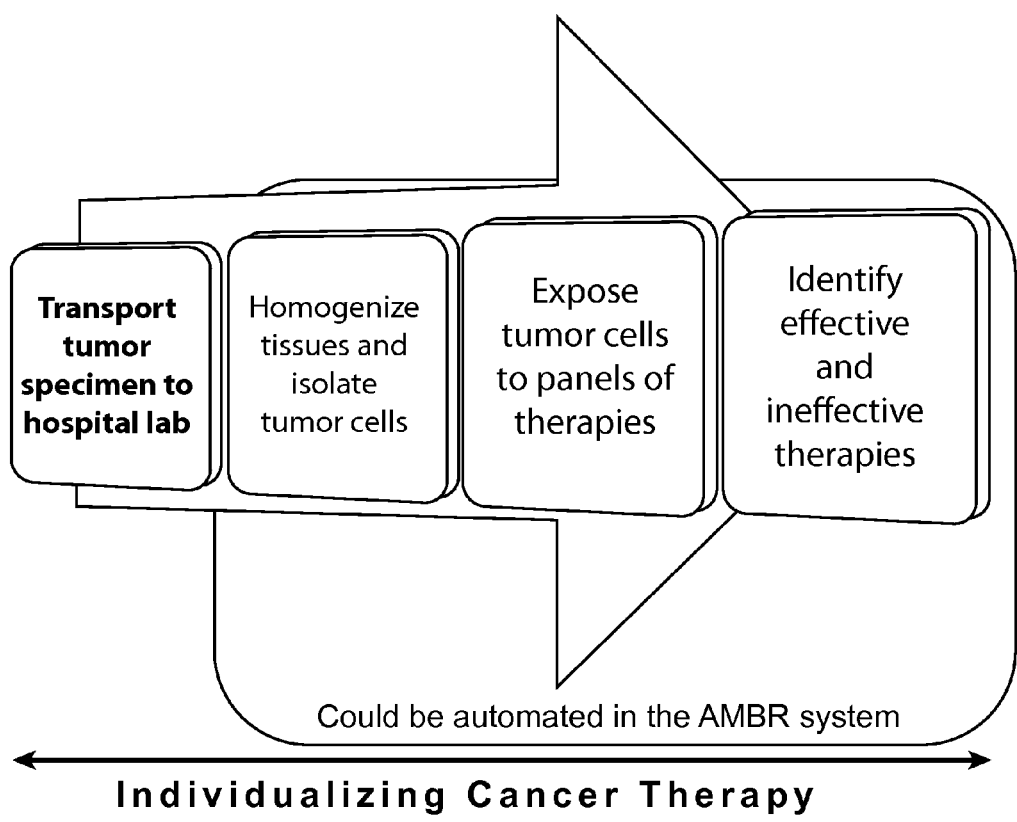
FIG. 29 illustrates one variation of a method of determining an individualized cancer therapy using the AMBR system as described herein.

Another application of the methods and systems described herein are shown in FIG. 29. In this example, a method of determining an individualized treatment regime is shown. Initially a sample of a patient's tumor is taken; this sample may be homogenized or otherwise prepared so that individual or small groups of cancer cells may be bound to magnetic particles and concentrated as mentioned above, by magnetic separation. The magnetic particles with bound cancer cells may then be placed into a system for applying an AMBR analysis. The analysis may be done in parallel within a number of wells of a multiwell plate. In some variations each well or groups of wells may include one or more potential drug therapies for treating the patient's cancer. Multiple concentrations or other conditions may be examined in parallel as clusters of cells are monitored for evidence of growth and/or swelling in the presence of potential drug therapies. In this way optimal drug therapies may be determined in parallel.

Exemplary System Components

The various device and systems described above typically include a chamber adapted for holding a sample plate (e.g., a multiwell plate), a driving magnetic field source configured to apply a rotating magnetic field to drive asynchronous rotation of magnetic particles within a plurality of wells of a multiwell sample plate within the sample chamber; and an optical detector configured to optically detect rotation of magnetic particles from a plurality of wells of a multiwell sample plate within the sample chamber. Each of these elements may be embodied in a number of different or related variations. For example, FIGS. 30A-E illustrate various light sources which may be used as part of the optical detector.

In general, the optical detector typically includes an emitter (e.g., light source) for illuminating the rotating magnetic particles, and a detector or optical receiver for detecting rotation of any magnetic beads or cluster of beads. In FIGS. 30A-E, variations of laser light sources are illustrated. As mentioned above, the light sources that may be used are not limited to laser lights sources; other sources of light may include LEDs. The light source may be collimated or un-collimated.

In multiwell variations of the systems and devices for monitoring asynchronous magnetic bead rotation, the optical sensor may be configured for parallel sensing of multiple wells of a sample plate. The optical detector may therefore have either a plurality of emitters (light sources) for optically detecting rotation of a magnetic particle/bead or a cluster of magnetic particles in a plurality of wells, or the light from a single emitter may be divided up to illuminate a plurality of different wells.

Figure 30B:
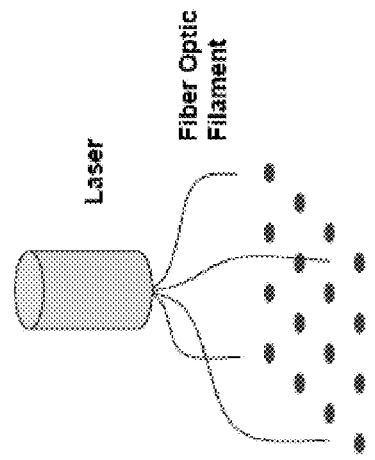
FIGS. 30A-30E show different variations of emitters (light sources) that may be used as part of a system for monitoring asynchronous magnetic bead rotation.
Figure 30D:
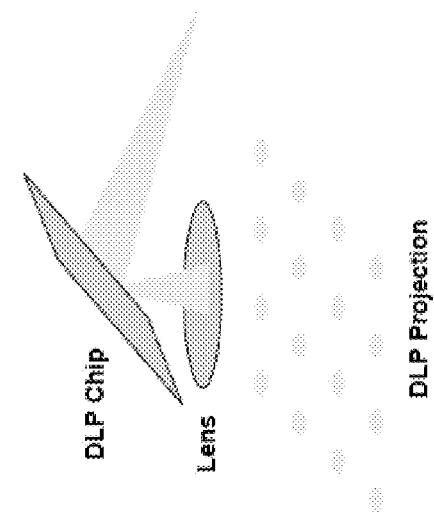
Figure 30A:
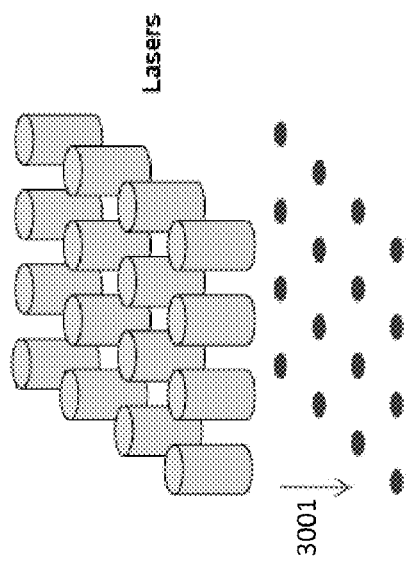

In FIG. 30A an array of laser light sources may be configured to illuminate an array of sample wells holding magnetic particles. In this example each of the wells may be coupled to receive light 3001 from its own laser light source (though note that non-laser light sources such as LEDs may be used). A fiber optic filament may be used to direct light into each well from the laser, or they may be directly coupled. Alternatively, as shown in FIG. 30B, fewer light sources (e.g., shown as a single laser light source in FIG. 30B) may be coupled to multiple wells using a fiber optic or light waveguide. This may allow for tighter packing of the matrix of wells. When a fiber optic element is used the light source may be positioned off-axis, also allowing for a more compact design.

Figure 30C:
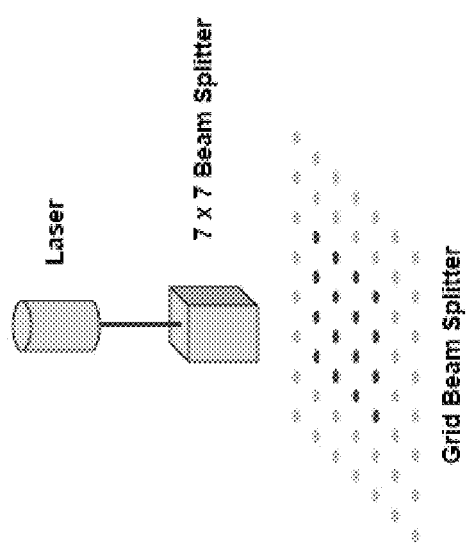
Figure 30E:
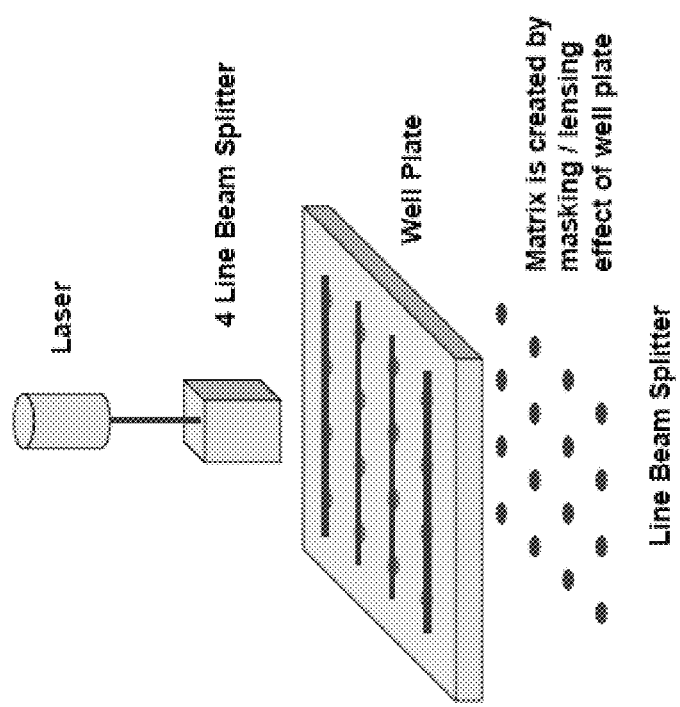

FIGS. 30C and 30D show alternative ways to divide the light from a single source so that it may illuminate multiple wells. In FIG. 30C, the light from the light source (shown as a laser) is directed to a 7×7 beam splitter, though any appropriate dimensioned splitter may be used, and directed into each well. A mask on the beam splitter may be used to select the number of wells/position of the wells illuminated. Similarly, in FIG. 30D a single light source may be directed into a minor and/or lens for directing and (in some variations) focusing the light, which may be rapidly scanned over the mirrors. In the example shown in FIG. 30D the system uses a DLP chip and lens to illuminate multiple wells.

In some variations a light source and line splitter are used with a mask to illuminate an array of wells. In the example shown in FIG. 30E, the 4 line beam splitter projects directly onto the plate; the upper surface of the plate acts as a mask, and only the light passing through the wells is passed onto the detector surface below the plate.

Figure 31B:
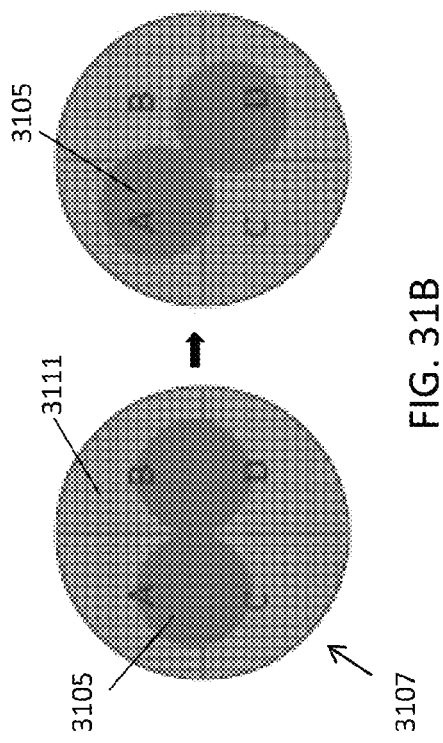
FIGS. 31A-31D illustrate different detectors that may be used as part of a system for monitoring asynchronous magnetic bead rotation.
Figure 31D:
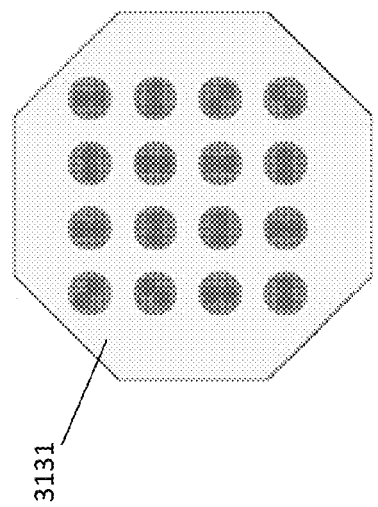
Figure 31A:
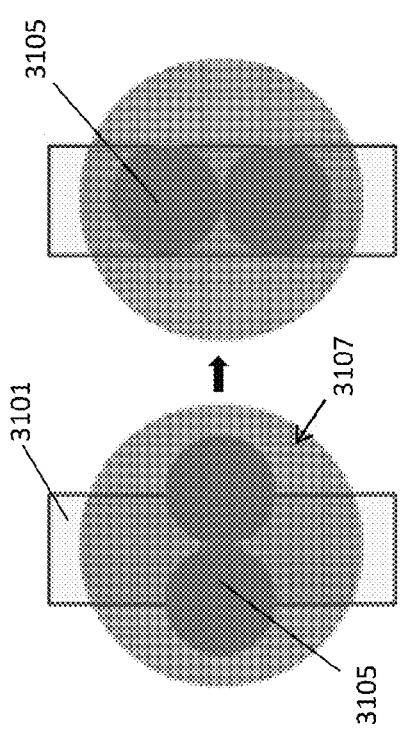

Any appropriate detector may be used in conjunction with the emitter as part of the imaging sensor for detecting rotation of the magnetic particles. For example, detectors may be photodiodes, pixel arrays (e.g., CCD, CMOS etc.). FIGS. 31A-31D illustrate various types of sensors that may be used. In FIG. 31A a rectangular photodiode 3101 may be positioned below the well, so that the illuminated region 3107 is approximately centered on the photodiode. As the magnetic particles 3105 (e.g., cluster 3105) rotate, more or less light from the illumination source is blocked by the rotating magnetic particles, and the photodiode produces a current that reflects the rate of rotation. The right side of FIG. 31A is a first time point during the rotation of the cluster 3015 and the left side of FIG. 31A is a second time point. FIG. 31B shows an example of a quadrant photodiode 3111 which has four quadrants (A-D); the current from each quadrant may be separately monitored to determine rotation of the magnetic particle 3105. The entire photodiode in this example can be illuminated 3107.

Figure 31C:
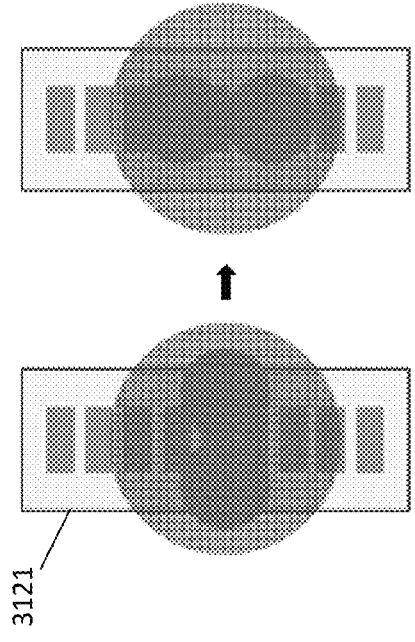

A photodiode array 3121 may be used for a single well, as illustrated in FIG. 31C. The array includes a plurality of individual ("smaller") sensing regions that may be partially or completely blocked as the magnetic particles rotate. In some variations a CCD or CMOS array 3131 may be used, as shown in FIG. 31D beneath all (or a subset of) the wells. In any of these variations the detector detects the movement of shadows (or other optical effects, such as scattered light, reflected light, etc.) of the rotating particles as they rotate.

Any appropriate driving magnetic field source may be used with the systems and devices for monitoring asynchronous magnetic bead rotation. In some variation the source is configured to apply an overall rotating magnetic field covering all of the wells of the plate; alternatively, the driving magnetic field source may be configured so that a plurality of, in some variations independently controllable, driving magnetic fields may be applied to different wells or subsets of wells. An example of this was described above with reference to FIGS. 5 and 6.

Another example of a driving magnetic field source for driving asynchronous rotation of the magnetic particles is shown in FIGS. 32a-c. In this variation (and see also FIGS. 1a and 12-13B), the driving source is a set of Helmholtz coils may be place around the plurality of wells (or single wells) and energized to create a circular magnetic field. For example, two pairs of Helmholtz coils (A and B in FIG. 32a-c), oriented perpendicular to each other are energized 90 degrees out of phase, to produce a square area of rotating magnetic field approximately $\frac{2}{3}R$ per side, where R is the radius of one of the coils. Multiple windings per coil may be used to alter the current and heat from each coil. FIGS. 32b and 32c shows side and side perspective views, respectively, of a plate within the driving magnetic field source of FIG. 32a. Light is shown projecting from the light source above the plate, through the wells of the plate, and down onto the optical detector.

FIG. 33a-c shows another variation of a driving source configured as a grid, for simultaneously applying a rotating magnetic field to a plurality of wells. In this example, the wells are arranged in an "X" pattern, and a grid of 16 rods is arranged beneath (or embedded within, or place above) the plate. Each rod has a coil on both ends. In FIG. 33a, the right to left (horizontal) rods are 90 degrees out of phase with the top to bottom (vertical) rods; rotating magnetic fields can be created at the intersections of the rods. Since the magnetic field may vary linearly along the rod, the wells may be arranged in an X configuration to ensure a constant magnitude magnetic field. FIG. 33b shows a side view of the driving magnetic source positioned beneath a well plate; the light source is shown above the plate, and a detector may be positioned below. FIG. 33c shows a side perspective view of the driving magnetic source with a multiwell plate and light source. In FIGS. 33b and 33c the light is shown passing through the wells.

Figure 35:
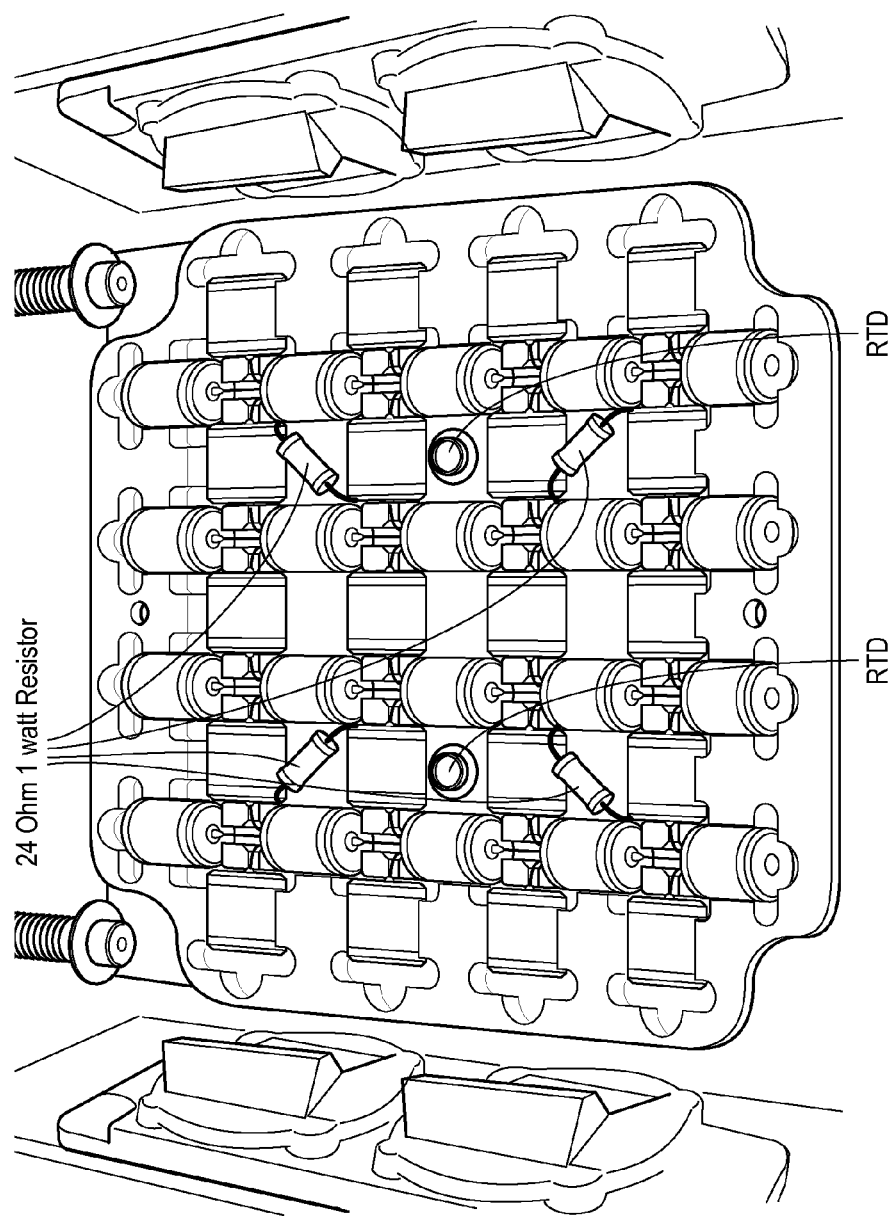
FIG. 35 is an exemplary driving magnetic field source similar to the variation shown in FIGS. 34a-c.

As shown in FIGS. 5 and 6, the driving magnetic field source may be configured similar to a synchronous motor (e.g., using inductors). Another example is shown in FIGS. 34a-c, in which each of the 16 wells of the plate are partially surrounded by four coils, spaced 90 degrees apart, each of which may be energized 90 degrees out of phase to produce a rotating magnetic field. The inner coils may each drive two wells, alternating their north and south poles. FIGS. 34b and 34c side and side perspective view, respectively. Light from the light sources pass through the wells and down onto a detector (not shown). FIG. 35 illustrates a prototype following the design shown in FIGS. 34a-c. A sixteen well plate may be placed atop this driving magnetic field source. In some variations (illustrated below) the wells of the plate may be positioned between the coils.

Figure 36:
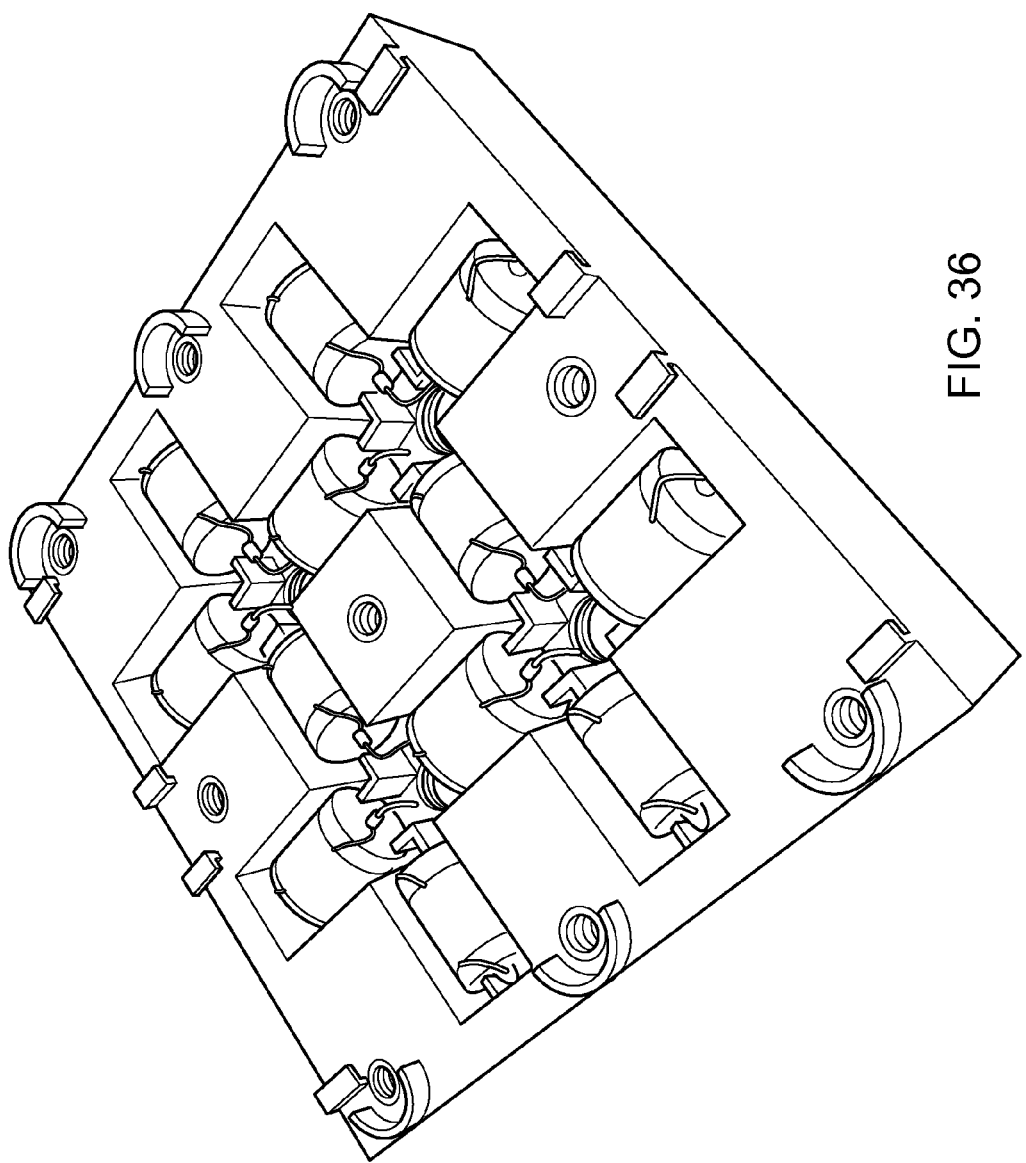
FIG. 36 is another example of a driving magnetic field source similar to the one shown in FIGS. 34a-c.
Figure 37A:
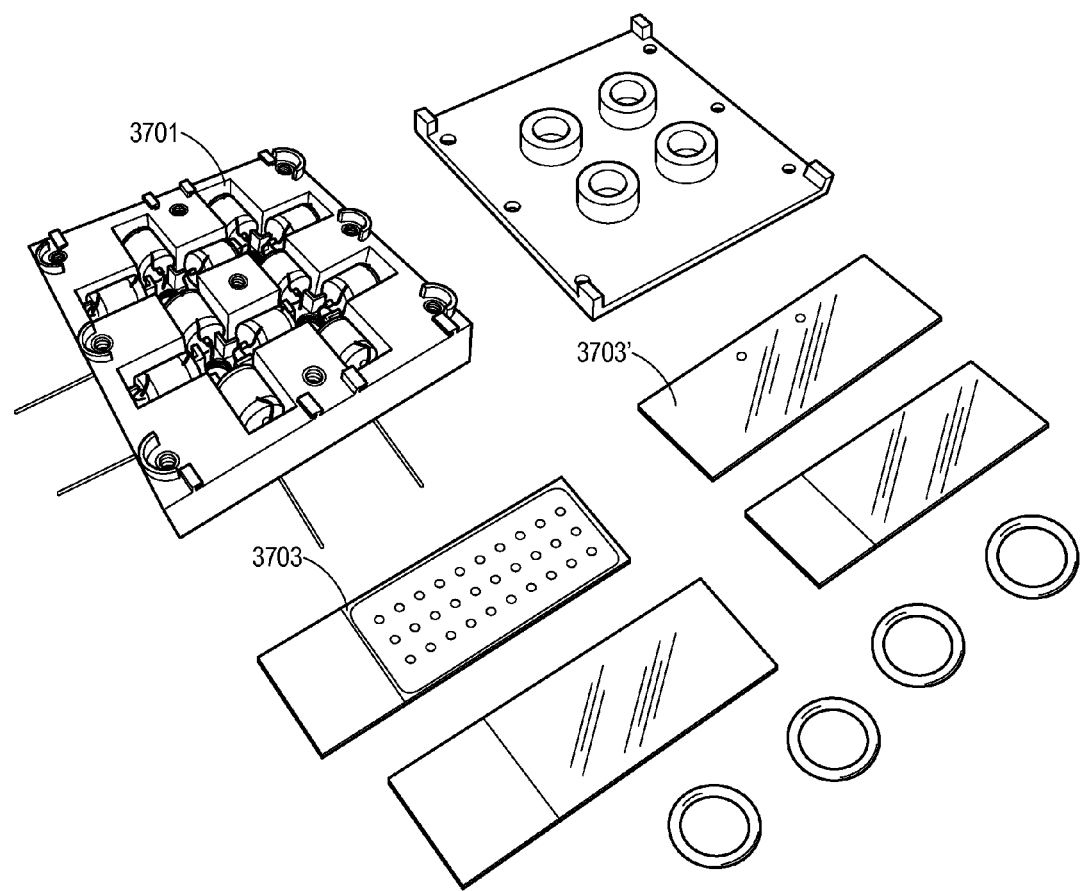
FIG. 37a is a partially disassembled view of a system including the driving magnetic field source shown in FIG. 36 as well as two hanging drop type multiwell plates.
Figure 37B:
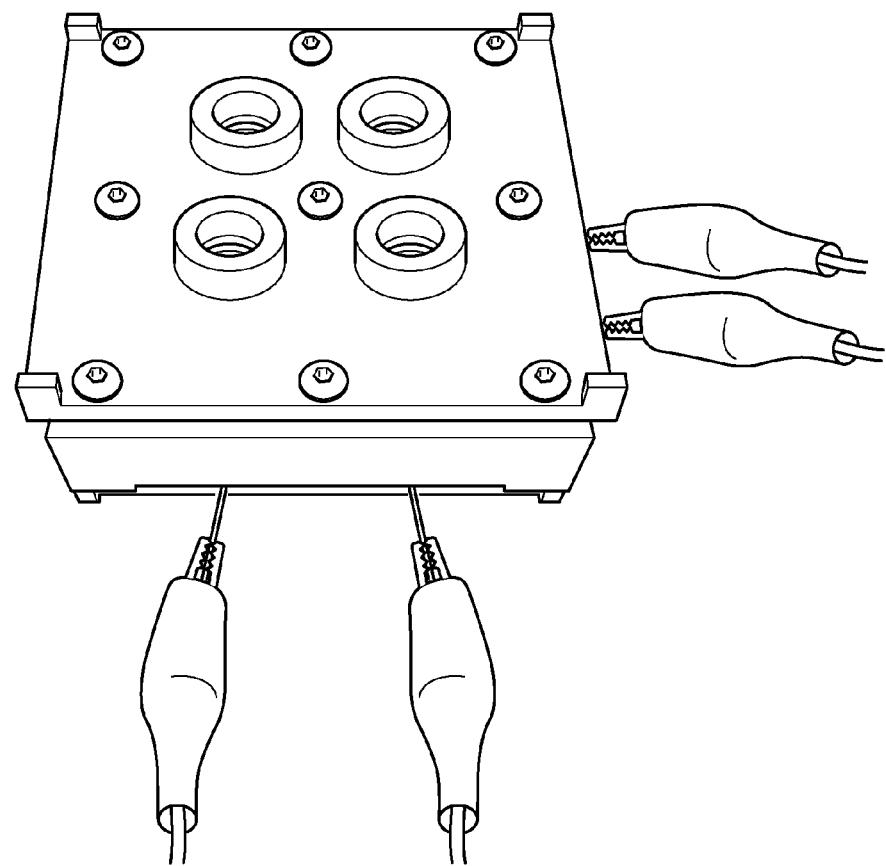
FIG. 37b shows an assembled view of this system. For simplicity, any optical detector (emitter and sensor(s)) components are not shown.

FIGS. 36-38 illustrate a variation of a driving magnetic source having twelve coils arranged to form four rotating magnetic field regions. FIG. 37A shows a disassembled view of a system in which the driving magnetic field source 3701 may be used. In this example two plates 3703, 3703' (shown as slides that have been coated with Teflon to form hanging droplet regions) may be positioned over the regions of rotating magnetic fields and observed using a light source (not shown) and detector (not shown); the detector may be a microscope that takes images (including movies) to record or observe rotating of the magnetic particles. Alternatively, the detector may be any of the detectors described above. FIG. 37B shows an assembled view of the system of FIG. 37A.

Many of the systems described herein may be used with a multiwell plate. Any appropriate multiwell plate may be used. A multiwell plate generally includes two or more wells arranged in a plane (through non-planar configurations may be used). Many of these wells include a curved interface so that fluid surface (and particularly fluid facing the imaging sensor interface (with solid or air) is curved. This curved interface may provide lensing to light passing through, and it may also help cluster or aggregate the magnetic particles.

Figure 39A:
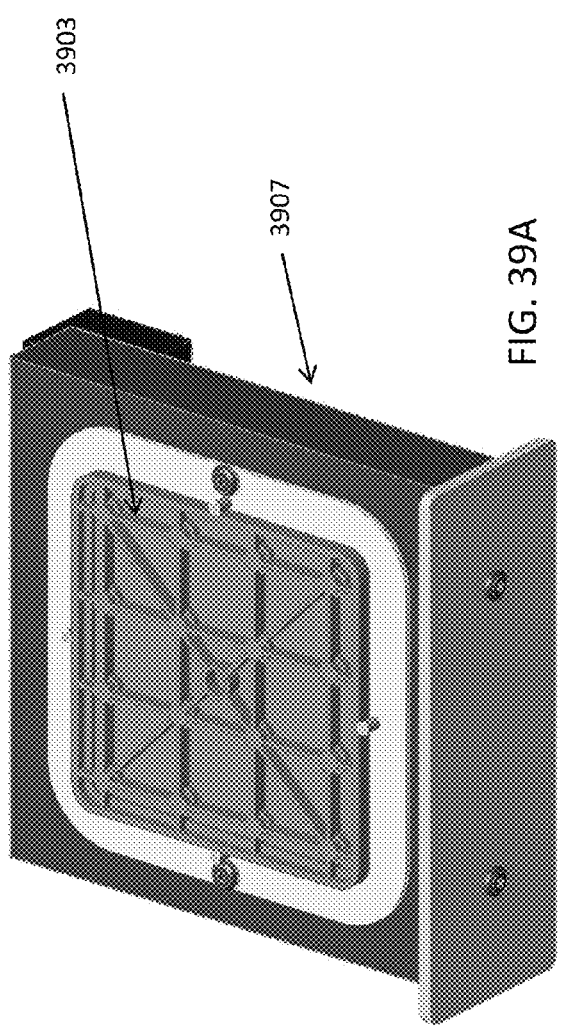
FIGS. 39A and 39B illustrate the insertion of the multiwell pate of FIGS. 38A and 38B into a chamber of a device or system for monitoring AMBR.
Figure 39B:
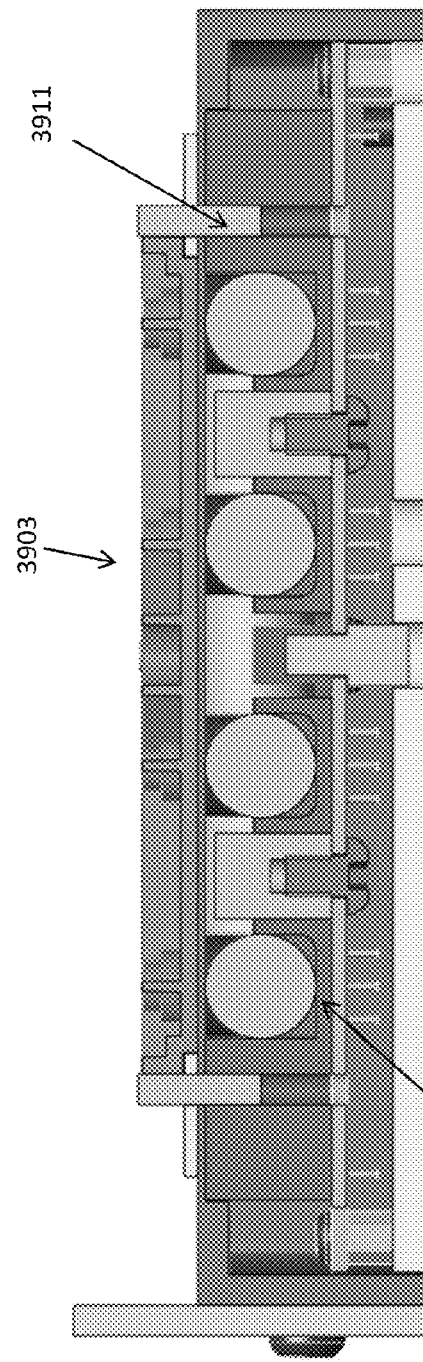

For example, FIGS. 38A and 38B illustrate one variation of a 16 well plate. Although many of the examples described herein include 16 wells, virtually any number of wells may be used, including higher density plates having 32, 96, etc. wells. Many of the features described herein are scalable to accommodate higher densities of wells. In FIG. 38A, showing the bottom of a plate, an array of recessed apertures forming wells into which fluid may be inserted (e.g., by pipetting, dipping, etc.). The bottom of the well is closed in this example. This plate may be inverted to form a hanging droplet well. FIG. 38B shows the top-side of the plate. Top and bottom labels are used for convenience in this example; the bottom of the plate will face towards the imaging sensor (down) when light passed from the top, through the well and onto the plate. Thus the plate may be made of a transmissive (e.g., transparent) material such as an acrylic or polycarbonate material. This exemplary plate may fit within a sample chamber configured to hold the plate, as illustrated in FIGS. 39A and 39B. For example, the plate may fit within the sample chamber 3907 that may be configured as a drawer that extends from and retracts into a housing; the housing may hold the optical detector (including light source(s) and sensor or sensors). The housing may be temperature, humidity and/or gas mixture regulated, or may otherwise function as an incubator.

In some variations the plate may be sealed or sealable to prevent or reduce evaporation and/or contamination of the well. This may be less important in variations for use within an incubator or having their own incubation.

In FIG. 39B, for example, the plate 3903 of FIGS. 38A and 38B engages with the driving magnetic field source 3905; alignment guides (e.g., pins) 3911 extending from the plate secure the plate in alignment with the rest of the system.

Because a system for monitoring asynchronous magnetic bead rotation may be configured to work with a particular plate configuration, the plate may be considered as part of the system. Alternatively, in some variations a system may be compatible with a variety of different plate types and geometries, thus a plate may be optional to the system and a variety of different plates (or no plates at all) may be used.

Other examples of plates are illustrated in FIGS. 40A-44B. For example FIGS. 40A and 40B illustrate schematic views of a 16 well plate similar to that shown in FIG. 38A-39B. Proposed dimensions for this variation include a chamber depth 4001 of 5 mm, a well depth 4003 of 3 mm, and a thickness of greater than 1 mm. The chamber 4009 diameter may be approximately 6 mm, with the width of the well 4007 region approximately 1.75 mm.

Figure 41A:
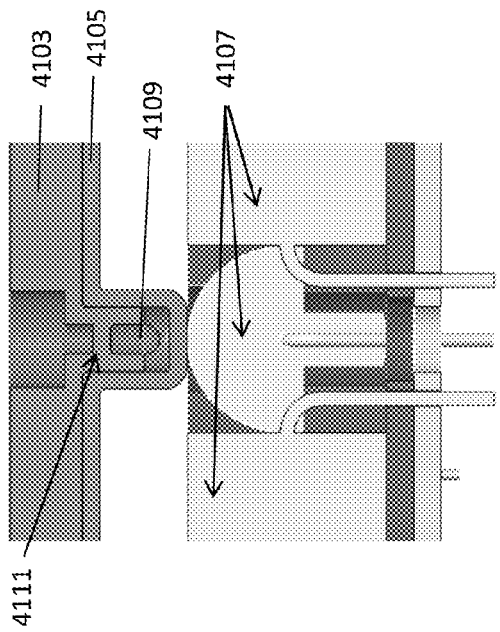
FIGS. 41A and 41B show one variation of a multiwell plate.
Figure 41B:
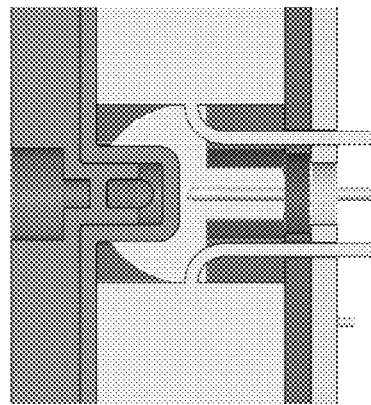
Figure 41C:
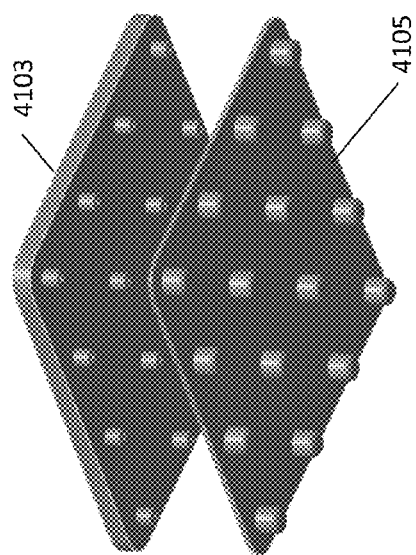
FIGS. 41C and 41D illustrate the plates of FIGS. 41A and 41B engaging with a portion of a system for monitoring asynchronous magnetic bead rotation.
Figure 41D:
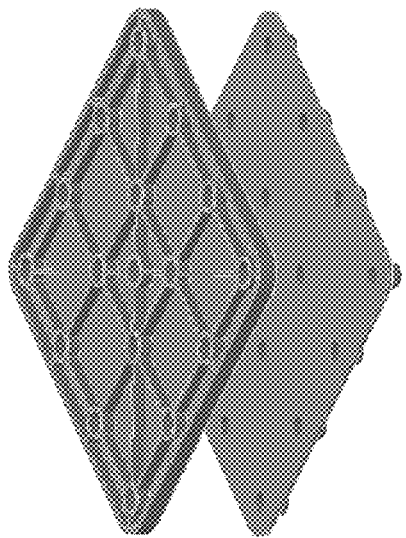
Figure 42C:
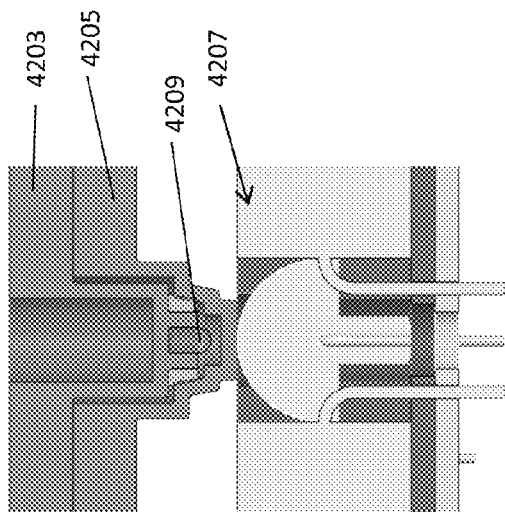
FIGS. 42C and 42D illustrate the plates of FIGS. 42A and 42B engaging with a portion of a system for monitoring asynchronous magnetic bead rotation.
Figure 42D:
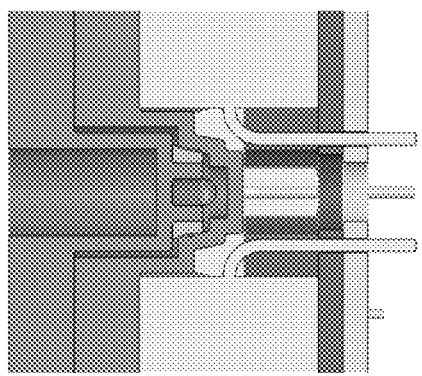
Figure 42A:
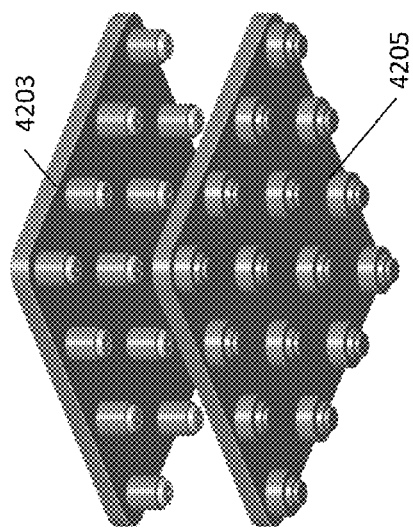
FIGS. 42A and 42B show another variation of a multiwell plate.
Figure 42B:
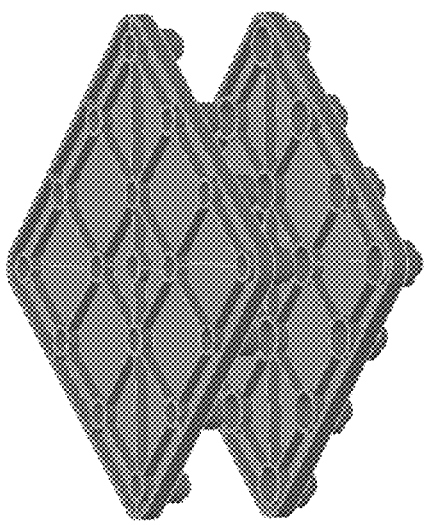
Figure 43C:
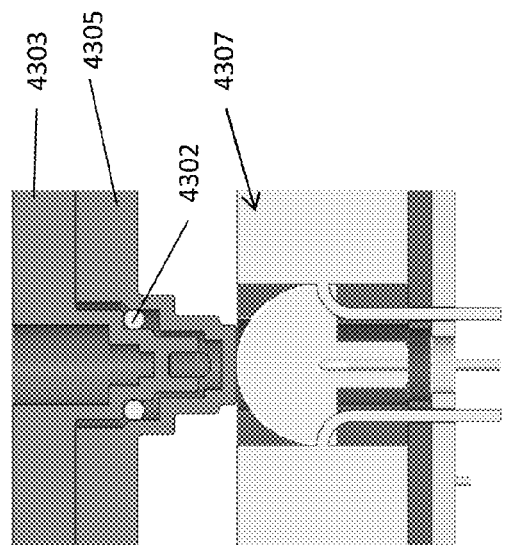
FIGS. 43C and 43D illustrate the plates of FIGS. 43A and 43B engaging with a portion of a system for monitoring asynchronous magnetic bead rotation.
Figure 43D:
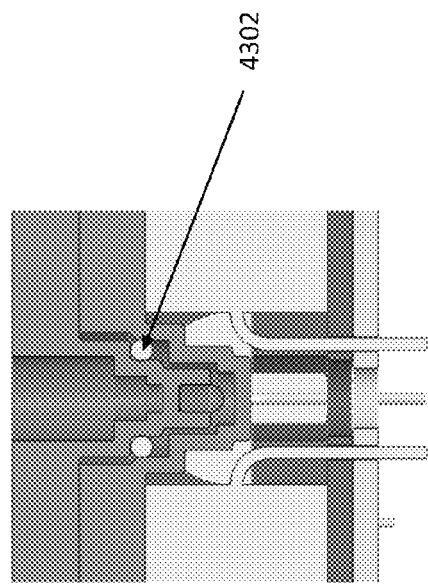
Figure 43A:
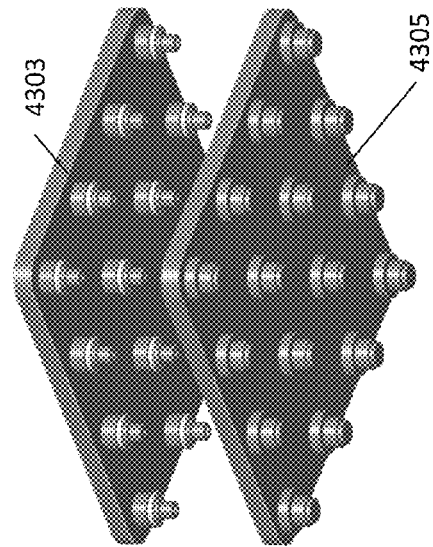
FIGS. 43A and 43B show another variation of a multiwell plate.
Figure 43B:
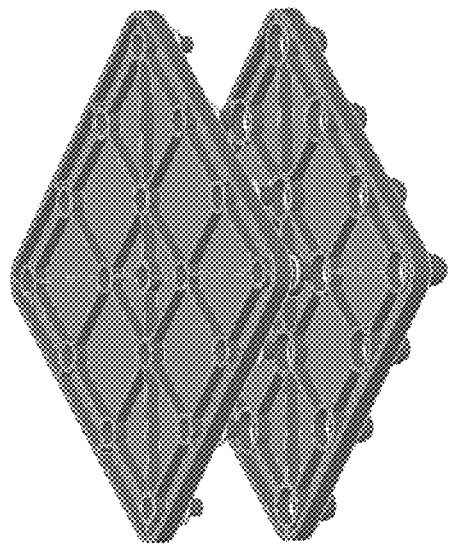

Another variation of a multiwell plate is shown in FIGS. 41A-41D. In this example, the plate includes an upper rigid plate 4103 with a flexible silicone bottom 4105 or cover. The cover may seal the well forming the hanging droplet, preventing evaporation and/or contamination. The cover 4105 may also help position and secure the palate within the chamber of the AMBR system. FIGS. 41A and 41B show bottom and top perspective views, respectively, of the plate 4103 and cover 4105. FIGS. 41C and 41D show the plate 4103 before and after engaging with an AMBR system. The partial cross-section through the AMBR system includes three inductors forming part of the driving magnetic field source sub-system 4107. The palate (including the upper region 4103 and lower region 4105) may be transparent or clear, to allow light transmission through the well. For example, the well portion of the upper plate may be formed of a clear acrylic or polycarbonate; the region beneath the well may be formed of a clear silicone.

In FIG. 41A, the well is a hanging droplet well, which may be open at both ends (allowing addition of material from the top) or closed off at the top (as illustrated in FIG. 41C). Fluid 4109 hangs from the well and forms a curved interface through which light is transmitted down to a sensor (not shown). In some variations the top of the well is closed off 4111; as mentioned, it may be open. In variations in which the top is open, a transparent cover may be used to prevent evaporation. The fluid may remain in the well and form the hanging drop because of the fluid properties (e.g., viscosity of the fluid as well as the capillary forces on the fluid in the well).

FIGS. 42A-42D similarly illustrate another variation of a multiwell plate as shown in FIGS. 41A-41D above. The plate 4203 shown in FIGS. 42A-42D forming the wells (also hanging droplet wells in this example) may be used with a cover 4205, which, unlike the silicone cover of FIG. 41A, may be formed of a transparent rigid material. This plate may also include a gasket integrated (over molded) into the upper plate 4203 to form a seal between the upper plate 4203 and the cover 4205. The cover may protect the handing droplet 4209. Similarly, FIGS. 43A-43D also show another variation of a plate 4303 with a rigid cover 4305; in this variation the plate includes an o-ring 4302 to help seal the rigid cover 4305 to the plate 4303.

Figure 44B:
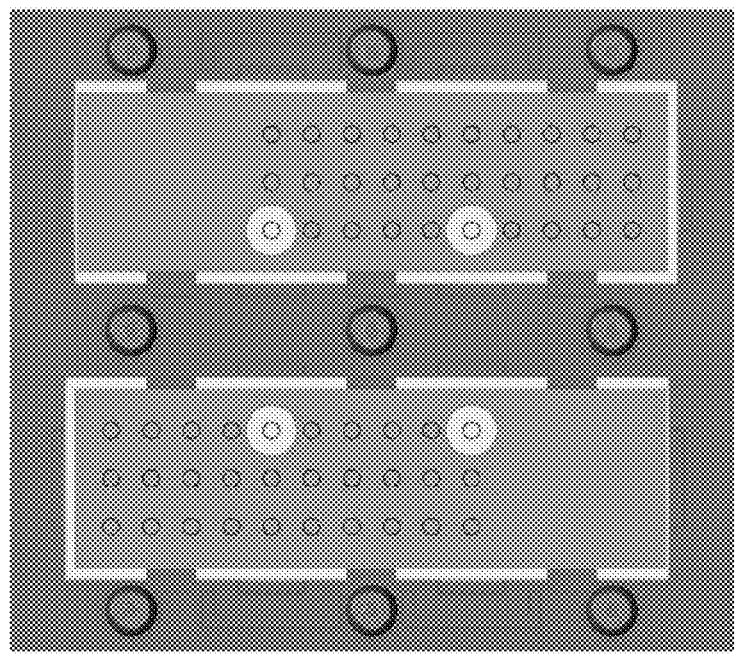
FIGS. 44A and 44B show a variation of a multiwell plate having closed hanging drop wells.
Figure 44A:
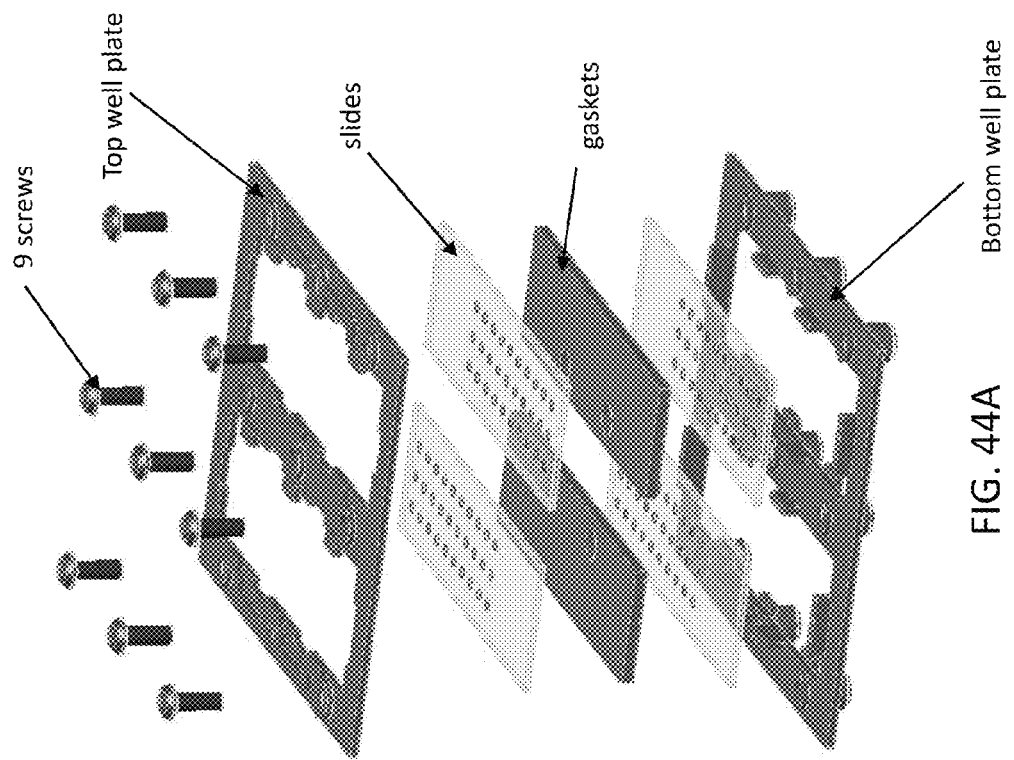

FIG. 44A is an exploded view of another example of a multiwell plate configured as a hanging droplet plate. In this example, the plate include two slides painted with Teflon in all but the hanging droplet regions; fluid placed in these circular regions will form a droplet that can be inverted for use in the system. FIG. 44B shows a top view of the slide of FIG. 44A. The gasket may include a plurality of openings (not shown in detail) behind each handing droplet well, allowing transmission of light.

Figure 45C:
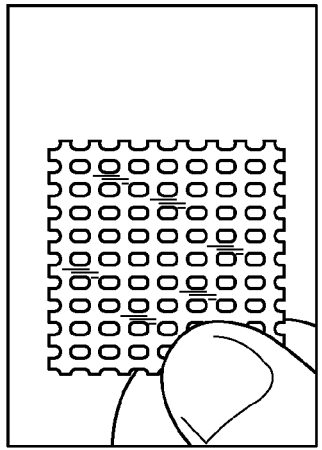
FIGS. 45A, 45C and 45E illustrate variations of meshes that may be used to form hanging droplet wells, as illustrated in FIGS. 45B, 45D and 45F (respectively, for the mesh of FIGS. 45A, 45C and 45E).
Figure 45F:
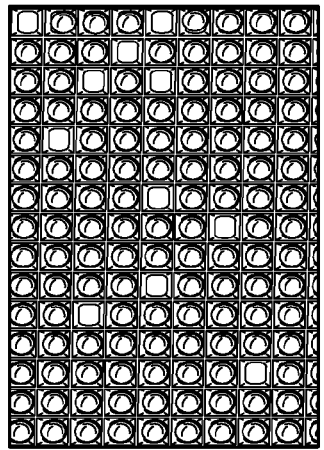
Figure 45B:
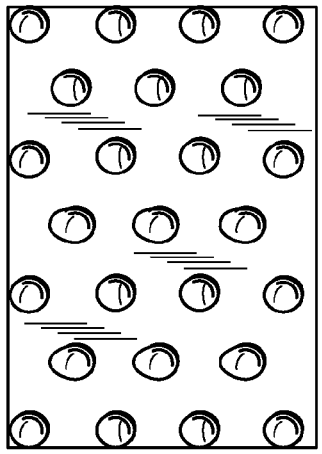
Figure 45E:
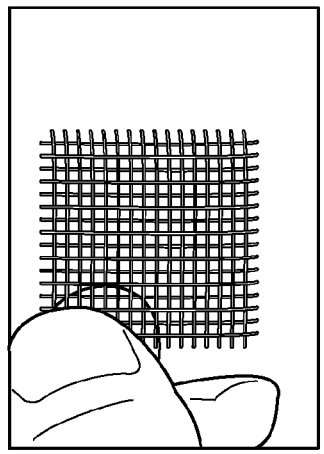
Figure 45A:
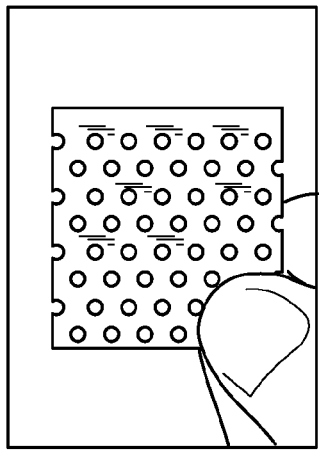
Figure 45D:
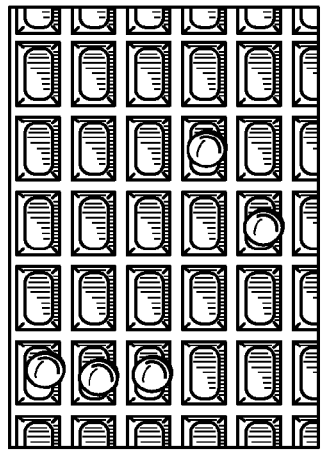

FIGS. 45A-45F illustrate other techniques for forming hanging droplet type slides. In some variation the hanging droplet plate may be configured so that the top of the hanging droplet well is open (rather than being closed, as in the slide variation shown in FIG. 44A). In some variations, the slide may include channels or openings, which may be loaded with fluid and/or magnetic particles and analyte. In hanging droplet plates having openings at the top, fluid and/or magnetic particles and/or analyte may be loaded into the plate from the top of the plate before or after placing them in the chamber of a system or device for performing AMBR. FIGS. 45A, 45C and 45E show different meshes that may be used to form hanging droplets. For example, a plate may include a mesh or opening passing through the device to allow formation of the hanging droplet. FIGS. 45B, 45D and 45F illustrate the formation of hanging droplets within these mesh openings.

Examples of AMBR Using a Cluster of Magnetic Particles

The monitoring of asynchronous rotation of clusters of magnetic particles may provide a simplified and powerful variation of the AMBR technique. Clusters of magnetic particles may be easily recognized because of their asymmetric overall shape, and the overall shape may be influenced by the analyte binding the clusters.

FIGS. 46a-c illustrates one example AMBR using a cluster formed in a well having a curved interface (in this example, a hanging droplet). In FIG. 46a, a schematic illustration shows the lensing effect of the curved interface of the well (in this case the air-fluid interface). This lensing effect may be used to amplify the rotational signal by magnifying the image through the droplet. In this case, a layer of rotating magnetic particles is shown near the bottom of the handing droplet, and light (which does not have to be collimated) is directed down through the well onto the cluster. An LED or laser light may be focused by the droplet curvature, magnifying the 'image' of the particle cluster a 100-fold. After the magnification, the rotational period can be observed and measured using a photodetector, thus observing a periodic signal corresponding to the rotational period of the cluster. FIG. 46b illustrates the change in cluster shape/size and rotation. The rotational period of the cluster changes accordingly: as the cluster itself expands (e.g., changing shape to have a larger diameter); as bacteria or other analytes attach to the cluster and/or expand/swell; or as the viscosity of the surrounding fluid changes. Viscosity may change if unbound cells divide and increase in number within the well. The rotational period of the cluster can be measured using the Fast Fourier Transform (FFT). The lower graphs in FIG. 46b show a shift in the peak observing the peak location.

As mentioned above, the shape and size of the clusters may affect the rate of rotation during asynchronous rotation. This shape and size may be modified or controlled during formation of the clusters, and by controlling the number of particles and/or the shape of the well (e.g., curvature of the well).

FIG. 46c shows an optical microscopy image sequence of a self-assembled magnetic particle cluster rotating asynchronously in a rotating magnetic field. Images are taken every 400 ms, with magnetic field frequency of 20 Hz and 1 mT field strength. The resulting rotational period of the driven cluster is 1.7 s. In this sequence, the cluster is asymmetrically rotating counterclockwise, moving from left to right across the images.

The technique illustrated in FIGS. 46a-c was used to measure the rotation rate of the clusters, and therefore monitoring for bacterial growth, and this information was used to determine a minimum inhibitory concentration (MIC) for two antibiotics using uropathogenic E. coli. This is illustrated in FIGS. 47a-g.

In FIGS. 47a-g, the normalized (at early time) rotational period of magnetic particle clusters was used to observe the growth of surrounding uropathogenic E. coli, under different concentrations of antibiotics (streptomycin and gentamicin). When the antibiotic is ineffective, the bacteria keep growing and progressively slowing down the rotation of the cluster; however when the antibiotic is effective, the growth is inhibited, thus keeping the rotational period constant, in this example. In FIGS. 47*a* and 47*b*, data points were taken every 10 minutes and are shown connected for clarity.

FIG. 47*c* shows optical microscopy images of self-assembled magnetic particles (e.g. clusters) used in the AMBR assays with different concentrations of streptomycin (data in 47*a*), at time 160 minutes, showing a part of the cluster so as to highlight the abundance or scarcity of the bacteria. The scale bar is 10 μm. FIG. 47*d* shows the rotational frequency of a typical self-assembled cluster of particles as a function of time, where a few obvious outliers have been removed. The standard deviation of the frequency is 0.7%. FIG. 47*e* shows the rotational frequency of a magnetic particle cluster as a function of the magnetic field strength. This is discussed in greater detail below for FIG. 51. The data is fitted with a quadratic relationship. FIG. 47*f* shows the rotational frequency as a function of the driving frequency, on a semi logarithmic axis. The error bars are the deviation between four similar sized clusters (roughly 800 particles per cluster). The effect of size/packing of the magnetic particles in a cluster on rotational rate may be seen in FIG. 47*g*, which shows the rotational frequency of clusters as a function of the packing density divided by Feret's diameter (maximum caliber) of the cluster. There is a good correlation.

The self-assembled magnetic particles shown in FIG. 47*a-g* enabled rapid MIC measurements, and the determined values agreed with values obtained with the traditional microdilution method. The clinical MIC of the uropathogenic *E. coli* isolate was known to be 16 μg/mL for streptomycin and 2 μg/mL for gentamicin (as determined with Vitek 2, an FDA approved automated system for susceptibility tests). Using the techniques described above, the MIC values measured were, respectively, 8 and 2 μg/mL (from FIGS. 47*a* and 47*b*), which are consistent within the one doubling dilution uncertainty with the reference MIC.

Figures 48A, 48B:
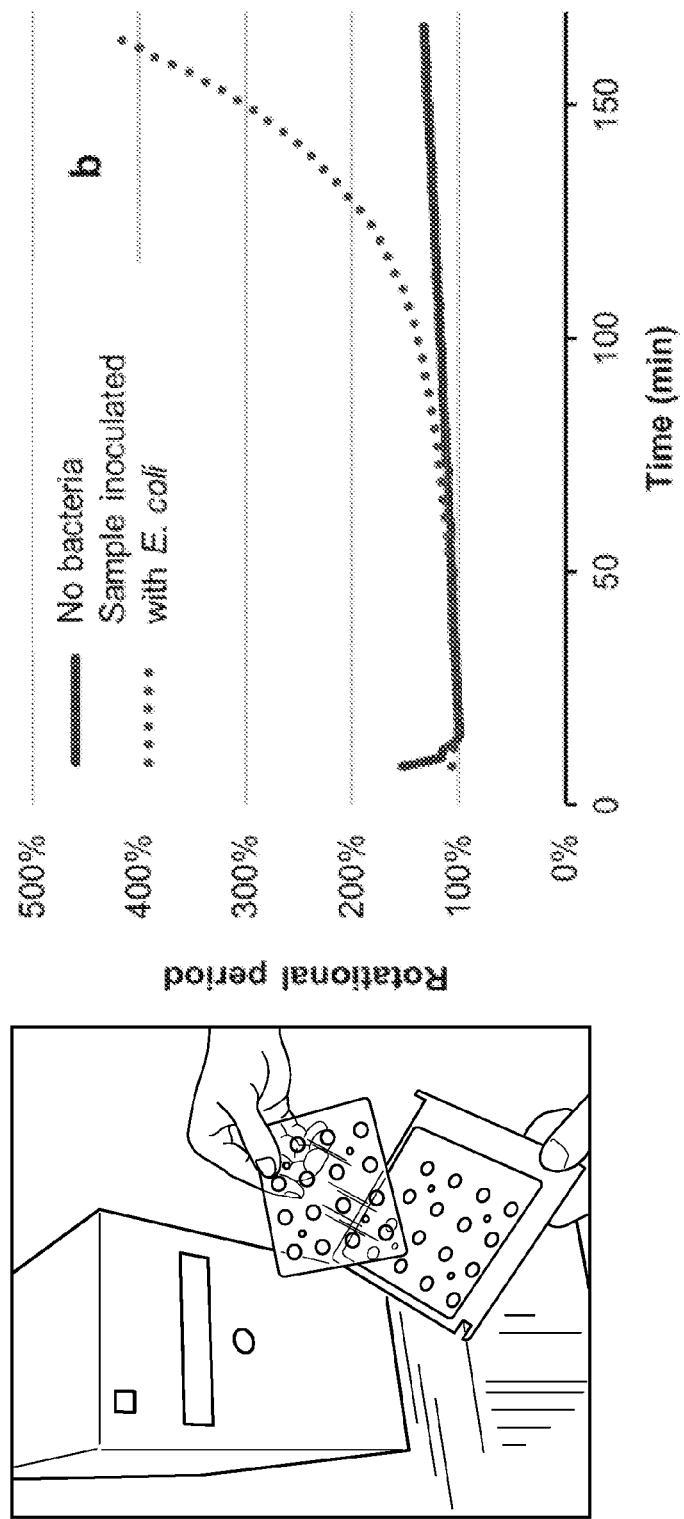
FIG. 48a shows one example of a system for performing AMBR using clusters of magnetic particles.
FIG. 48b shows is a graph showing cellular growth using a cluster of magnetic particles.

FIG. 48*a* shows an image of the prototype system used to make some of the measurements described above. In this embodiment, a housing covers the imaging various system parts. This prototype, which could be used in an incubator, does not control for evaporation, which is apparent from the graph shown in FIG. 48*b*. FIG. 48*b* shows the rotational period over time for a cluster of magnetic particles both with (dotted line) and without (solid line) bacteria added. Bacterial growth is resolved as an increase in the rotational period (i.e. a slowing of the rotation of the cluster) over time. The cluster without bacteria showed a slight increase in period (slowing down), likely due to evaporation of the fluid in the well. Control of the humidity around the well (e.g., use with or as an incubator) could prevent this slight inaccuracy.

Figure 49C:
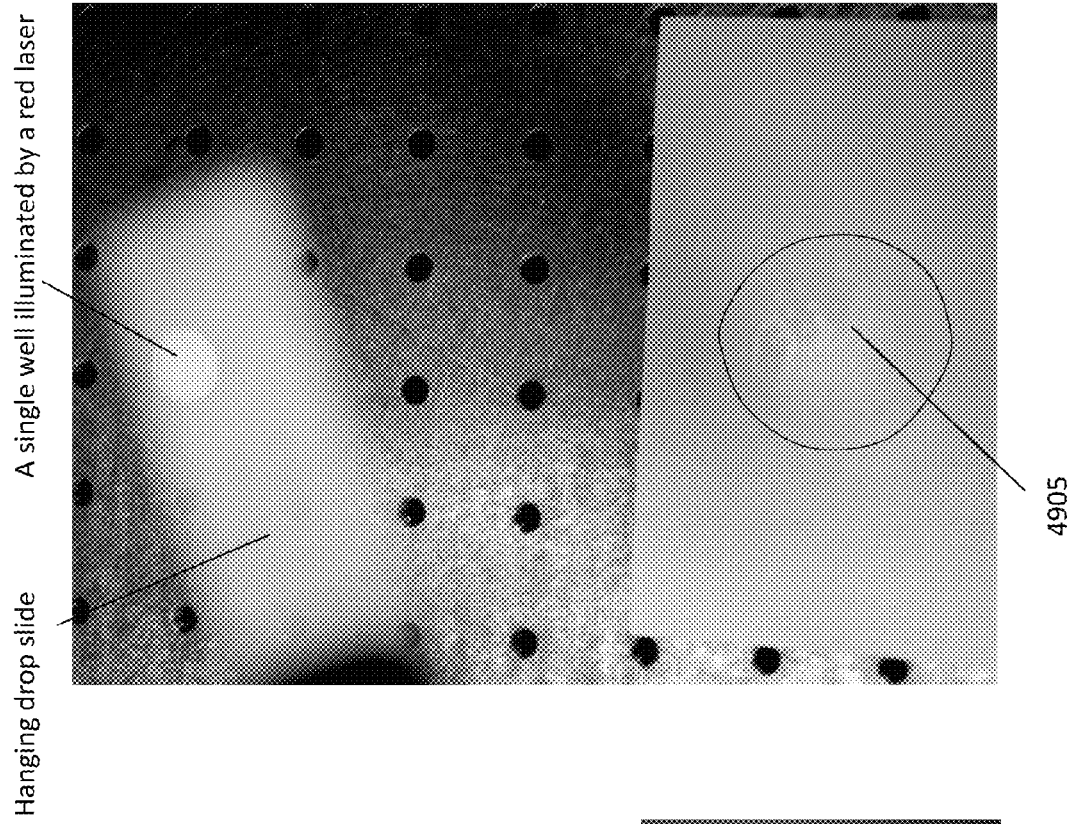
FIG. 49C illustrates imaging rotation of a cluster of magnetic particles though the well.
Figure 49:
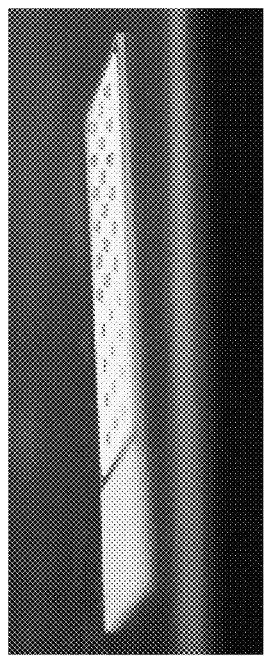
FIGS. 49A and 49B show a handing droplet well slide.
Figure 49B:
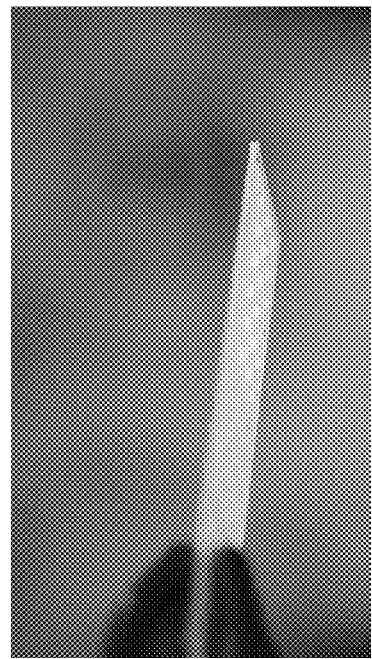

FIG. 49A shows another example of a plate having hanging drop wells. The plate in this example is a commercially available glass microscope slide coated with Teflon, with millimeter-scale glass circles left Teflon-free to form wells that may then form droplets. Each well is populated with a small amount of fluid and magnetic beads. The plate can then be inverted so that magnetic bead clusters are formed. This is shown in FIG. 49B, showing the wells inverted and the droplets hanging. FIG. 49C shows the inverted plate with hanging drops in which one well has been illuminated with a laser, and is held in place above the table so that; the plate is out of focus near the top of the figure. The laser light passes through the hanging drop well and the resulting image (pattern or signal) is projected onto a white sheet of piece of paper; in FIG. 49C the paper is shown in focus (paper is supported by the table). The dark spots 4905 shown on the paper are shadow images of the magnetic particles in the well. The rotation of the cluster of particles shown shadow image can be monitored with the described detectors as discussed above. Another similar illustration of this technique is shown in FIG. 50A-C.

FIG. 50A illustrates another technique for implementing a through-hole hanging drop plate. In this example, a hanging drop plate was constructed from a solid sheet of Teflon. A series of holes were drilled through the Teflon so that each hole could be used as a well. Each hole or "well" was then populated with fluid and magnetic beads, which is shown in more detail in FIG. 50B. In FIG. 50A, for size comparison, a different disposable plate available from a commercially available system (from the Vitek 2 system) is shown behind the custom made plate. Once loaded with media and magnetic beads, magnetic bead clusters were then formed at the bottom of each well. This may be seen in FIG. 50C, which shows the hanging drop plate with one well illuminated with a laser; the plate is held in place above the optical table. The laser light passes through the hanging drop array plate (shown to be out of focus in FIG. 50C) and the resulting image (pattern or signal) is depicted on the white piece of paper, which is shown in focus (paper is resting on the table). One difference between the plate shown in FIGS. 49*a* and 50*n* is that the through hole plate allows for double lensing (see FIG. 16F) and allows for access for the addition of reagents to the hanging drop from above.

Figure 51:
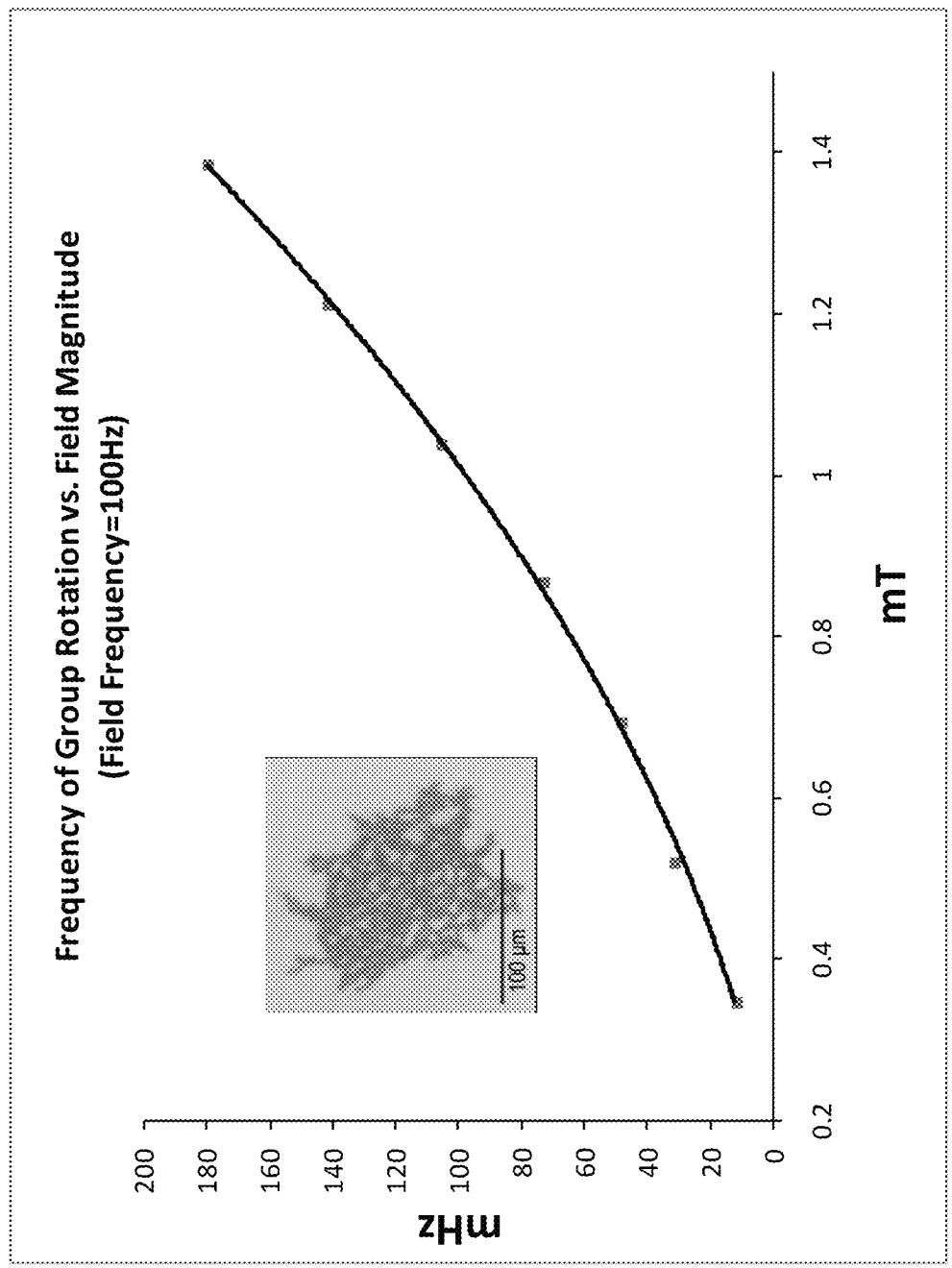
FIG. 51 illustrates the relationship between the frequency of rotation of a cluster of magnetic particles and the magnitude of the driving magnetic field.

FIG. 51 illustrates the relationship between the amplitude of the driving magnetic field and the frequency of rotation of a cluster of magnetic particles. In general the amplitude and rate of rotation of the driving magnetic field may be chosen so that the cluster of magnetic particles rotates in the asymmetric mode at an initial frequency in a desired range. For example, it may be desirable to have an initial asymmetric rate of rotation for the cluster of magnetic particles that is within the range of 0.1 Hz to about 100 Hz (e.g., approximately 1 Hz).

In order to achieve a 1 Hz rotational frequency of the cluster of magnetic particles, the driving field may be set to an amplitude of about 4.4 mT, assuming a cluster similar to the one shown in FIG. 51 (inset). With ½ of this amplitude, we would expect to have ¼ group frequency (4 s period), because the group rotation frequency is proportional to the square of the magnetic field amplitude (see the graph in FIG. 51). Also the magnetic field amplitude is proportional to the current passing through the inductors, therefore doubling the current would increase the group rotation frequency by a factor of 4.

Thus, in FIG. 51, the effect of field magnitude on group rotation rate is illustrated. A single cluster of magnetic particles was subjected to a 100 Hz rotating magnetic field of varying amplitude. The data shows that the rotation rate depends on the square of the field, indicative of superparamagnetic behavior by the magnetic particles. Other magnetic particles (e.g., paramagnetic or ferromagnetic) may also be used, and show a different relationship.

In FIG. 51, an inverted drop of a single well was used with a group size of several hundred beads. The plot in FIG. 51 shows the rotational frequency dependence on field amplitude; in particular, the data shows that the rotation rate depends on the square of the field, indicative of superparamagnetic behavior.

Additional details pertinent to the present invention, including materials and techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. A method of monitoring cell growth and/or binding by asynchronous magnetic bead rotation (AMBR) in a cluster of magnetic particles, the method comprising:

allowing cells to bind to magnetic particles;

forming a cluster of the magnetic particles and bound cells such that the cluster of magnetic particles and bound cells are restrained against individual rotation, but are free to rotate together, wherein forming the cluster comprises forming the cluster by magnetic-field-induced magnetic interaction between the magnetic particles to establish a low interparticle distance between the magnetic particles;

applying a rotating magnetic field, wherein the orientation of the rotating magnetic field changes over time and the field intensity is maintained constant, at a driving rate so that the cluster of magnetic particles rotate asynchronously to the applied magnetic field at an asynchronous rotation rate, wherein the rotating magnetic field rotates around an axis and wherein the cluster of magnetic particles and bound cells rotate asynchronously about the axis when the rotating magnetic field is above a critical rotation rate for inducing asynchronous rotation of the cluster of magnetic particles and wherein the critical rotation rate varies depending on the cluster of magnetic particles; and detecting a change in the asynchronous rotation rate indicative of cellular binding and/or growth in the cells.

2. The method of claim 1, further comprising magnetically separating the magnetic particles from a sample containing the cells.

3. The method of claim 1, wherein forming comprises forming a cluster of magnetic particles in a planar surface.

4. The method of claim 1, wherein allowing the cells to bind to the magnetic particles comprises combining the magnetic particles and cells before the magnetic particles are clustered.

5. The method of claim 1, wherein allowing cells to bind to the magnetic particles comprises adding a sample including the cells to the magnetic particles.

6. The method of claim 1, wherein forming the cluster of magnetic particles comprises forming a cluster of greater than about 5 particles.

7. The method of claim 1, wherein forming the cluster of magnetic particles comprises forming a cluster of between about 10 and about 10,000 particles.

8. The method of claim 1, wherein applying a rotating magnetic field comprises applying a rotating magnetic field of constant amplitude.

9. The method of claim 1, wherein the cells comprise bacterial cells.

10. The method of claim 1, wherein forming the cluster of magnetic particles comprises applying a magnetic field to establish the low interparticle distance between the magnetic particles and applying the magnetic field before applying the rotating magnetic field.

11. The method of claim 1, further comprising positioning the clustered magnetic particles within a curved interface.

12. The method of claim 1, wherein forming the cluster comprises forming a cluster of magnetic particles in a globular geometry.

13. The method of claim 1, wherein forming the cluster comprises forming a cluster of magnetic particles in a linear geometry.

14. The method of claim 1, wherein forming the cluster comprises:

initially applying the rotating magnetic field at an increased intensity or an increased rate of rotation to establish the low interparticle distance between the magnetic particles; and subsequently applying the rotating magnetic field at the driving rate so that the cluster of magnetic particles rotate asynchronously to the applied magnetic field at the asynchronous rotation rate.

15. The method of claim 1, further comprising binding at least one of the magnetic particles to a protein that further binds the cluster.

16. The method of claim 1, further comprising binding at least one of the magnetic particles to a surfactant that further allows rotation of the cluster at an interface.

* * * * *

UNITED STATES PATENT AND TRADEMARK OFFICE
CERTIFICATE OF CORRECTION

PATENT NO. : 8,846,331 B2  
APPLICATION NO. : 13/220381  
DATED : September 30, 2014  
INVENTOR(S) : Brandon H. McNaughton et al.

It is certified that error appears in the above-identified patent and that said Letters Patent is hereby corrected as shown below:

On the Title Page:

At item (57), line 5, "descried." should be -- described. --.

Signed and Sealed this
Twenty-seventh Day of October, 2015

Michelle K. Lee
*Director of the United States Patent and Trademark Office*